(12) United States Patent
Buettelmann et al.

(10) Patent No.: US 7,956,074 B2
(45) Date of Patent: Jun. 7, 2011

(54) ARYL-ISOXAZOLO-4-YL-OXADIAZOLE DERIVATIVES

(75) Inventors: Bernd Buettelmann, Schopfheim (DE); Bo Han, Shanghai (CN); Henner Knust, Rheinfelden (DE); Andreas Koblet, Bottmingen (CH); Andrew Thomas, Binningen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 122 days.

(21) Appl. No.: 12/422,317

(22) Filed: Apr. 13, 2009

(65) Prior Publication Data

US 2009/0197875 A1 Aug. 6, 2009

Related U.S. Application Data

(62) Division of application No. 11/639,695, filed on Dec. 15, 2006, now Pat. No. 7,541,372.

(30) Foreign Application Priority Data

Dec. 23, 2005 (EP) .................................. 05112956

(51) Int. Cl.
*A61K 31/422* (2006.01)
*A61K 31/4245* (2006.01)
*C07D 261/06* (2006.01)
*C07D 271/10* (2006.01)
(52) U.S. Cl. ......... 514/364; 514/378; 548/143; 548/247
(58) Field of Classification Search .................. 514/364, 514/378; 548/247, 143
See application file for complete search history.

(56) References Cited

U.S. PATENT DOCUMENTS

| 2003/0055085 A1 | 3/2003 | Wagener et al. |
| 2004/0006226 A1 | 1/2004 | Ladduwahetty et al. |
| 2007/0060589 A1 | 3/2007 | Purandare et al. |

FOREIGN PATENT DOCUMENTS

| GB | 2336589 | 10/1999 |
| WO | WO 01/29015 | 4/2001 |
| WO | WO 02/50062 A2 | 6/2002 |
| WO | WO 02/081474 A1 | 10/2002 |
| WO | WO 03/004027 | 1/2003 |
| WO | WO 2005/123672 A2 | 12/2005 |
| WO | WO 2006/044617 | 4/2006 |
| WO | WO 2006/069155 | 6/2006 |

OTHER PUBLICATIONS

Andosova et al., Khimiko-Farmatsevticheskii Zhurnal, 1978, 12(8), p. 63-66 (Abstract from STN search report).*
McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Burke, et al., Journal of Natural Products, 1986, vol. 49, pp. 522-523.
Hamper et al., J. Agric. Food Chem. (1995), vol. 43, pp. 219-228.
Kumar, et al., Tetrahedron Letters, vol. 47, (2006), pp. 1457-1460.
Hormi, Organic Syntheses, vol. 8, p. 247 (1993) & Vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Sur et al., Brain Research vol. 822 (1999) pp. 265-270.
Otani et al., Neuroscience Letters vol. 381 (2005) pp. 108-113.
Gaba A Receptor, Wikipedia, (2009 on-line).

* cited by examiner

*Primary Examiner* — Yong Chu
(74) *Attorney, Agent, or Firm* — George W. Johnston; Patricia S. Rocha-Tramaloni; Kimberly J. Prior

(57) ABSTRACT

The present invention is concerned with isoxazol-4-yl-oxadiazole derivatives of formula

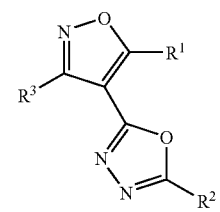

wherein
$R^1$,
$R^2$, and
$R^3$, are as defined in the specification and pharmaceutically acceptable acid addition salts thereof.
This class of compounds has high affinity and selectivity for GABA A α5 receptor binding sites and might be useful as cognitive enhancer or for the treatment of cognitive disorders like Alzheimer's disease.

14 Claims, No Drawings

ARYL-ISOXAZOLO-4-YL-OXADIAZOLE DERIVATIVES

PRIORITY TO RELATED APPLICATIONS

This application is a division of U.S. application Ser. No. 11/639,695, filed Dec. 15, 2006, now pending; which claims the benefit of European Application No. 05112956.7, filed Dec. 23, 2005. The entire contents of the above-identified applications are hereby incorporated by reference.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR. It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides isoxazol-4-yl-oxadiazole derivatives of formula I

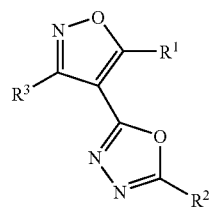

I wherein
$R^1$ is hydrogen, halogen, aryl, heterocyclyl, heteroaryl, cyano, lower alkyl, —$(CH_2)_n$-cycloalkyl, —$(CH_2)_n$—N$(R)_2$, —$(CH_2)_n$—O-lower alkyl or —$(CH_2)_n$—OH;
n is 0, 1 or 2
R is hydrogen or lower alkyl;
$R^2$ is cycloalkyl, aryl, heteroaryl or heterocyclyl, each of which is optionally substituted by one or more substituents selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —$NR^aR^b$,
—C(O)—$NR^aR^b$, —C(O)-heterocyclyl, benzyloxy, heterocyclyl optionally substituted by hydroxy, halogen or lower alkyl, and heteroaryl optionally substituted by lower alkyl;
$R^a$ and $R^b$ are each independently hydrogen, lower alkylsulfonyl, —C(O)H, —$(CH_2)_n$—N$(R)_2$, —$(CH_2)_n$—O-lower alkyl, —$(CH_2)_n$—S-lower alkyl, —$(CH_2)_n$—S(O)$_2$-lower alkyl, heteroarylsulfonyl, lower alkyl, —$(CH_2)_n$-heterocyclyl optionally substituted by lower alkyl, —$(CH_2)_n$-cycloalkyl, —$(CH_2)_n$-heteroaryl, —$(CH_2)_n$—OH, or —(CO)—R', wherein R' is lower alkyl, cycloalkyl or heteroaryl;
$R^3$ is aryl or heteroaryl, each of which is optionally substituted by halogen or lower alkyl substituted by halogen;
and pharmaceutically acceptable acid addition salts thereof.

The present invention also provides pharmaceutical compositions containing a therapeutically effective amount of a compound of formula I or a pharmaceutically acceptable salt thereof and a pharmaceutically acceptable carrier. The invention further provides processes for preparation of the compounds of the invention and pharmaceutical compositions containing them.

This class of compounds has high affinity and selectivity for GABA A α5 receptor binding sites and might be useful as a cognitive enhancer or for the treatment of cognitive disorders like Alzheimer's disease. Therefor, the present invention provides a methods for enhancing cognition or treating cognitive disorders which comprise administering to an individual, a therapeutically effective amount of a compound of formula I or a pharmaceutically acceptable salt thereof.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

The term "lower alkoxy" denotes a lower alkyl group as defined hereinabove linked via an oxygen atom. Examples of lower alkoxy include methoxy and ethoxy as well as those groups that are specifically illustrated with the examples of the compounds of the invention hereinafter.

The terms "lower alkyl substituted by halogen" and "lower alkoxy substituted by halogen" respectively denote a lower alkyl or lower alkoxy group as defined hereinabove, in which one or more of the hydrogen atoms have be replaced by a halogen atom; i.e., the lower alkyl or lower alkoxy group substituted by one or more halogen atom; preferably by one, two or three fluorine atoms. Examples of such groups include $OCHF_2$, $OCF_3$, and $CF_3$, as well as those groups that are specifically illustrated with the examples of the compounds of the invention hereinafter.

The term "lower alkylsulfonyl" denotes a lower alkyl group as defined hereinabove linked via an —S(O)$_2$— group. Examples of lower alkylsulfonyl groups include methylsulfonyl and ethylsulfonyl as well as those groups that are specifically illustrated with the examples of the compounds of the invention hereinafter.

The term "heterocyclyl" denotes a monocyclic or bicyclic ring comprising from 1 to 9 carbon atoms as ring members, with the remaining ring member atoms being selected from one or more O, N and S. Preferred heterocyclyl groups are 5 or 6 membered heterocycloalkyl groups. Examples of such groups include piperidine, piperazine, morpholine, pyrrolidin, pyrrolidin-2-one, imidazolidin-2-one, tetrahydrofuran, thiomorpholine, thiomorpholine-1-oxide, thiomorpholinel-1,1-dioxide, 1-H-benzoimidazole, 1,3-dihydro-benzolimidazole-2-one, tetrahydro-pyrane, and 1,3-dimethyl-1,3-dihydro-benzoimidazol-2-one as well as those groups specifically illustrated by the examples herein below.

The term "aryl" denotes an unsaturated, aromatic carbon ring, for example a phenyl, benzyl or naphthyl group. A preferred aryl group is phenyl.

The term "halogen" denotes chlorine, iodine, fluorine and bromine.

The term "cycloalkyl" denotes a cyclic hydrocarbon ring, having from 3 to 7 carbon ring atoms, for example, cyclopropyl, cyclopentyl or cyclohexyl.

The term "heteroaryl" denotes a ring system containing one or two rings, wherein at least one ring is aromatic in nature and contains from one to three heteroatoms, such as N, O or S atoms. Examples of such heteroaryl groups include quinolyl, indolyl, pyridinyl, triazolyl, benzotriazolyl, isoxazolyl, furanyl, thiophenyl, benzoimidazolyl, dihydrobenzimidazolyl-2-one, imidazolyl, oxazolyl, oxadiazolyl and pyrazinyl as well as those groups specifically illustrated by the examples herein below.

The term "heteroarylsulfonyl" denotes a heteroaryl group as defined above which is attached via a sulfonyl group.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides isoxazol-4-yl-oxadiazole derivatives of formula I

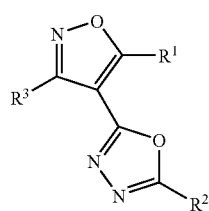

I wherein
R$^1$ is hydrogen, halogen, aryl, heterocyclyl, heteroaryl, cyano, lower alkyl, —(CH$_2$)$_n$-cycloalkyl, —(CH$_2$)$_n$—N(R)$_2$, —(CH$_2$)$_n$—O-lower alkyl or —(CH$_2$)$_n$—OH;
n is 0, 1 or 2
R is hydrogen or lower alkyl;
R$^2$ is cycloalkyl, aryl, heteroaryl or heterocyclyl, each of which is optionally substituted by one or more substituents selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NR$^a$R$^b$,
—C(O)—NR$^a$R$^b$, —C(O)-heterocyclyl, benzyloxy, heterocyclyl optionally substituted by hydroxy, halogen or lower alkyl, and heteroaryl optionally substituted by lower alkyl;
R$^a$ and R$^b$ are each independently hydrogen, lower alkylsulfonyl, —C(O)H, —(CH$_2$)$_n$—N(R)$_2$, —(CH$_2$)$_n$—O-lower alkyl, —(CH$_2$)$_n$—S-lower alkyl, —(CH$_2$)$_n$—S(O)$_2$-lower alkyl, heteroarylsulfonyl, lower alkyl, —(CH$_2$)$_n$-heterocyclyl optionally substituted by lower alkyl, —(CH$_2$)$_n$-cycloalkyl, —(CH$_2$)$_n$-heteroaryl, —(CH$_2$)$_n$—OH, or —(CO)—R', wherein R' is lower alkyl, cycloalkyl or heteroaryl;
R$^3$ is aryl or heteroaryl, each of which is optionally substituted by halogen or lower alkyl substituted by halogen;
and pharmaceutically acceptable acid addition salts thereof.

Preferred are compounds that have a binding activity (hKi) of lower than 400 nM, are selective for GABA A α5 subunits, and are relatively free of activity at GABA A α1, α2 and α3 receptor binding sites. Most preferred are compounds which have a binding activity (hKi) of lower than 35 nM at the GABA A α5 subunit.

In a certain embodiment, the compounds of the invention are those compounds, wherein R$^2$ is aryl, which is optionally substituted by one or more substituents selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NR$^a$R$^b$, —C(O)—NR$^a$R$^b$, —C(O)-heterocyclyl, benzyloxy, heterocyclyl optionally substituted by hydroxy, halogen or lower alkyl, and heteroaryl optionally substituted by lower alkyl, and the other definitions are as above.

The following are examples of such compounds:
2-(5-methyl-3-phenyl-isoxazol-4-yl)-5-phenyl-[1,3,4]oxadiazole,
2-(5-methyl-3-phenyl-isoxazol-4-yl)-5-o-tolyl-[1,3,4]oxadiazole,
2-(3-methoxy-phenyl)-5-(5-methyl-3-phenyl-isoxazol-4-yl)-[1,3,4]oxadiazole,
2-(2-methoxy-phenyl)-5-(5-methyl-3-phenyl-isoxazol-4-yl)-[1,3,4]oxadiazole,
2-(4-methoxy-phenyl)-5-(5-methyl-3-phenyl-isoxazol-4-yl)-[1,3,4]oxadiazole,
2-(2-ethoxy-phenyl)-5-(5-methyl-3-phenyl-isoxazol-4-yl)-[1,3,4]oxadiazole,
2-(2,4-dimethoxy-phenyl)-5-(5-methyl-3-phenyl-isoxazol-4-yl)-[1,3,4]oxadiazole,
2-(2-methoxy-4-nitro-phenyl)-5-(5-methyl-3-phenyl-isoxazol-4-yl)-[1,3,4]oxadiazole,
2-[5-(5-methyl-3-phenyl-isoxazol-4-yl)-[1,3,4]oxadiazol-2-yl]-phenylamine,
3-methoxy-4-[5-(5-methyl-3-phenyl-isoxazol-4-yl)-[1,3,4]oxadiazol-2-yl]-phenylamine, 2-(2-methoxy-4-methyl-phenyl)-5-(5-methyl-3-phenyl-isoxazol-4-yl)-[1,3,4]oxadiazole, 2-(2,5-dimethoxy-phenyl)-5-(5-methyl-3-phenyl-isoxazol-4-yl)-[1,3,4]oxadiazole, cyclopropanecarboxylic acid {3-methoxy-4-[5-(5-methyl-3-phenyl-isoxazol-4-yl)-[1,3,4]oxadiazol-2-yl]-phenyl}-amide,
cyclopropanecarboxylic acid {3-methoxy-4-[5-(5-methyl-3-phenyl-isoxazol-4-yl)-[1,3,4]oxadiazol-2-yl]-phenyl}-methyl-amide,
(4-{5-[5-(2-cyclopropyl-ethyl)-3-phenyl-isoxazol-4-yl]-[1,3,4]oxadiazol-2-yl}-3-methoxy-phenyl)-cyclopropylmethyl-amine,
cyclopropylmethyl-{3-methoxy-4-[5-(5-methyl-3-phenyl-isoxazol-4-yl)-[1,3,4]oxadiazol-2-yl]-phenyl}-amine,
4-{5-[5-(2-cyclopropyl-ethyl)-3-phenyl-isoxazol-4-yl]-[1,3,4]oxadiazol-2-yl}-3-methoxy-phenylamine,
N-{3-methoxy-4-[5-(5-methyl-3-phenyl-isoxazol-4-yl)-[1,3,4]oxadiazol-2-yl]-phenyl}-bis-methanesulfonyl-amine,
N-{3-methoxy-4-[5-(5-methyl-3-phenyl-isoxazol-4-yl)-[1,3,4]oxadiazol-2-yl]-phenyl}-methanesulfonamide,
thiophene-3-carboxylic acid-{3-methoxy-4-[5-(5-methyl-3-phenyl-isoxazol-4-yl)-[1,3,4]oxadiazol-2-yl]-phenyl}-amide,
2-(4-fluoro-2-methoxy-phenyl)-5-(5-methyl-3-phenyl-isoxazol-4-yl)-[1,3,4]oxadiazole, 4-{3-methoxy-4-[5-(5-methyl-3-phenyl-isoxazol-4-yl)-[1,3,4]oxadiazol-2-yl]-phenyl}-thiomorpholine,
4-{3-methoxy-4-[5-(5-methyl-3-phenyl-isoxazol-4-yl)-[1,3,4]oxadiazol-2-yl]-phenyl}-thiomorpholine 1,1-dioxide,
1-{3-methoxy-4-[5-(5-methyl-3-phenyl-isoxazol-4-yl)-[1,3,4]oxadiazol-2-yl]-phenyl}-piperidin-4-ol,
2-(4-methanesulfonyl-phenyl)-5-(5-methyl-3-phenyl-isoxazol-4-yl)-[1,3,4]oxadiazole,
2-(3-methanesulfonyl-phenyl)-5-(5-methyl-3-phenyl-isoxazol-4-yl)-[1,3,4]oxadiazole,
5-(5-methyl-3-phenyl-isoxazol-4-yl)-2-(4-nitro-phenyl)-[1,3,4]oxadiazole,
2-(4-imidazol-1-yl-2-methoxy-phenyl)-5-(5-methyl-3-phenyl-isoxazol-4-yl)-[1,3,4]oxadiazole,
4-[5-(5-methyl-3-phenyl-isoxazol-4-yl)-[1,3,4]oxadiazol-2-yl]-phenylamine,
2-(4-fluoro-phenyl)-5-(5-methyl-3-phenyl-isoxazol-4-yl)-[1,3,4]oxadiazole,
4-{4-[5-(5-methyl-3-phenyl-isoxazol-4-yl)-[1,3,4]oxadiazol-2-yl]-phenyl}-thiomorpholine,
4-{4-[5-(5-methyl-3-phenyl-isoxazol-4-yl)-[1,3,4]oxadiazol-2-yl]-phenyl}-thiomorpholine 1,1-dioxide,
4-{4-[5-(5-methyl-3-phenyl-isoxazol-4-yl)-[1,3,4]oxadiazol-2-yl]-phenyl}-thiomorpholine 1-oxide,
(2S*,6R*)-2,6-dimethyl-4-{4-[5-(5-methyl-3-phenyl-isoxazol-4-yl)-[1,3,4]oxadiazol-2-yl]-phenyl}-morpholine,
2-(2-difluoromethoxy-phenyl)-5-(5-methyl-3-phenyl-isoxazol-4-yl)-[1,3,4]oxadiazole, 2-(5-methyl-3-phenyl-isoxazol-4-yl)-5-(2-trifluoromethoxy-phenyl)-[1,3,4]oxadiazole, 2-(3-fluoro-phenyl)-5-(5-methyl-3-phenyl-isoxazol-4-yl)-[1,3,4]oxadiazole,
2-(2-benzyloxy-phenyl)-5-(5-methyl-3-phenyl-isoxazol-4-yl)-[1,3,4]oxadiazole,
1-{4-[5-(5-methyl-3-phenyl-isoxazol-4-yl)-[1,3,4]oxadiazol-2-yl]-phenyl}-piperidine,
2-(2-methoxy-4-trifluoromethyl-phenyl)-5-(5-methyl-3-phenyl-isoxazol-4-yl)-[1,3,4]oxadiazole,
2-(5-methyl-3-phenyl-isoxazol-4-yl)-5-(4-trifluoromethyl-phenyl)-[1,3,4]oxadiazole,
2-(4-difluoromethoxy-phenyl)-5-(5-methyl-3-phenyl-isoxazol-4-yl)-[1,3,4]oxadiazole, 4-{3-methoxy-4-[5-(5-methyl-3-phenyl-isoxazol-4-yl)-[1,3,4]oxadiazol-2-yl]-phenyl}-thiomorpholine 1-oxide,
4-[5-(5-methyl-3-phenyl-isoxazol-4-yl)-[1,3,4]oxadiazol-2-yl]-benzonitrile,
2-[2-methoxy-4-(2-methyl-imidazol-1-yl)-phenyl]-5-(5-methyl-3-phenyl-isoxazol-4-yl)-[1,3,4]oxadiazole,
2-[4-(2-methyl-imidazol-1-yl)-phenyl]-5-(5-methyl-3-phenyl-isoxazol-4-yl)-[1,3,4]oxadiazole,
2-(5-ethyl-3-phenyl-isoxazol-4-yl)-5-(4-fluoro-2-methoxy-phenyl)-[1,3,4]oxadiazole,
2-(4-fluoro-2-methoxy-phenyl)-5-(5-isopropyl-3-phenyl-isoxazol-4-yl)-[1,3,4]oxadiazole,
thiophene-2-sulfonic acid {3-methoxy-4-[5-(5-methyl-3-phenyl-isoxazol-4-yl)-[1,3,4]oxadiazol-2-yl]-phenyl}-amide,
propane-2-sulfonic acid {3-methoxy-4-[5-(5-methyl-3-phenyl-isoxazol-4-yl)-[1,3,4]oxadiazol-2-yl]-phenyl}-amide,
{3-methoxy-4-[5-(5-methyl-3-phenyl-isoxazol-4-yl)-[1,3,4]oxadiazol-2-yl]-phenyl}-(tetrahydro-pyran-4-yl)-amine,
{3-methoxy-4-[5-(5-methyl-3-phenyl-isoxazol-4-yl)-[1,3,4]oxadiazol-2-yl]-phenyl}-(1-methyl-piperidin-4-yl)-amine,
1-{3-methoxy-4-[5-(5-methyl-3-phenyl-isoxazol-4-yl)-[1,3,4]oxadiazol-2-yl]-phenyl}-piperazine,
1-{3-methoxy-4-[5-(5-methyl-3-phenyl-isoxazol-4-yl)-[1,3,4]oxadiazol-2-yl]-phenyl}-4-methyl-piperazine,
4-{3-methoxy-4-[5-(5-methyl-3-phenyl-isoxazol-4-yl)-[1,3,4]oxadiazol-2-yl]-phenyl}-morpholine,
2-(5-cyclopropyl-3-phenyl-isoxazol-4-yl)-5-(2-methoxy-phenyl)-[1,3,4]oxadiazole,
4-[5-(5-Methyl-3-phenyl-isoxazol-4-yl)-[1,3,4]oxadiazol-2-yl]-benzoic acid methyl ester,
{3-methoxy-4-[5-(5-methyl-3-phenyl-isoxazol-4-yl)-[1,3,4]oxadiazol-2-yl]-phenyl}-dimethyl-amine,
2-(5-cyclopropyl-3-phenyl-isoxazol-4-yl)-5-(4-fluoro-2-methoxy-phenyl)-[1,3,4]oxadiazole,
2-(2,4-difluoro-phenyl)-5-(5-methyl-3-phenyl-isoxazol-4-yl)-[1,3,4]oxadiazole,
4-{4-[5-(5-cyclopropyl-3-phenyl-isoxazol-4-yl)-[1,3,4]oxadiazol-2-yl]-3-methoxy-phenyl}-morpholine,
N-cyclopropyl-4-[5-(5-methyl-3-phenyl-isoxazol-4-yl)-[1,3,4]oxadiazol-2-yl]-benzamide,
N-cyclopropylmethyl-4-[5-(5-methyl-3-phenyl-isoxazol-4-yl)-[1,3,4]oxadiazol-2-yl]-benzamide,
{4-[5-(5-methyl-3-phenyl-isoxazol-4-yl)-[1,3,4]oxadiazol-2-yl]-phenyl}-morpholin-4-yl-methanone,
4-[5-(5-methyl-3-phenyl-isoxazol-4-yl)-[1,3,4]oxadiazol-2-yl]-N-(tetrahydro-pyran-4-yl)-benzamide,
{4-[5-(5-cyclopropyl-3-phenyl-isoxazol-4-yl)-[1,3,4]oxadiazol-2-yl]-3-methoxy-phenyl}-(tetrahydro-pyran-4-yl)-amine,
2-(2,5-difluoro-phenyl)-5-(5-methyl-3-phenyl-isoxazol-4-yl)-[1,3,4]oxadiazole,
2-(2,3-difluoro-phenyl)-5-(5-methyl-3-phenyl-isoxazol-4-yl)-[1,3,4]oxadiazole,
2-(2-methoxy-4-[1,2,3]triazol-2-yl-phenyl)-5-(5-methyl-3-phenyl-isoxazol-4-yl)-[1,3,4]oxadiazole,
2-(2-methoxy-4-[1,2,3]triazol-1-yl-phenyl)-5-(5-methyl-3-phenyl-isoxazol-4-yl)-[1,3,4]oxadiazole,
2-(4,5-difluoro-2-methoxy-phenyl)-5-(5-methyl-3-phenyl-isoxazol-4-yl)-[1,3,4]oxadiazole,
{4-[5-(4-fluoro-2-methoxy-phenyl)-[1,3,4]oxadiazol-2-yl]-3-phenyl-isoxazol-5-ylmethyl}-methyl-amine,
N-{3-methoxy-4-[5-(5-methyl-3-phenyl-isoxazol-4-yl)-[1,3,4]oxadiazol-2-yl]-phenyl}-acetamide,
N-{3-methoxy-4-[5-(5-methyl-3-phenyl-isoxazol-4-yl)-[1,3,4]oxadiazol-2-yl]-phenyl}-propionamide,
2-(4-fluoro-2-methoxy-phenyl)-5-(5-methoxymethyl-3-phenyl-isoxazol-4-yl)-[1,3,4]oxadiazole,
{4-[5-(4-fluoro-2-methoxy-phenyl)-[1,3,4]oxadiazol-2-yl]-3-phenyl-isoxazol-5-yl}-methanol, 4-(4-{5-[3-(3-chloro-phenyl)-5-methyl-isoxazol-4-yl]-[1,3,4]oxadiazol-2-yl}-3-methoxy-phenyl)-morpholine,
4-{3-methoxy-4-[5-(3-phenyl-isoxazol-4-yl)-[1,3,4]oxadiazol-2-yl]-phenyl}-morpholine,
4-{4-[5-(3,5-diphenyl-isoxazol-4-yl)-[1,3,4]oxadiazol-2-yl]-3-methoxy-phenyl}-morpholine,
4-(4-{5-[3-(2-chloro-phenyl)-5-methyl-isoxazol-4-yl]-[1,3,4]oxadiazol-2-yl}-3-methoxy-phenyl)-morpholine,
4-(4-{5-[3-(4-fluoro-phenyl)-isoxazol-4-yl]-[1,3,4]oxadiazol-2-yl}-3-methoxy-phenyl)-morpholine,
4-(4-{5-[3-(4-fluoro-phenyl)-5-methyl-isoxazol-4-yl]-[1,3,4]oxadiazol-2-yl}-3-methoxy-phenyl)-morpholine,
4-{3-methoxy-4-[5-(5-methyl-3-pyridin-3-yl-isoxazol-4-yl)-[1,3,4]oxadiazol-2-yl]-phenyl}-morpholine,
4-(3-methoxy-4-{5-[5-methyl-3-(4-trifluoromethyl-phenyl)-isoxazol-4-yl]-[1,3,4]oxadiazol-2-yl}-phenyl)-morpholine,
4-(3-methoxy-4-{5-[5-methyl-3-(4-methyl-phenyl)-isoxazol-4-yl]-[1,3,4]oxadiazol-2-yl}-phenyl)-morpholine,
4-{4-[5-(5-chloro-3-phenyl-isoxazol-4-yl)-[1,3,4]oxadiazol-2-yl]-3-methoxy-phenyl}-morpholine,
{4-[5-(2-methoxy-4-morpholin-4-yl-phenyl)-[1,3,4]oxadiazol-2-yl]-3-phenyl-isoxazol-5-yl}-dimethyl-amine,
4-{4-[5-(2-methoxy-4-morpholin-4-yl-phenyl)-[1,3,4]oxadiazol-2-yl]-3-phenyl-isoxazol-5-yl}-morpholine,
4-(4-{5-[3-(3-fluoro-phenyl)-5-methyl-isoxazol-4-yl]-[1,3,4]oxadiazol-2-yl}-3-methoxy-phenyl)-morpholine,
4-(4-{5-[3-(4-chloro-phenyl)-5-methyl-isoxazol-4-yl]-[1,3,4]oxadiazol-2-yl}-3-methoxy-phenyl)-morpholine,
4-{3-methoxy-4-[5-(5-methyl-3-thiophen-2-yl-isoxazol-4-yl)-[1,3,4]oxadiazol-2-yl]-phenyl}-morpholine,
ethyl-{4-[5-(2-methoxy-4-morpholin-4-yl-phenyl)-[1,3,4]oxadiazol-2-yl]-3-phenyl-isoxazol-5-yl}-amine,
4,4-difluoro-1-{4-[5-(5-methyl-3-phenyl-isoxazol-4-yl)-[1,3,4]oxadiazol-2-yl]-phenyl}-piperidine,
4-{3-methoxy-4-[5-(3-phenyl-5-pyrazol-1-yl-isoxazol-4-yl)-[1,3,4]oxadiazol-2-yl]-phenyl}-morpholine,
4-{2-fluoro-5-methoxy-4-[5-(5-methyl-3-phenyl-isoxazol-4-yl)-[1,3,4]oxadiazol-2-yl]-phenyl}-morpholine,
4-[5-(2-methoxy-4-morpholin-4-yl-phenyl)-[1,3,4]oxadiazol-2-yl]-3-phenyl-isoxazole-5-carbonitrile,
4-{2-fluoro-5-methoxy-4-[5-(5-methyl-3-phenyl-isoxazol-4-yl)-[1,3,4]oxadiazol-2-yl]-phenyl}-thiomorpholine,
4-{2-fluoro-5-methoxy-4-[5-(5-methyl-3-phenyl-isoxazol-4-yl)-[1,3,4]oxadiazol-2-yl]-phenyl}-thiomorpholine 1,1-dioxide,
2-(5-methyl-3-phenyl-isoxazol-4-yl)-5-(2,4,5-trifluoro-phenyl)-[1,3,4]oxadiazole,
4-{2,5-difluoro-4-[5-(5-methyl-3-phenyl-isoxazol-4-yl)-[1,3,4]oxadiazol-2-yl]-phenyl}-thiomorpholine,
4-{2,5-difluoro-4-[5-(5-methyl-3-phenyl-isoxazol-4-yl)-[1,3,4]oxadiazol-2-yl]-phenyl}-thiomorpholine 1,1-dioxide,
4-{3-methoxy-4-[5-(5-methyl-3-thiophen-3-yl-isoxazol-4-yl)-[1,3,4]oxadiazol-2-yl]-phenyl}-morpholine,
(2-methoxy-ethyl)-{3-methoxy-4-[5-(5-methyl-3-phenyl-isoxazol-4-yl)-[1,3,4]oxadiazol-2-yl]-phenyl}-amine,
{2-fluoro-5-methoxy-4-[5-(5-methyl-3-phenyl-isoxazol-4-yl)-[1,3,4]oxadiazol-2-yl]-phenyl}-(2-methylsulfanyl-ethyl)-amine,
{2-fluoro-5-methoxy-4-[5-(5-methyl-3-phenyl-isoxazol-4-yl)-[1,3,4]oxadiazol-2-yl]-phenyl}-(2-methanesulfonyl-ethyl)-amine,
1-(2-{2-fluoro-5-methoxy-4-[5-(5-methyl-3-phenyl-isoxazol-4-yl)-[1,3,4]oxadiazol-2-yl]-phenylamino}-ethyl)-pyrrolidin-2-one,
2-{2-fluoro-5-methoxy-4-[5-(5-methyl-3-phenyl-isoxazol-4-yl)-[1,3,4]oxadiazol-2-yl]-phenylamino}-ethanol,
rac-{2-fluoro-5-methoxy-4-[5-(5-methyl-3-phenyl-isoxazol-4-yl)-[1,3,4]oxadiazol-2-yl]-phenyl}-(tetrahydro-furan-2-ylmethyl)-amine,
{2-fluoro-5-methoxy-4-[5-(5-methyl-3-phenyl-isoxazol-4-yl)-[1,3,4]oxadiazol-2-yl]-phenyl}-pyridin-2-ylmethyl-amine,
{2-fluoro-5-methoxy-4-[5-(5-methyl-3-phenyl-isoxazol-4-yl)-[1,3,4]oxadiazol-2-yl]-phenyl}-(2-pyrrolidin-1-yl-ethyl)-amine,
1-(2-{2-fluoro-5-methoxy-4-[5-(5-methyl-3-phenyl-isoxazol-4-yl)-[1,3,4]oxadiazol-2-yl]-phenylamino}-ethyl)-imidazolidin-2-one,
N-{3-methoxy-4-[5-(5-methyl-3-phenyl-isoxazol-4-yl)-[1,3,4]oxadiazol-2-yl]-phenyl}-formamide and
N'-{2-fluoro-5-methoxy-4-[5-(5-methyl-3-phenyl-isoxazol-4-yl)-[1,3,4]oxadiazol-2-yl]-phenyl}-N,N-dimethyl-ethane-1,2-diamine.

In a certain embodiment, the compounds of the invention are those compounds, wherein $R^2$ is heteroaryl, which is optionally substituted by one or more substituents selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —$NR^aR^b$, —C(O)—$NR^aR^b$, —C(O)-heterocyclyl, benzyloxy, heterocyclyl optionally substituted by hydroxy, halogen or lower alkyl, and heteroaryl optionally substituted by lower alkyl, and the other definitions are as above, for example the following compounds
2-chloro-3-[5-(5-methyl-3-phenyl-isoxazol-4-yl)-[1,3,4]oxadiazol-2-yl]-pyridine,
8-[5-(5-methyl-3-phenyl-isoxazol-4-yl)-[1,3,4]oxadiazol-2-yl]-quinoline,
2-[5-(5-methyl-3-phenyl-isoxazol-4-yl)-[1,3,4]oxadiazol-2-yl]-pyridine,
5-[5-(5-methyl-3-phenyl-isoxazol-4-yl)-[1,3,4]oxadiazol-2-yl]-1H-benzoimidazole,
5-[5-(5-methyl-3-phenyl-isoxazol-4-yl)-[1,3,4]oxadiazol-2-yl]-1,3-dihydro-benzoimidazol-2-one,
4-[5-(5-methyl-3-phenyl-isoxazol-4-yl)-[1,3,4]oxadiazol-2-yl]-pyridine,
4-[5-(5-methyl-3-phenyl-isoxazol-4-yl)-[1,3,4]oxadiazol-2-yl]-quinoline,
5-[5-(5-methyl-3-phenyl-isoxazol-4-yl)-[1,3,4]oxadiazol-2-yl]-pyridin-2-ylamine,
1,3-dimethyl-5-[5-(5-methyl-3-phenyl-isoxazol-4-yl)-[1,3,4]oxadiazol-2-yl]-1,3-dihydro-benzoimidazol-2-one,
5-[5-(5-isopropyl-3-phenyl-isoxazol-4-yl)-[1,3,4]oxadiazol-2-yl]-1,3-dimethyl-1,3-dihydro-benzoimidazol-2-one,
2-chloro-4-[5-(5-methyl-3-phenyl-isoxazol-4-yl)-[1,3,4]oxadiazol-2-yl]-pyridine,
4-{4-[5-(5-methyl-3-phenyl-isoxazol-4-yl)-[1,3,4]oxadiazol-2-yl]-pyridin-2-yl}-morpholine,
5-[5-(5-methyl-3-phenyl-isoxazol-4-yl)-[1,3,4]oxadiazol-2-yl]-1H-indole, 2-methoxy-3-[5-(5-methyl-3-phenyl-isoxazol-4-yl)-[1,3,4]oxadiazol-2-yl]-pyridine,
2-chloro-6-methoxy-3-[5-(5-methyl-3-phenyl-isoxazol-4-yl)-[1,3,4]oxadiazol-2-yl]-pyridine,
2,6-dimethoxy-3-[5-(5-methyl-3-phenyl-isoxazol-4-yl)-[1,3,4]oxadiazol-2-yl]-pyridine,
2-(5-Methyl-3-phenyl-isoxazol-4-yl)-5-thiophen-2-yl-[1,3,4]oxadiazole,
2-(5-methyl-3-phenyl-isoxazol-4-yl)-5-thiophen-3-yl-[1,3,4]oxadiazole,
4-[5-(5-methyl-3-phenyl-isoxazol-4-yl)-[1,3,4]oxadiazol-2-yl]-1H-benzoimidazole,
4-{5-[5-(5-methyl-3-phenyl-isoxazol-4-yl)-[1,3,4]oxadiazol-2-yl]-pyridin-2-yl}-morpholine, 2-{5-[5-(5-methyl-3-phenyl-isoxazol-4-yl)-[1,3,4]oxadiazol-2-yl]-pyridin-2-ylamino}-ethanol,
4-{5-[5-(5-methyl-3-phenyl-isoxazol-4-yl)-[1,3,4]oxadiazol-2-yl]-pyridin-2-yl}-thiomorpholine,
{5-[5-(5-methyl-3-phenyl-isoxazol-4-yl)-[1,3,4]oxadiazol-2-yl]-pyridin-2-yl}-(tetrahydro-pyran-4-yl)-amine,
5'-[5-(5-methyl-3-phenyl-isoxazol-4-yl)-[1,3,4]oxadiazol-2-yl]-3,4,5,6-tetrahydro-2H-[1,2']bipyridinyl-4-ol,
4-{5-[5-(5-methyl-3-phenyl-isoxazol-4-yl)-[1,3,4]oxadiazol-2-yl]-pyridin-2-yl}-thiomorpholine 1,1-dioxide and
4-{6-[5-(5-methyl-3-phenyl-isoxazol-4-yl)-[1,3,4]oxadiazol-2-yl]-pyridin-3-yl}-morpholine.

In a certain embodiment, the compounds of the invention are those compounds, wherein $R^2$ is heterocyclyl, which is optionally substituted by one or more substituents selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —$NR^aR^b$, —C(O)—$NR^aR^b$, —C(O)-heterocyclyl, benzyloxy, heterocyclyl optionally substituted by hydroxy, halogen or lower alkyl, and heteroaryl optionally substituted by lower alkyl, and the other definitions are as above.

In a certain embodiment, the compounds of the invention are those compounds, wherein $R^2$ is pyridinyl optionally substituted by halogen, lower alkoxy, heterocyclyl or $NR^aR^b$, wherein $R^a$ and $R^b$ are as defined above, for example the following compounds:
2-chloro-3-[5-(5-methyl-3-phenyl-isoxazol-4-yl)-[1,3,4]oxadiazol-2-yl]-pyridine,
2-[5-(5-methyl-3-phenyl-isoxazol-4-yl)-[1,3,4]oxadiazol-2-yl]-pyridine,
4-[5-(5-methyl-3-phenyl-isoxazol-4-yl)-[1,3,4]oxadiazol-2-yl]-pyridine,
5-[5-(5-methyl-3-phenyl-isoxazol-4-yl)-[1,3,4]oxadiazol-2-yl]-pyridin-2-ylamine,
2-chloro-4-[5-(5-methyl-3-phenyl-isoxazol-4-yl)-[1,3,4]oxadiazol-2-yl]-pyridine,
4-{4-[5-(5-methyl-3-phenyl-isoxazol-4-yl)-[1,3,4]oxadiazol-2-yl]-pyridin-2-yl}-morpholine,
2-methoxy-3-[5-(5-methyl-3-phenyl-isoxazol-4-yl)-[1,3,4]oxadiazol-2-yl]-pyridine,
2-chloro-6-methoxy-3-[5-(5-methyl-3-phenyl-isoxazol-4-yl)-[1,3,4]oxadiazol-2-yl]-pyridine,
2,6-dimethoxy-3-[5-(5-methyl-3-phenyl-isoxazol-4-yl)-[1,3,4]oxadiazol-2-yl]-pyridine,
4-{5-[5-(5-methyl-3-phenyl-isoxazol-4-yl)-[1,3,4]oxadiazol-2-yl]-pyridin-2-yl}-morpholine,
[5-(5-methyl-3-phenyl-isoxazol-4-yl)-[1,3,4]oxadiazol-2-yl]-pyridin-2-ylamino}-ethanol,
4-{5-[5-(5-methyl-3-phenyl-isoxazol-4-yl)-[1,3,4]oxadiazol-2-yl]-pyridin-2-yl}-thiomorpholine,
{5-[5-(5-methyl-3-phenyl-isoxazol-4-yl)-[1,3,4]oxadiazol-2-yl]-pyridin-2-yl}-(tetrahydro-pyran-4-yl)-amine,
5'-[5-(5-methyl-3-phenyl-isoxazol-4-yl)-[1,3,4]oxadiazol-2-yl]-3,4,5,6-tetrahydro-2H-[1,2']bipyridinyl-4-ol,
4-{5-[5-(5-methyl-3-phenyl-isoxazol-4-yl)-[1,3,4]oxadiazol-2-yl]-pyridin-2-yl}-thiomorpholine 1,1-dioxide and 4-{6-[5-(5-methyl-3-phenyl-isoxazol-4-yl)-[1,3,4]oxadiazol-2-yl]-pyridin-3-yl}-morpholine.

In a certain embodiment, the compounds of the invention are those compounds, wherein $R^2$ is quinolinyl, for example the following compounds:
8-[5-(5-methyl-3-phenyl-isoxazol-4-yl)-[1,3,4]oxadiazol-2-yl]-quinoline and
4-[5-(5-methyl-3-phenyl-isoxazol-4-yl)-[1,3,4]oxadiazol-2-yl]-quinoline.

In a certain embodiment, the compounds of the invention are those compounds, wherein $R^2$ is 1-H-benzoimidazol-5-yl, 1,3-dihydro-benzolimidazol-2-on-5-yl or 1,3-dimethyl-1,3-dihydro-benzoimidazol-2-on-5-yl, for example the following compounds: 5-[5-(5-methyl-3-phenyl-isoxazol-4-yl)-[1,3,4]oxadiazol-2-yl]-1H-benzoimidazole, 5-[5-(5-methyl-3-phenyl-isoxazol-4-yl)-[1,3,4]oxadiazol-2-yl]-1,3-dihydro-benzoimidazol-2-one, 1,3-dimethyl-5-[5-(5-methyl-3-phenyl-isoxazol-4-yl)-[1,3,4]oxadiazol-2-yl]-1,3-dihydro-benzoimidazol-2-one and 5-[5-(5-isopropyl-3-phenyl-isoxazol-4-yl)-[1,3,4]oxadiazol-2-yl]-1,3-dimethyl-1,3-dihydro-benzoimidazol-2-one.

The present compounds of formula I and their pharmaceutically acceptable salts can be prepared by methods known in the art, for example, by processes described below, which processes comprise reacting a compound of formula II

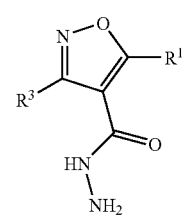

with a compound of formula III

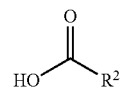

in the presence of phosphorous oxychloride to give a compound of formula

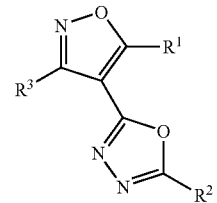

wherein $R^1$, $R^2$ and $R^3$ are as described above, and, if desired, converting a compound of formula I into a pharmaceutically acceptable salt.

The following schemes describe the processes for preparation of compounds of formula I in more detail. All starting materials are known compounds or can be prepared according to methods known in the art.

Scheme 1

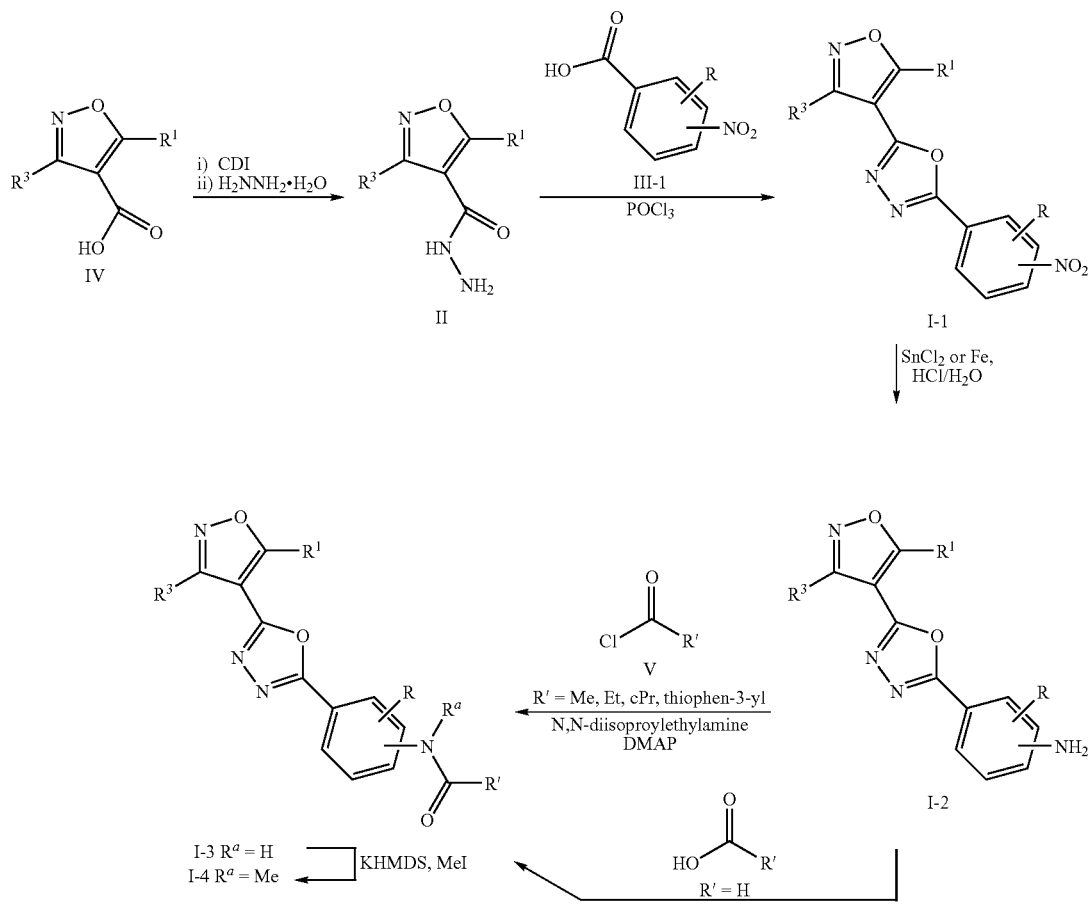

R is halogen, cyano, lower alkyl, lower alkoxy, lower alkoxy substituted by halogen, lower alkyl substituted by halogen, C(O)O-lower alkyl, lower alkylsulfonyl, —C(O)—NR$^a$R$^b$, —C(O)-heterocyclyl, benzyloxy, heterocyclyl optionally substituted by hydroxy, halogen or lower alkyl, or is heteroaryl optionally substituted by lower alkyl and the other definitions are as above.

In accordance with scheme 1, a compound of formula I may be prepared as follows: Carboxylic acid IV is heated in a suitable solvent, for example THF, with 1,1'-carbonyl-diimidazole before hydrazine-monohydrate was added at 0° C. The obtained carboxylic acid hydrazide II was heated with a corresponding acid III-1 in phosphorous oxychloride affording the oxadiazole I-1 which can be further transformed with tin(II) chloride or iron powder in a mixture of ethanol and aqueous HCl at elevated temperature to the corresponding phenyl-amines I-2. Amides I-3 can be obtained by stirring phenylamines I-2 with N,N-diisopropylethylamine, DMAP and corresponding carboxylic acid chloride V in a suitable solvent, for example THF, at ambient or elevated temperature or can be obtained by heating with a corresponding acid, for example formic acid. Amide-alkylation towards I-4 is proceeded by deprotonation of amides I-3 with KHMDS in a suitable solvent, for example THF, followed by addition of methyliodide at ambient temperature.

Scheme 2

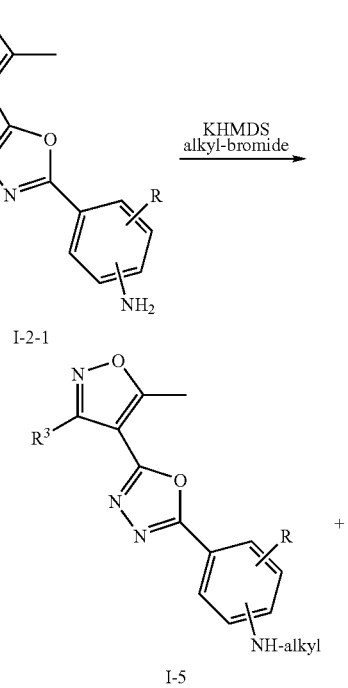

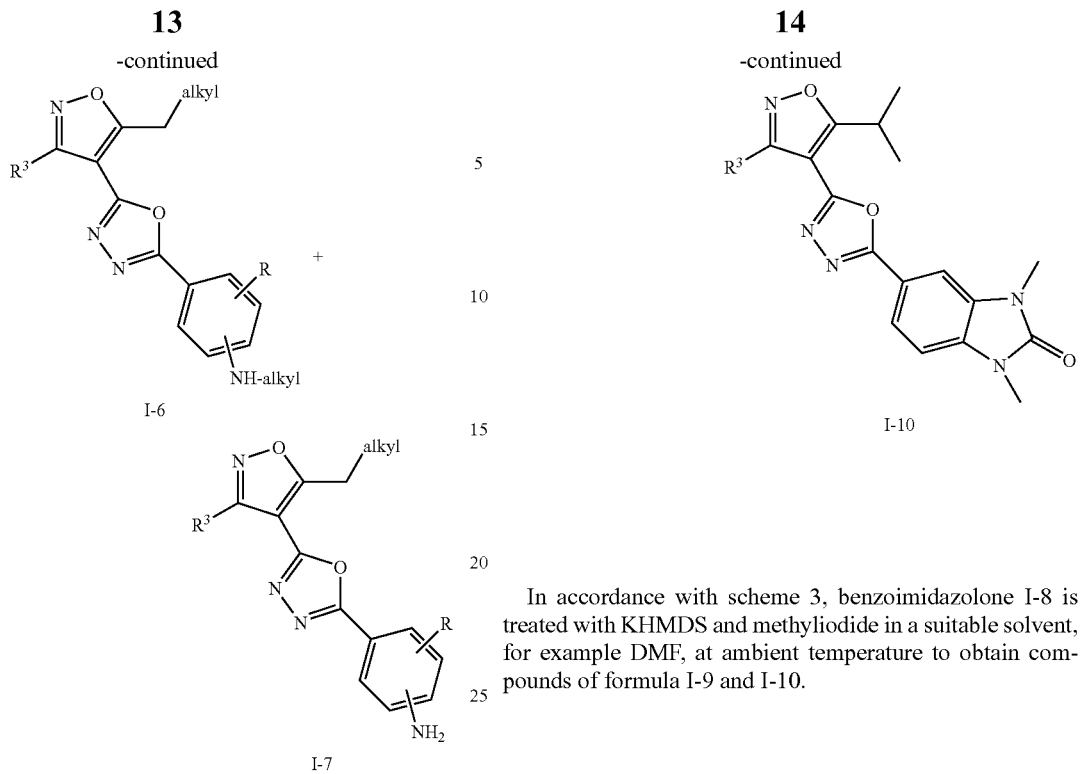

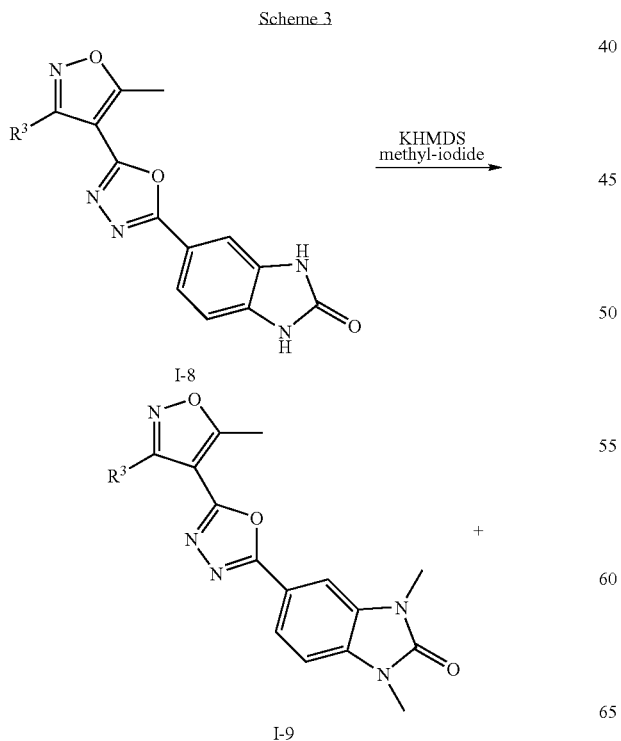

R is as defined as in scheme 1 and the other definitions are as described above.

In accordance with scheme 2, a phenyl-amine I-2 is treated with KHMDS and an appropriate alkyl-bromide, for example cyclopropylmethyliodide, in a suitable solvent, for example THF, to obtain compounds of formula I-5, I-6 and I-7.

In accordance with scheme 3, benzoimidazolone I-8 is treated with KHMDS and methyliodide in a suitable solvent, for example DMF, at ambient temperature to obtain compounds of formula I-9 and I-10.

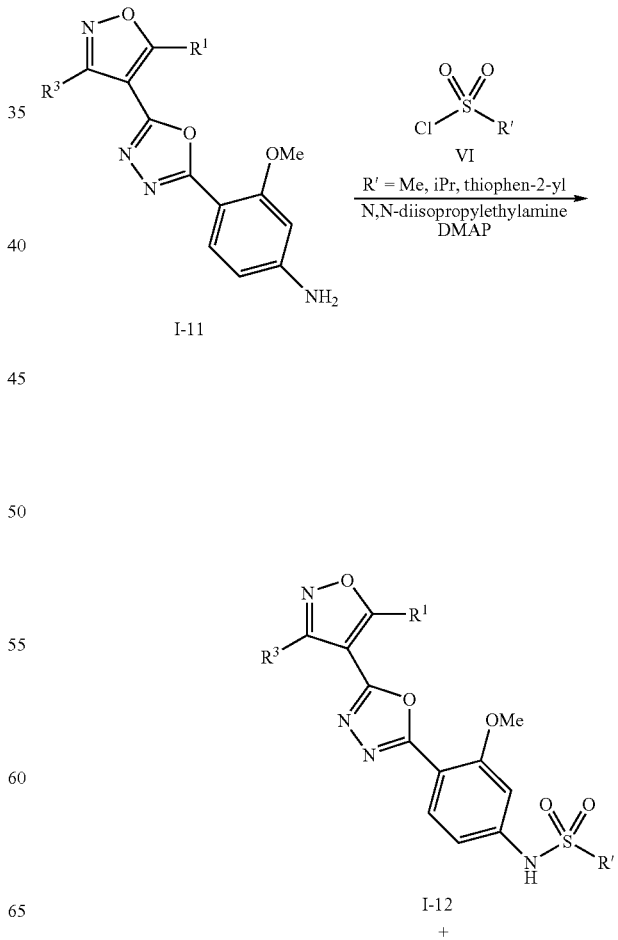

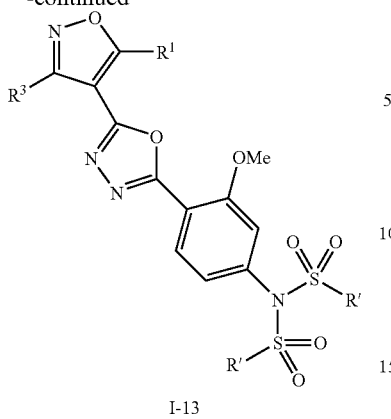

I-13

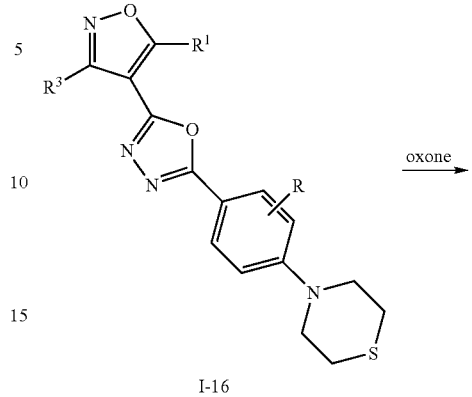

Scheme 6

I-16

In accordance with scheme 4, phenyl-amine I-11 is treated with corresponding sulfonyl chloride VI in the presence of N,N-diisopropylethylamine and DMAP in a suitable solvent, for example THF, at elevated temperature to obtain compounds of formula I-12 and I-13.

Scheme 5

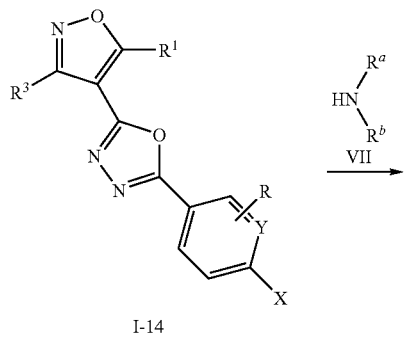

I-14

Y = CH, N
X = F, Cl

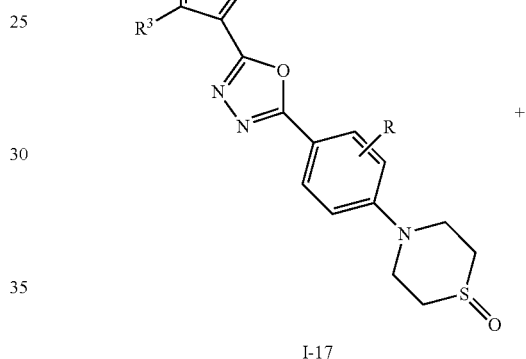

I-17

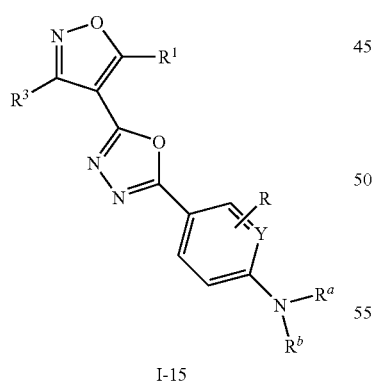

I-15

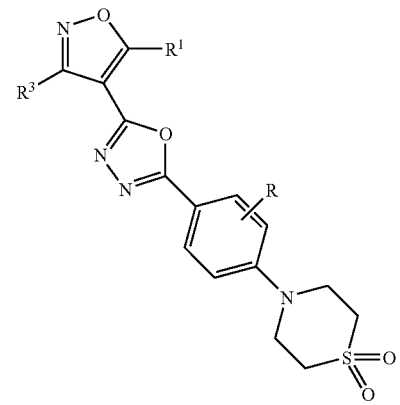

I-18

R is as described as for scheme 1 and the other definitions are as above.

In accordance with scheme 5, phenyl fluoride or chloropyridine I-14 is treated with a corresponding amine VII in a suitable solvent, for example DMSO, at elevated temperature to obtain compounds of formula I-15.

R is as described as for scheme 1 and the other definitions are as above.

In accordance with scheme 6, thiomorpholine I-16 is treated with a corresponding oxidation agent, for example oxone or potassium monopersulfate, in a suitable solvent, for example dichloromethane, at elevated temperature to obtain compounds of formula I-17 and I-18.

Scheme 7

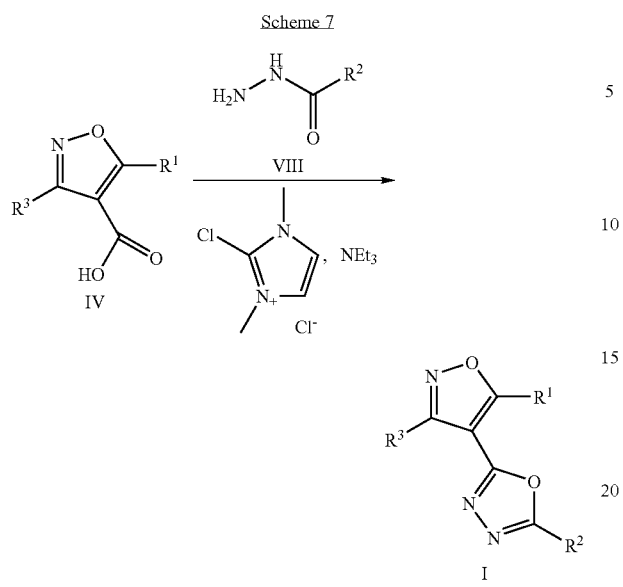

In accordance with scheme 7, carboxylic acid IV is treated with a corresponding carboxylic acid hydrazide VIII in presence of a dehydrating agent, for example 2-chloro-1,3-dimethylimidazolium chloride, in a suitable solvent, for example dichloromethane, at ambient temperature to obtain compounds of formula I.

Scheme 8

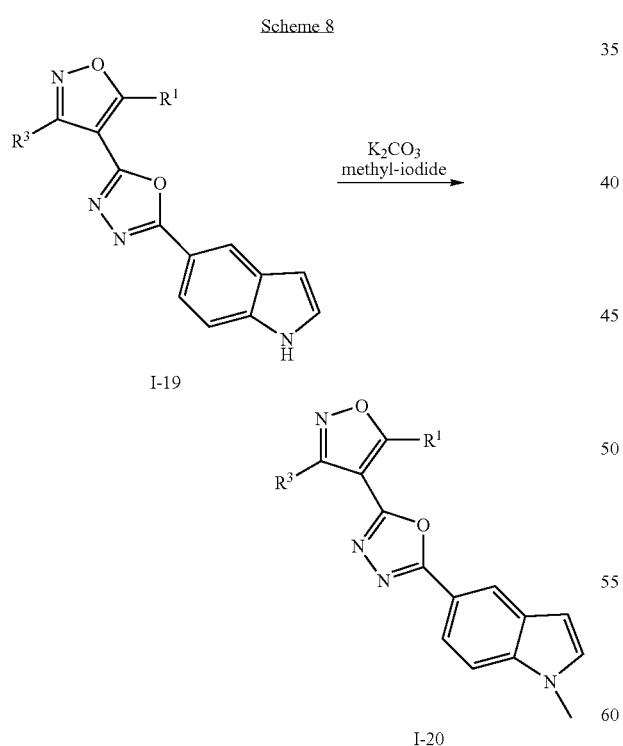

In accordance with scheme 8, indole I-19 is treated with potassium carbonate and methyliodide in a suitable solvent, for example DMF, at ambient temperature to obtain a compound of formula I-20.

Scheme 9

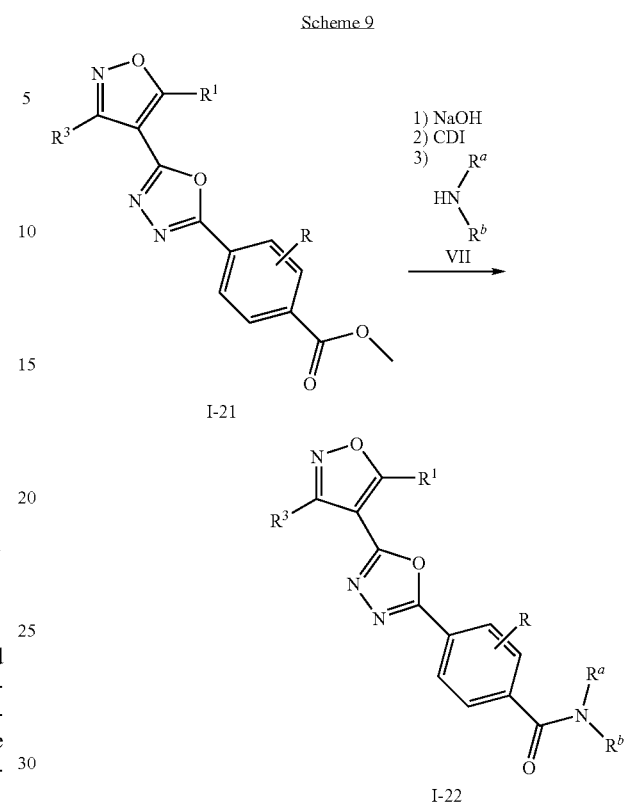

R is as described as for scheme 1 and the other definitions are as above.

In accordance with scheme 9, carboxylic ester I-21 is hydrolysed under standard conditions and the resulting carboxylic acid is activated with a suitable agent, for example 1,1'-carbonyl-diimidazole before treated with a corresponding amine VII in a suitable solvent, for example tetrahydrofuran, at elevated temperature to obtain amides of formula I-22.

Scheme 10

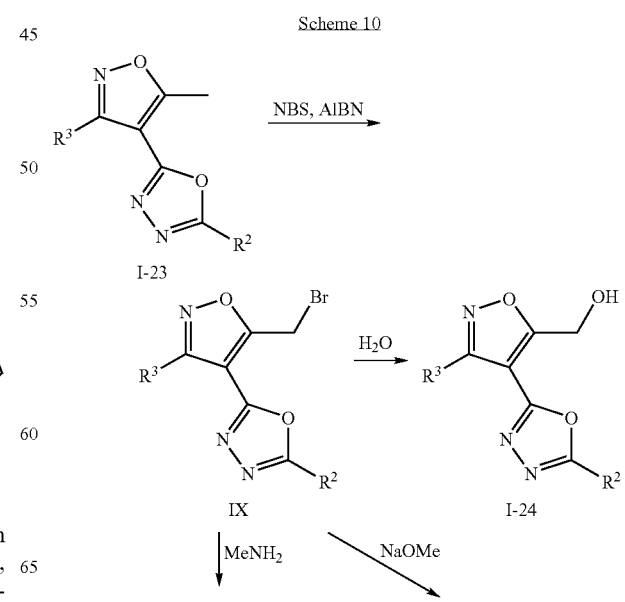

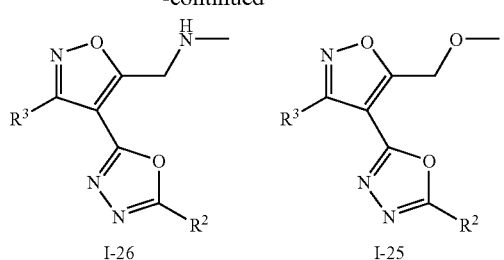

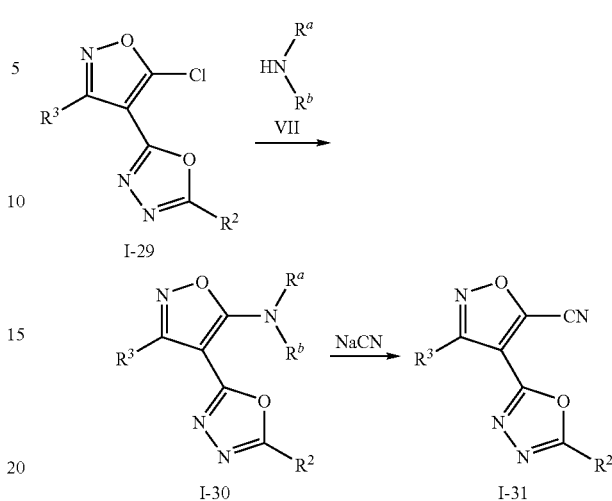

In accordance with scheme 10, methyl isoxazole I-23 is halogenated to a compound of formula IX under standard conditions using N-bromosuccinimde and 2,2'-azobis(2-methylpropionitrile) followed by treatment with (1) water in a suitable solvent, for example DMSO, at elevated temperature to obtain alcohols of formula I-24; (2) sodium methanolate in a suitable solvent, for example methanol, at ambient temperature to obtain ethers of formula I-25; or (3) amines, for example methylamine, in presence of a base, for example potassium carbonate, in a suitable solvent, for example tetrahydrofuran, at elevated temperature to obtain amines of formula I-26.

In accordance with scheme 12, 5-chloroisoxazole I-29 is treated with corresponding amines VII without or with a base, for example potassium carbonate, in a suitable solvent, for example DMSO, at ambient temperature to obtain compounds of formula I-30 and then with sodium cyanide in a suitable solvent, for example DMF, at ambient temperature to obtain 5-cyano-isoxazoles of formula I-31.

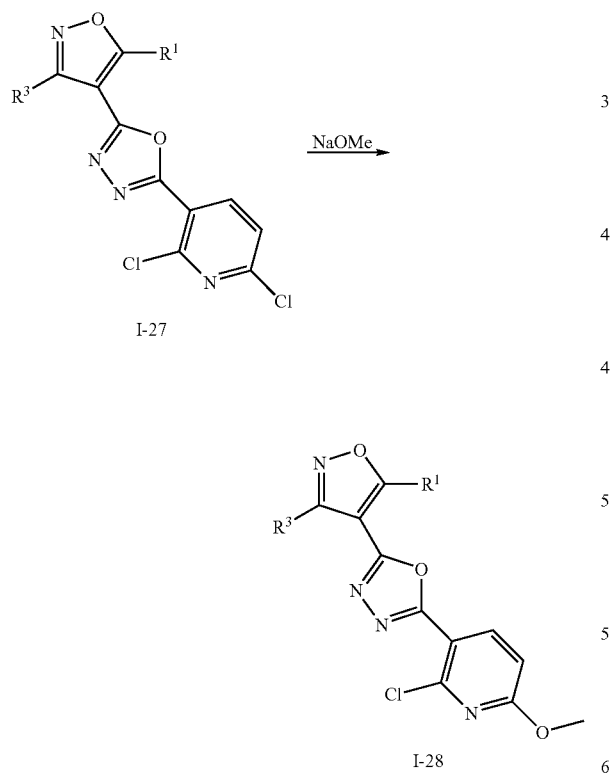

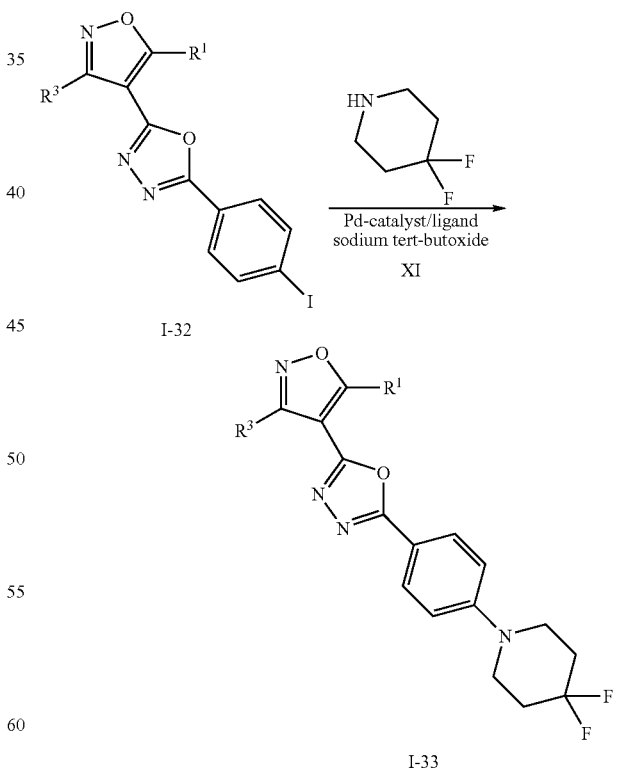

In accordance with scheme 11, dichloropyridine I-27 is treated with sodium methanolate in a suitable solvent, for example tetrahydrofuran, at ambient temperature to obtain compounds of formula I-28.

In accordance with scheme 13, phenyl-iodide I-32 is treated with 4,4-difluoropiperidine in the presence of tris (dibenzylideneacetone)di-palladium (0) chloroform complex/2-(dicyclohexylphosphino)biphenyl (XI) and sodium tert-butoxide as a base in a suitable solvent, for example toluene, at elevated temperature to obtain compounds of formula I-33.

Scheme 14

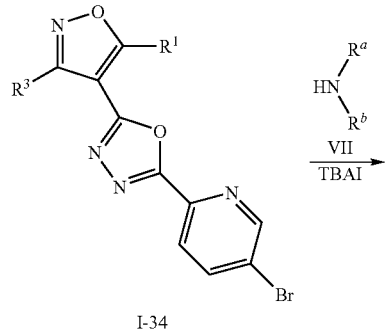

In accordance with scheme 14, bromo-pyridine I-34 is treated with a corresponding amine VII in presence of tetrabutylammonium iodide at elevated temperature to obtain compounds of formula I-35.

As mentioned earlier, the compounds of formula I and their pharmaceutically usable salts possess valuable pharmacological properties. Compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10-10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 400 nM or less. In a preferred embodiment the compounds of the invention are binding selective for the α5 subunit relative to the α1, α2 and α3 subunit.

| Example | Ki[nM] hα5 |
|---|---|
| 1 | 400 |
| 2 | 234 |
| 3 | 391 |
| 4 | 16.4 |
| 5 | 31.1 |
| 6 | 146 |
| 7 | 40.6 |
| 8 | 58.2 |
| 9 | 286 |
| 10 | 31.7 |
| 11 | 171 |
| 12 | 106 |
| 13 | 7.5 |
| 14 | 31.0 |
| 15 | 14.8 |
| 16 | 7.7 |
| 17 | 48.8 |
| 18 | 124 |
| 19 | 11.6 |
| 20 | 20.5 |
| 21 | 85 |
| 22 | 6.1 |
| 23 | 18.3 |
| 24 | 39.6 |
| 25 | 30.9 |
| 26 | 10.2 |
| 27 | 22.1 |
| 28 | 3.2 |
| 29 | 6.0 |
| 30 | 226 |
| 31 | 199 |
| 32 | 240 |
| 33 | 7.5 |
| 34 | 7.9 |
| 35 | 31.2 |
| 36 | 134 |
| 37 | 22.9 |
| 38 | 19.7 |
| 39 | 16.7 |
| 40 | 179 |
| 41 | 32.5 |
| 42 | 141 |
| 43 | 131 |
| 44 | 88.9 |
| 45 | 100 |
| 46 | 255 |
| 47 | 46.9 |
| 48 | 38.9 |
| 49 | 39.7 |
| 50 | 250 |
| 51 | 128 |
| 52 | 58.9 |
| 53 | 2.3 |
| 54 | 88.4 |

| Example | Ki[nM] hα5 |
|---|---|
| 55 | 324 |
| 56 | 2.2 |
| 57 | 84.2 |
| 58 | 13.9 |
| 59 | 30.7 |
| 60 | 96.0 |
| 61 | 17.7 |
| 62 | 42.8 |
| 63 | 42.8 |
| 64 | 4.2 |
| 65 | 15.3 |
| 66 | 13.4 |
| 67 | 15.5 |
| 68 | 4.2 |
| 69 | 8.1 |
| 70 | 262.2 |
| 71 | 289.1 |
| 72 | 12.0 |
| 73 | 11.9 |
| 74 | 134.3 |
| 75 | 128.9 |
| 76 | 189.5 |
| 77 | 2.1 |
| 78 | 42.1 |
| 79 | 234.8 |
| 80 | 468.6 |
| 81 | 86.0 |
| 82 | 3.7 |
| 83 | 162.8 |
| 84 | 224.8 |
| 85 | 20.6 |
| 86 | 4.8 |
| 87 | 43.8 |
| 88 | 338.8 |
| 89 | 4.6 |
| 90 | 4.8 |
| 91 | 111.6 |
| 92 | 293.0 |
| 93 | 22.8 |
| 94 | 19.3 |
| 95 | 44.5 |
| 96 | 15.3 |
| 97 | 105.0 |
| 98 | 49.0 |
| 99 | 95.8 |
| 100 | 24.0 |
| 101 | 14.5 |
| 102 | 146.3 |
| 103 | 47.6 |
| 104 | 12.1 |
| 105 | 27.1 |
| 106 | 164.8 |
| 107 | 31.1 |
| 108 | 11.3 |
| 109 | 2.2 |
| 110 | 19.5 |
| 111 | 4.9 |
| 112 | 31.2 |
| 113 | 7.4 |
| 114 | 6.0 |
| 115 | 131.0 |
| 116 | 4.5 |
| 117 | 2.0 |
| 118 | 149.0 |
| 119 | 24.3 |
| 120 | 13.5 |
| 121 | 114.6 |
| 122 | 139.5 |
| 123 | 14.4 |
| 124 | 8.2 |
| 125 | 26.8 |
| 126 | 4.5 |
| 127 | 1.7 |
| 128 | 4.2 |
| 129 | 2.5 |
| 130 | 10.5 |
| 131 | 21.2 |
| 132 | 8.6 |
| 133 | 12.8 |
| 134 | 5.8 |
| 135 | 9.4 |
| 136 | 15.3 |
| 137 | 24.5 |
| 138 | 31.0 |
| 139 | 16.4 |
| 140 | 23.5 |
| 141 | 17.7 |
| 142 | 17.2 |

The invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions of the invention can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the invention have high affinity and selectivity for GABA A α5 receptor binding sites. The invention provides a method for enhancing cognition, which comprises administering to an individual a therapeutically effective amount of a compound of formula I or a pharmaceutically acceptable salt thereof. The invention also provides a method for treating Alzheimer's disease, which comprises administering to an individual a therapeutically effective amount of a compound of formula I or a pharmaceutically acceptable salt thereof.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention also can be administered rectally, for example, in the form of suppositories, or parenterally, for example, in the form of injectable solutions.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-142 are provided for illustration of the invention. They should not be considered as limiting the scope of the invention, but merely as being representative thereof.

EXAMPLE 1

2-(5-Methyl-3-phenyl-isoxazol-4-yl)-5-phenyl-[1,3,4]oxadiazole a) 5-Methyl-3-phenyl-isoxazole-4-carboxylic acid hydrazide To a solution of 5-methyl-3-phenyl-isoxazole-4-carboxylic acid (5.00 g, 24.6 mmol) in THF (50 mL) was added in one portion 1,1'-carbonyl-diimidazole (4.39 g, 27.1 mmol). After stirring for 15 min at ambient temperature the solution was warmed to 70° C. and stirred for 30 min at this temperature. After the solution was cooled to 0° C. hydrazine monohydrate (2.4 mL, 49.0 mmol) was added over a period of 2 min while the temperature raised to 15° C. The resulting suspension was stirred for 30 min at 0° C. After addition of 20 mL heptane the suspension was stirred for 15 min at 0° C. and filtered off. Washing with water and drying afforded the title compound (4.52 g, 85%) as a white solid. MS: m/e=218.2 [M+H]$^+$.

b) 2-(5-Methyl-3-phenyl-isoxazol-4-yl)-5-phenyl-[1,3,4]oxadiazole

To a solution of ethyl benzimidate hydrochloride (376 mg; 2.03 mmol) in ethanol (4 mL) was added at 0° C. sodium ethoxide (2.72 M in ethanol, 355 L, 0.99 mmol) and stirred for 15 min. The suspension was filtered off and 5-methyl-3-phenyl-isoxazole-4-carboxylic acid hydrazide (200 mg, 0.92 mmol) was added and stirred for 90 h at 70° C. The reaction mixture was suspended in dioxane (4 mL) and heated in the microwave for 30 min at 180° C. Concentration and then purification by chromatography (SiO$_2$, heptane:ethyl acetate=95:5 to 60:40) afforded the title compound (163 mg, 29%) as a white solid. MS: m/e=304.2 [M+H]$^+$.

EXAMPLE 2

2-(5-Methyl-3-phenyl-isoxazol-4-yl)-5-o-tolyl-[1,3,4]oxadiazole

To a suspension of 5-methyl-3-phenyl-isoxazole-4-carboxylic acid hydrazide (200 mg, 0.92 mmol) in phosphorus oxychloride (1.68 mL, 18.4 mmol) was added o-toluic acid (188 mg, 1.38 mmol) and was stirred for 30 min at ambient temperature. The suspension was heated for 2 h at 90° C. whereupon it became homogeneous. After cooling to ambient temperature it was then poured onto a mixture of ethyl acetate (20 mL) and aqueous sodium carbonate (saturated, 20 mL). The aqueous phase was then separated and extracted with ethyl acetate (20 mL). The combined organic extracts were then washed with aqueous sodium carbonate and brine. Concentration and trituration in tert-butylmethylether (3 mL) afforded the title compound (99 mg, 34%) as a white solid. MS: m/e=318.1 [M+H]$^+$.

EXAMPLE 3

2-(3-Methoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 3-methoxybenzoic acid instead of o-toluic acid to the title compound (SiO$_2$, heptane:ethyl acetate=80:20 to 20:80, 205 mg, 67%) which was obtained as a white solid. MS: m/e=334.1 [M+H]$^+$.

EXAMPLE 4

2-(2-Methoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2-methoxybenzoic acid instead of o-toluic acid to the title compound (SiO$_2$, heptane:ethyl acetate 95:5 to 50:50, 170 mg, 55%) which was obtained as a white foam. MS: m/e=334.0 [M+H]$^+$.

EXAMPLE 5

2-(4-Methoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 4-methoxybenzoic acid instead of o-toluic acid to the title compound (SiO$_2$, heptane:ethyl acetate=95:5 to 0:100, 192 mg, 63%) which was obtained as a white foam. MS: m/e=334.2 [M+H]$^+$.

EXAMPLE 6

2-Chloro-3-[5-(5-methyl-3-phenyl-isoxazol-4-yl)-[1,3,4]oxadiazol-2-yl]-pyridine

As described for example 2, 5-methyl-3-phenyl-isoxazole-4-carboxylic acid hydrazide (200 mg, 0.92 mmol) was converted using 2-methoxy-nicotinic acid instead of o-toluic acid to the title compound (SiO$_2$, heptane:ethyl acetate=80:20 to 50:50, 64 mg, 21%) which was obtained as a white solid. MS: m/e=339.1 [M+H]$^+$.

EXAMPLE 7

8-[5-(5-Methyl-3-phenyl-isoxazol-4-yl)-[1,3,4]oxadiazol-2-yl]-quinoline

As described for example 2, 5-methyl-3-phenyl-isoxazole-4-carboxylic acid hydrazide (200 mg, 0.92 mmol) was converted using quinoline-8-carboxylic acid instead of o-toluic acid to the title compound (SiO$_2$, heptane:ethyl acetate=80:20 to 50:50, 160 mg, 49%) which was obtained as a white solid. MS: m/e=355.2 [M+H]$^+$.

EXAMPLE 8

2-(2-Ethoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2-ethoxybenzoic acid instead of o-toluic acid to the title compound (SiO$_2$, heptane:ethyl acetate=80:20 to 50:50, 135 mg, 42%) which was obtained as an off-white solid. MS: m/e=348.3 [M+H]$^+$.

EXAMPLE 9

2-[5-(5-Methyl-3-phenyl-isoxazol-4-yl)-[1,3,4]oxadiazol-2-yl]-pyridine

As described for example 2, 5-methyl-3-phenyl-isoxazole-4-carboxylic acid hydrazide (200 mg, 0.92 mmol) was converted using 2-picolinic acid instead of o-toluic acid to the title compound (SiO$_2$, heptane:ethyl acetate:dichloromethane=60:20:20 to 0:80:20, 43 mg, 15%) which was obtained as an off-white solid. MS: m/e 305.2 [M+H]$^+$.

EXAMPLE 10

2-(2,4-Dimethoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2,4-dimethoxybenzoic acid instead of o-toluic acid to the title compound (SiO$_2$, heptane:ethyl acetate=80:20 to 50:50, 207 mg, 62%) which was obtained as a white solid. MS: m/e=364.2 [M+H]$^+$.

EXAMPLE 11

2-(2-Methoxy-4-nitro-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (2.00 g, 9.12 mmol) was converted using 2-methoxy-4-nitro-benzoic acid instead of o-toluic acid to the title compound (2.92 g, 84%) which was obtained as a white solid. MS: m/e=379.2 [M+H]$^+$.

EXAMPLE 12

2-[5-(5-Methyl-3-phenyl-isoxazol-4-yl)-[1,3,4]oxadiazol-2-yl]-phenylamine a) 2-(5-Methyl-3-phenyl-isoxazol-4-yl)-5-(2-nitro-phenyl)-[1,3,4]oxadiazole As described for example 2, 5-methyl-3-phenyl-isoxazole-4-carboxylic acid hydrazide (2.00 g, 9.12 mmol) was converted using 2-nitro-benzoic acid instead of o-toluic acid to the title compound (2.52 g, 79%) which was obtained as a light-brown solid. MS: m/e=349.1 [M+H]$^+$.

b) 2-[5-(5-Methyl-3-phenyl-isoxazol-4-yl)-[1,3,4]oxadiazol-2-yl]-phenylamine

To a suspension of 2-(5-methyl-3-phenyl-isoxazol-4-yl)-5-(2-nitro-phenyl)-[1,3,4]oxadiazole (2.20 g, 63.2 mmol) in ethanol (100 mL) was added under a nitrogen atmosphere aqueous HCl (1 M, 7.6 mL, 76 mmol) and tin(II) chloride dihydrate (7.13 g, 31.6 mmol). The reaction mixture was then stirred for 2 h at 90° C., cooled to ambient temperature and poured onto an aqueous solution of sodium carbonate (saturated, 50 mL) and ethyl acetate (100 mL), stirred for 1 h and was filtered over Hyflo®. The Hyflo® was then washed with ethyl acetate (500 mL) and the aqueous phase extracted with ethyl acetate (100 mL). Drying over sodium sulfate, concentration and purification by chromatography (SiO$_2$, heptane: ethyl acetate 95:5 to 50:50) afforded the title compound (564 mg, 28%) as a white solid. MS: m/e=319.1 [M+H]$^+$.

EXAMPLE 13

3-Methoxy-4-[5-(5-methyl-3-phenyl-isoxazol-4-yl)-[1,3,4]oxadiazol-2-yl]-phenylamine To a suspension of 2-(2-methoxy-4-nitro-phenyl)-5-(5-methyl-3-phenyl-isoxazol-4-yl)-[1,3,4]oxadiazole (200 mg, 0.53 mmol) in ethanol (2 mL) was added iron powder (148 mg, 2.64 mmol) and aqueous HCl (1 M, 0.53 mL, 0.53 mmol). The reaction mixture was stirred for 2 h at 90° C., cooled to ambient temperature and poured onto an aqueous solution of sodium carbonate (saturated, 20 mL) and ethyl acetate (20 mL) and then stirred for 1 h. Filtration over Hyflo® was followed by washing of the Hyflo® with ethyl acetate. The aqueous phase was extracted with ethyl acetate (20 mL). Drying over sodium sulfate, concentration and purification by chromatography (SiO$_2$, heptane:ethyl acetate=50:50 to 0:100) afforded the title compound (80 mg, 43%) as a white solid. MS: m/e=349.2 [M+H]$^+$.

EXAMPLE 14

2-(2-Methoxy-4-methyl-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 2-methoxy-4-methyl-benzoic acid instead of o-toluic acid to the title compound (SiO$_2$, heptane:ethyl acetate:dichloromethane=75:5:20 to 60:20:20, 155 mg, 48%) which was obtained as a white solid. MS: m/e=348.2 [M+H]$^+$.

EXAMPLE 15

2-(2,5-Dimethoxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2,5-dimethoxybenzoic acid instead of o-toluic acid to the title compound (SiO$_2$, heptane:ethyl acetate:dichloromethane=75:5:20 to 60:20:20, 176 mg, 53%) which was obtained as a white solid. MS: m/e=364.2 [M+H]$^+$.

EXAMPLE 16

Cyclopropanecarboxylic acid {3-methoxy-4-[5-(5-methyl-3-phenyl-isoxazol-4-yl)-[1,3,4]oxadiazol-2-yl]-phenyl}-amide To a solution of 3-methoxy-4-[5-(5-methyl-3-phenyl-isoxazol-4-yl)-[1,3,4]oxadiazol-2-yl]-phenylamine (200 mg, 0.57 mmol) in THF (2 mL) was added N,N-diisopropyl ethyl amine (0.15 mL, 0.86 mmol), 4-dimethylaminopyridine (8 mg, 0.06 mmol) and cyclopropanecarbonyl chloride (68 µL, 0.75 mmol). The resulting suspension was stirred for 18 h at ambient temperature before it was extracted with a mixture of aqueous sodium carbonate (saturated, 20 mL) and ethyl acetate (20 mL). The aqueous layer was extracted with ethyl acetate (20 mL) and the combined organic layers dried over sodium sulfate. Purification by chromatography (SiO$_2$, heptane:ethyl acetate:dichloromethane=40:40:20 to 10:70:20) afforded the title compound (226 mg, 95%) as a light yellow solid. MS: m/e=417.3 [M+H]$^+$.

EXAMPLE 17

Cyclopropanecarboxylic acid {3-methoxy-4-[5-(5-methyl-3-phenyl-isoxazol-4-yl)-[1,3,4]oxadiazol-2-yl]-phenyl}-methyl-amide To a solution of cyclopropanecarboxylic acid {3-methoxy-4-[5-(5-methyl-3-phenyl-isoxazol-4-yl)-[1,3,4]oxadiazol-2-yl]-phenyl}-amide (138 mg, 0.33 mmol) in DMF (2 mL) was added at ambient temperature potassium bis(trimethylsilyl)amide (0.91 M in THF, 0.44 mL, 0.40 mmol). After the dark brown solution was stirred for 15 min iodomethane (25 µL, 0.40 mmol) was added and the reaction mixture was stirred for 18 h in a closed flask. It was then extracted with water (20 mL) and ethyl acetate (20 mL). The combined organic layers were then washed with aqueous sodium carbonate (saturated, 20 mL), concentrated, dissolved in ethyl acetate (3 mL) and treated with heptane (3 mL). The resulting suspension was filtered off and washed with ethyl acetate:heptane 1:1 (3 mL) affording the title compound (83 mg, 58%) as a white solid. MS: m/e=431.3 [M+H]$^+$.

EXAMPLE 18

(4-{5-[5-(2-Cyclopropyl-ethyl)-3-phenyl-isoxazol-4-yl]-[1,3,4]oxadiazol-2-yl}-3-methoxy-phenyl)-cyclo-propylmethyl-amine To a suspension of 3-methoxy-4-[5-(5-methyl-3-phenyl-isoxazol-4-yl)-[1,3,4]oxadiazol-2-yl]-phenylamine (200 mg, 0.57 mmol) in THF (2 mL) was added N,N-diisopropyl ethyl amine (128 µL, 0.75 mmol) and bromomethyl-cyclopropane (61 µL, 0.63 mmol) and the reaction mixture was stirred for 24 h at ambient temperature. After addition of potassium bis(trimethylsilyl)amide (0.91 M in THF, 0.82 mL, 0.75 mmol) stirring was continued for 15 min and further bromomethyl-cyclopropane (78 µL, 0.80 mmol) was added. After stirring for 18 h at ambient temperature further bromomethyl-cyclopropane (0.12 mL, 1.2 mmol) was added and stirring continued for 24 h at this temperature. The reaction mixture was extracted with aqueous sodium carbonate (saturated, 20 mL) and ethyl acetate (20 mL). The aqueous layer was extracted with ethyl acetate (20 mL) and the combined organic layers dried over sodium sulfate. Concentration and then purification by chromatography (SiO$_2$, heptane:ethyl acetate:dichloromethane=40:40:20 to 0:80:20) afforded the title compound (27 mg, 10%) as a light brown solid. MS: m/e=457.4 [M+H]$^+$.

EXAMPLE 19

Cyclopropylmethyl-{3-methoxy-4-[5-(5-methyl-3-phenyl-isoxazol-4-yl)-[1,3,4]oxadiazol-2-yl]-phenyl}-amine To a suspension of 3-methoxy-4-[5-(5-methyl-3-phenyl-isoxazol-4-yl)-[1,3,4]oxadiazol-2-yl]-phenylamine (200 mg, 0.57 mmol) in THF was added N,N-diisopropyl ethyl amine (128 µL, 0.75 mmol) and bromomethyl-cyclopropane (61 µL, 0.63 mmol) and the reaction mixture was stirred for 24 h at ambient temperature. After addition of potassium bis(trimethylsilyl)amide (0.91 M in THF, 0.82 mL, 0.75 mmol) was added stirring was continued for 15 min and further bromomethyl-cyclopropane (78 µL, 0.80 mmol) was added. After stirring for 18 h at ambient temperature further bromomethyl-cyclopropane (0.12 mL, 1.2 mmol) was added and stirring continued for 24 h at this temperature. The reaction mixture was extracted with aqueous sodium carbonate (saturated, 20 mL) and ethyl acetate (20 mL). The aqueous layer was extracted with ethyl acetate (20 mL) and the combined organic layers dried over sodium sulfate. Concentration and then purification by chromatography (SiO$_2$, heptane:ethyl acetate:dichloromethane=40:40:20 to 0:80:20) afforded the title compound (34 mg, 15%) as a light brown solid. MS: m/e=403.4 [M+H]$^+$.

EXAMPLE 20

4-{5-[5-(2-Cyclopropyl-ethyl)-3-phenyl-isoxazol-4-yl]-[1,3,4]oxadiazol-2-yl}-3-methoxy-phenylamine To a suspension of 3-methoxy-4-[5-(5-methyl-3-phenyl-isoxazol-4-yl)-[1,3,4]oxadiazol-2-yl]-phenylamine (200 mg, 0.57 mmol) in THF were added N,N-diisopropyl ethyl amine (128 µL, 0.75 mmol) and bromomethyl-cyclopropane (61 µL, 0.63 mmol) and the reaction mixture was stirred for 24 h at ambient temperature. After addition of potassium bis(trimethylsilyl)amide (0.91 M in THF, 0.82 mL, 0.75 mmol) was added stirring was continued for 15 min and further bromomethyl-cyclopropane (78 µL, 0.80 mmol) was added. After stirring for 18 h at ambient temperature further bromomethyl-cyclopropane (0.12 mL, 1.2 mmol) was added and stirring continued for 24 h at this temperature. The reaction mixture was extracted with aqueous sodium carbonate (saturated, 20 mL) and ethyl acetate (20 mL). The aqueous layer was extracted with ethyl acetate (20 mL) and the combined organic layers dried over sodium sulfate. Concentration and then purification by chromatography (SiO$_2$, heptane:ethyl acetate:dichloromethane=40:40:20 to 0:80:20) afforded the title compound (28 mg, 12%) as a light brown solid. MS: m/e=403.4 [M+H]$^+$.

EXAMPLE 21

N-{3-Methoxy-4-[5-(5-methyl-3-phenyl-isoxazol-4-yl)-[1,3,4]oxadiazol-2-yl]-phenyl}-bis-methane-sulfonyl-amine To a solution of 3-methoxy-4-[5-(5-methyl-3-phenyl-isoxazol-4-yl)-[1,3,4]oxadiazol-2-yl]-phenylamine (200 mg, 0.57 mmol) in THF (2 mL) were added N,N-diisopropyl ethyl amine (0.15 mL, 0.86 mmol), 4-dimethylaminopyridine (8 mg, 0.06 mmol) and methanesulfonyl chloride (53 µL, 0.69 mmol). The resulting suspension was then stirred for 18 h at ambient temperature. Further N,N-diisopropyl ethyl amine (0.15 mL, 0.86 mmol) and methanesulfonyl chloride (54 µL, 0.689 mmol) was added and stirred was continued for 24 h at 50° C. The reaction mixture was extracted with aqueous HCl (1 M, 15 mL) and ethyl acetate (20 mL). The aqueous layer was extracted with ethyl acetate (20 mL) and the combined organic layers were washed with brine (half-saturated, 20 mL) and aqueous sodium carbonate (saturated, 20 mL). Drying over sodium sulfate and purification by chromatography (SiO$_2$, heptane:ethyl acetate:dichloromethane=60:20:20 to 0:80:20) afforded the title compound (205 mg, 71%) as a white solid. MS: m/e=505.0 [M+H]$^+$.

EXAMPLE 22

N-{3-Methoxy-4-[5-(5-methyl-3-phenyl-isoxazol-4-yl)-[1,3,4]oxadiazol-2-yl]-phenyl}-methanesulfonamide To a solution of 3-methoxy-4-[5-(5-methyl-3-phenyl-isoxazol-4-yl)-[1,3,4]oxadiazol-2-yl]-phenylamine (200 mg, 0.57 mmol) in THF (2 mL) was added N,N-diisopropyl ethyl amine (0.15 mL, 0.86 mmol), 4-dimethylaminopyridine (8 mg, 0.06 mmol) and methanesulfonyl chloride (53 µL, 0.69 mmol). The resulting suspension was stirred for 18 h at ambient temperature. Further N,N-diisopropyl ethyl amine (0.15 mL, 0.86 mmol) and methanesulfonyl chloride (54 µL, 0.689 mmol) were added and stirred was continued for 24 h at 50° C. The reaction mixture was then extracted with aqueous HCl (1 M, 15 mL) and ethyl acetate (20 mL). The aqueous layer was extracted with ethyl acetate (20 mL) and the combined organic layers were washed with brine (half-saturated, 20 mL) and aqueous sodium carbonate (saturated, 20 mL). Drying over sodium sulfate, concentration and purification by chromatography (SiO$_2$, heptane:ethyl acetate:dichloromethane=60:20:20 to 0:80:20) afforded the title compound (34 mg, 14%) as a light yellow solid. MS: m/e=427.0 [M+H]$^+$.

EXAMPLE 23

Thiophene-3-carboxylic acid-{3-methoxy-4-[5-(5-methyl-3-phenyl-isoxazol-4-yl)-[1,3,4]oxadiazol-2-yl]-phenyl}-amide To a solution of 3-thiophenecarboxylic acid (162 mg, 1.26 mmol) in dichloromethane (4 mL) was added 1-(3-dimethylaminopropyl)-3-ethylcarbodiimide hydrochloride (242 mg, 1.26 mmol). After stirring for 2 min 3-methoxy-4-[5-(5-methyl-3-phenyl-isoxazol-4-yl)-[1,3,4]oxadiazol-2-yl]-phenylamine (400 mg, 1.15 mmol) was added and stirring was continued for 3 d at ambient temperature. The reaction mixture was extracted with aqueous HCl (1 M, 15 mL) and ethyl acetate (20 mL) and the aqueous layer was extracted with ethyl acetate (20 mL. Drying over sodium sulfate, concentration and purification by chromatography (SiO$_2$, heptane:ethyl acetate:dichloromethane=60:20:20 to 0:80:20) afforded the title compound (268 mg, 51%) as a white solid. MS: m/e=459.2 [M+H]$^+$.

EXAMPLE 24

2-(4-Fluoro-2-methoxy-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (2.00 g, 9.12 mmol) was converted using 4-fluoro-2-methoxy-benzoic acid instead of o-toluic acid to the title compound (SiO$_2$, heptane:ethyl acetate:dichloromethane=70:10:20 to 40:40:20, 1.59 g, 49%) which was obtained as a white solid. MS: m/e=352.3 [M+H]$^+$.

EXAMPLE 25

6-[5-(5-Methyl-3-phenyl-isoxazol-4-yl)-[1,3,4]oxadiazol-2-yl]-1H-benzotriazole

As described for example 2, 5-methyl-3-phenyl-isoxazole-4-carboxylic acid hydrazide (200 mg, 0.92 mmol) was converted using 5-carboxy-benzotriazole instead of o-toluic acid to the title compound (SiO$_2$, heptane:ethyl acetate:dichloromethane=70:20:10 to 20:70:10, 125 mg, 39%) which was obtained as a white solid. MS: m/e 345.1 [M+H]$^+$.

EXAMPLE 26

4-{3-Methoxy-4-[5-(5-methyl-3-phenyl-isoxazol-4-yl)-[1,3,4]oxadiazol-2-yl]-phenyl}-thiomorpholine To a solution of 2-(4-fluoro-2-methoxy-phenyl)-5-(5-methyl-3-phenyl-isoxazol-4-yl)-[1,3,4]oxadiazole (200 mg, 0.57 mmol) in DMSO (2 mL) was added thiomorpholine (0.29 mL, 2.85 mmol) and the reaction mixture was stirred for 5 h at 170° C. After cooling to ambient temperature it was extracted with water (20 mL) and ethyl acetate (20 mL). The aqueous layer was extracted with ethyl acetate (20 mL) and the combined organic layers were washed with brine (half-saturated, 20 mL) and aqueous sodium carbonate (saturated, 20 mL). Drying over sodium sulfate and purification by chromatography (SiO$_2$, heptane:ethyl acetate:dichloromethane=70:10:20 to 40:40:20) afforded the title compound (164 mg, 66%) as an off-white solid. MS: m/e=435.3 [M+H]$^+$.

EXAMPLE 27

5-[5-(5-Methyl-3-phenyl-isoxazol-4-yl)-[1,3,4]oxadiazol-2-yl]-1H-benzoimidazole

As described for example 2, 5-methyl-3-phenyl-isoxazole-4-carboxylic acid hydrazide (400 mg, 1.84 mmol) was converted using benzimidazole-5-carboxylic acid instead of o-toluic acid to the title compound (SiO$_2$, heptane:ethyl acetate:dichloromethane:methanol=70:20:10:0 to 0:80:10:10, 33 mg, 5%) which was obtained as an off-white solid. MS: m/e=344.1 [M+H]$^+$.

EXAMPLE 28

4-{3-Methoxy-4-[5-(5-methyl-3-phenyl-isoxazol-4-yl)-[1,3,4]oxadiazol-2-yl]-phenyl}-thiomorpholine 1,1-dioxide To a solution of 4-{3-methoxy-4-[5-(5-methyl-3-phenyl-isoxazol-4-yl)-[1,3,4]oxadiazol-2-yl]-phenyl}-thiomorpholine (156 mg, 0.36 mmol) in dichloromethane (2 mL) and methanol (2 mL) was added oxone (331 mg, 0.54 mmol) and the reaction mixture was stirred for 18 h at ambient temperature and then for 4 h at 50° C. After cooling to ambient temperature oxone (331 mg, 0.54 mmol) was added and stirred for 18 h at 50° C. before it was cooled to ambient temperature and sodium bisulfite solution (38%, 1.5 mL) was added and stirred for 15 min. After the addition of aqueous sodium carbonate (saturated, 10 mL) the mixture was extracted with ethyl acetate (20 mL) and washed with aqueous sodium carbonate (20 mL). After drying over sodium sulfate the concentrated residue was dissolved in dichloromethane (5 mL) and diluted with tert-butylmethylether (20 mL). The dichloromethane was distilled off and the resulting suspension was filtered affording the title compound (116 mg, 69%) as a white solid. MS: m/e=467.2 [M+H]$^+$.

EXAMPLE 29

1-{3-Methoxy-4-[5-(5-methyl-3-phenyl-isoxazol-4-yl)-[1,3,4]oxadiazol-2-yl]-phenyl}-piperidin-4-ol As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 4-hydroxy-piperidine instead of thiomorpholine to the title compound (SiO$_2$, dichloromethane:methanol=100:0 to 90:10, 197 mg, 79%) which was obtained as an off-white solid. MS: m/e=433.3 [M+H]$^+$.

EXAMPLE 30

2-(4-Methanesulfonyl-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 4-(methanesulfonyl)-benzoic acid instead of o-toluic acid to the title compound (SiO$_2$, heptane:ethyl acetate:dichloromethane=50:30:20 to 20:60:20, 36 mg, 10%) which was obtained as a white solid. MS: m/e=382.1 [M+H]$^+$.

EXAMPLE 31

2-(3-Methanesulfonyl-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 3-(methylsulfonyl)-benzoic acid instead of o-toluic acid to the title compound (SiO$_2$, heptane:ethyl acetate:dichloromethane=50:30:20 to 20:60:20, 44 mg, 13%) which was obtained as a white solid. MS: m/e=382.1 [M+H]$^+$.

EXAMPLE 32

5-(5-Methyl-3-phenyl-isoxazol-4-yl)-2-(4-nitro-phenyl)-[1,3,4]oxadiazole

As described for example 2, 5-methyl-3-phenyl-isoxazole-4-carboxylic acid hydrazide (2.00 g, 9.21 mmol) was converted using 4-nitro-benzoic acid instead of o-toluic acid to the title compound (1.59 mg, 50%) which was obtained as an off-white solid. MS: m/e=349.3 [M+H]$^+$.

EXAMPLE 33

2-(4-Imidazol-1-yl-2-methoxy-phenyl)-5-(5-methyl-3-phenyl-isoxazol-4-yl)-[1,3,4]oxadiazole As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using imidazole instead of thiomorpholine to the title compound (SiO$_2$, heptane:ethyl acetate:dichloromethane=70:10:20 to 40:40:20, 82 mg, 36%) which was obtained as an off-white solid. MS: m/e=400.2 [M+H]$^+$.

EXAMPLE 34

5-[5-(5-Methyl-3-phenyl-isoxazol-4-yl)-[1,3,4]oxadiazol-2-yl]-1,3-dihydro-benzoimidazol-2-one a) 5-(Imidazole-1-carbonyl)-1,3-dihydro-benzoimidazol-2-one To a solution of 1,1'-carbonyl-diimidazole (11.7 g, 72.3 mmol) in THF (500 mL) was added 3,4-diaminobenzoic acid (5.00 g, 32.9 mmol) and stirred for 3 days at ambient temperature. The reaction mixture was concentrated and stirred for 30 min at 80° C. in water (100 mL). The resulting suspension was then cooled to ambient temperature and the mixture was filtered off and washed with water (2×50 mL) to afford the title compound (4.94 g, 66%) which was obtained as a white solid. MS: m/e=229.3 [M+H]$^+$.

b) 5-[5-(5-Methyl-3-phenyl-isoxazol-4-yl)-[1,3,4]oxadiazol-2-yl]-1,3-dihydro-benzoimidazol-2-one To a suspension of 5-methyl-3-phenyl-isoxazole-4-carboxylic acid hydrazide (200 mg, 0.92 mmol) in chlorobenzene (2 mL) was added 5-(imidazole-1-carbonyl)-1,3-dihydro-benzoimidazol-2-one (315 mg, 1.38 mmol) and stirred for 18 h at 100° C. After cooling to ambient temperature phosphorus oxychloride (126 µL, 1.38 mmol) was added and the suspension was stirred for 4 h at 100° C. It was then cooled to ambient temperature and water (2 mL) was added, stirred for 15 min, and the resulting precipitate filtered off and washed with water (5 mL) and tert-butylmethylether (5 mL). Recrystallisation from ethanol afforded the title compound (257 mg, 78%) which was obtained as a light-grey solid. MS: m/e=360.1 [M+H]$^+$.

EXAMPLE 35

4-[5-(5-Methyl-3-phenyl-isoxazol-4-yl)-[1,3,4]oxadiazol-2-yl]-phenylamine

As described for example 13, 5-(5-methyl-3-phenyl-isoxazol-4-yl)-2-(4-nitro-phenyl)-[1,3,4]oxadiazole (1.49 g, 4.27 mmol) instead of 2-(2-methoxy-4-nitro-phenyl)-5-(5-methyl-3-phenyl-isoxazol-4-yl)-[1,3,4]oxadiazole was converted to the title compound (recrystallisation from tert-butylmethylether, 580 mg, 43%) which was obtained as a light brown solid. MS: m/e=319.1 [M+H]$^+$.

EXAMPLE 36

2-(4-Fluoro-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (5.00 g, 23.0 mmol) was converted using 4-fluorobenzoic acid instead of o-toluic acid to the title compound (recrystallisation from tert-butylmethylether, 2.98 g, 40%) which was obtained as an off-white solid. MS: m/e=322.2 [M+H]$^+$.

EXAMPLE 37

4-{4-[5-(5-Methyl-3-phenyl-isoxazol-4-yl)-[1,3,4]oxadiazol-2-yl]-phenyl}-thiomorpholine As described for example 26, 2-(4-fluoro-phenyl)-5-(5-methyl-3-phenyl-isoxazol-4-yl)-[1,3,4]oxadiazole (400 mg, 1.24 mmol) instead of 2-(4-fluoro-2-methoxy-phenyl)-5-(5-methyl-3-phenyl-isoxazol-4-yl)-[1,3,4]oxadiazole was converted to the title compound (SiO$_2$, heptane:ethyl acetate:dichloromethane=70:10:20 to 40:40:20, 309 mg, 61%) which was obtained as a light brown solid. MS: m/e=405.3 [M+H]$^+$.

EXAMPLE 38

4-{4-[5-(5-Methyl-3-phenyl-isoxazol-4-yl)-[1,3,4]oxadiazol-2-yl]-phenyl}-thiomorpholine 1,1-dioxide To a suspension of 4-{4-[5-(5-methyl-3-phenyl-isoxazol-4-yl)-[1,3,4]oxadiazol-2-yl]-phenyl}-thiomorpholine (239 mg, 0.59 mmol) in methanol (2 mL) and water (0.5 mL) was added oxone (545 mg, 0.89 mmol) and stirred for 18 h at 60° C. and for 4 h at 50° C. After the reaction mixture was cooled to ambient temperature further oxone (331 mg, 0.54 mmol) was added and stirred for 18 h at 50° C. It was cooled to ambient temperature and aqueous sodium bisulfite (38%, 1.5 mL) was then added and stirred for 15 min. After the addition of aqueous sodium carbonate (saturated, 10 mL) the mixture was extracted with ethyl acetate (20 mL) and washed with aqueous sodium carbonate (saturated, 20 mL). Drying over sodium sulfate, concentration and purification by chromatography (SiO$_2$, heptane:ethyl acetate:dichloromethane:methanol=40:50:10:0 to 0:90:0:10) afforded the title compound (75 mg, 29%) as a white solid. MS: m/e=437.2 [M+H]$^+$.

EXAMPLE 39

4-{4-[5-(5-Methyl-3-phenyl-isoxazol-4-yl)-[1,3,4]oxadiazol-2-yl]-phenyl}-thiomorpholine 1-oxide To a suspension of 4-{4-[5-(5-methyl-3-phenyl-isoxazol-4-yl)-[1,3,4]oxadiazol-2-yl]-phenyl}-thiomorpholine (239 mg, 0.59 mmol) in methanol (2 mL) and water (0.5 mL) was added oxone (545 mg, 0.89 mmol) and stirred for 18 h at 60° C. and for 4 h at 50° C. After the reaction mixture was cooled to ambient temperature further oxone (331 mg, 0.54 mmol) was added and stirred for 18 h at 50° C. It was cooled to ambient temperature and aqueous sodium bisulfite (38%, 1.5 mL) was added and stirred for 15 min. After the addition of aqueous sodium carbonate (saturated, 10 mL) the mixture was extracted with ethyl acetate (20 mL) and washed with aqueous sodium carbonate (saturated, 20 mL). Drying over sodium sulfate and purification by chromatography (SiO$_2$, heptane:ethyl acetate:dichloromethane:methanol=40:50:10:0 to 0:90:0:10) afforded the title compound (50 mg, 20%) as a white solid. MS: m/e=421.1 [M+H]$^+$.

EXAMPLE 40

4-[5-(5-Methyl-3-phenyl-isoxazol-4-yl)-[1,3,4]oxadiazol-2-yl]-pyridine

As described for example 2, 5-methyl-3-phenyl-isoxazole-4-carboxylic acid hydrazide (200 mg, 0.92 mmol) was converted using isonicotinic acid instead of o-toluic acid to the title compound (SiO$_2$, heptane:ethyl acetate:dichloromethane:methanol=40:50:10:0 to 0:90:0:10, 57 mg, 20%) which was obtained as a white foam. MS: m/e=305.3 [M+H]$^+$.

EXAMPLE 41 rac-(2S,6R)-2,6-Dimethyl-4-{4-[5-(5-methyl-3-phenyl-isoxazol-4-yl)-[1,3,4]oxadiazol-2-yl]-phenyl}-morpholine A suspension of 2-(4-fluoro-2-methoxy-phenyl)-5-(5-methyl-3-phenyl-isoxazol-4-yl)-[1,3,4]oxadiazole (200 mg, 0.62 mmol) in 2,6-dimethylmorpholine (2.00 mL, 16.0 mmol) was heated for 30 min at 200° C. (microwave) followed by stirring under gently reflux for 18 h at 160° C. After addition of DMSO (2 mL) and 2,6-dimethylmorpholine (0.50 mL, 4.00 mmol) the solution was stirred for another 24 h at 160° C. After cooling to ambient temperature the reaction mixture was extracted with water (20 mL) and ethyl acetate (20 mL). The aqueous layer was extracted with ethyl acetate (20 mL) and the combined organic layers were washed with brine (20 mL) and aqueous sodium carbonate (saturated, 20 mL). Drying over sodium sulfate, concentration and purification by chromatography (SiO$_2$, heptane:ethyl acetate:

dichloromethane=70:10:20 to 40:40:20) afforded the title compound (61 mg, 24%) as a white solid. MS: m/e=417.3 [M+H]⁺.

EXAMPLE 42

2-(2-Difluoromethoxy-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 2-(difluoromethoxy)-benzoic acid instead of o-toluic acid to the title compound (SiO$_2$, heptane:ethyl acetate:dichloromethane=70:10:20 to 40:40:20, 294 mg, 86%) which was obtained as a white solid. MS: m/e=370.0 [M+H]⁺.

EXAMPLE 43

2-(5-Methyl-3-phenyl-isoxazol-4-yl)-5-(2-trifluoromethoxy-phenyl)-[1,3,4]oxadiazole As described for example 2, 5-methyl-3-phenyl-isoxazole-4-carboxylic acid hydrazide (200 mg, 0.92 mmol) was converted using 2-(trifluoromethoxy)-benzoic acid instead of o-toluic acid to the title compound (SiO$_2$, heptane:ethyl acetate:dichloromethane=70:10:20 to 40:40:20, 134 mg, 38%) which was obtained as a white solid. MS: m/e=388.0 [M+H]⁺.

EXAMPLE 44

4-[5-(5-Methyl-3-phenyl-isoxazol-4-yl)-[1,3,4]oxadiazol-2-yl]-quinoline

As described for example 2, 5-methyl-3-phenyl-isoxazole-4-carboxylic acid hydrazide (200 mg, 0.92 mmol) was converted using quinoline-4-carboxylic acid instead of o-toluic acid to the title compound (SiO$_2$, heptane:ethyl acetate:dichloromethane=50:30:20 to 20:60:20, 75 mg, 23%) which was obtained as a white solid. MS: m/e=355.2 [M+H]⁺.

EXAMPLE 45

2-(3-Fluoro-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (2.00 g, 9.21 mmol) was converted using 3-fluorobenzoic acid instead of o-toluic acid to the title compound (SiO$_2$, heptane:ethyl acetate:dichloromethane=70:10:20 to 40:40:20, 1.75 mg, 59%) which was obtained as an off-white solid. MS: m/e 322.1 [M+H]⁺.

EXAMPLE 46

2-(2-Benzyloxy-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2-benzyloxybenzoic acid instead of o-toluic acid to the title compound (SiO$_2$, heptane:ethyl acetate:dichloromethane=70:10:20 to 40:40:20, 109 mg, 29%) which was obtained as a white solid. MS: m/e=410.1 [M+H]⁺.

EXAMPLE 47

1-{4-[5-(5-Methyl-3-phenyl-isoxazol-4-yl)-[1,3,4]oxadiazol-2-yl]-phenyl}-piperidine To a solution of 2-(4-fluoro-phenyl)-5-(5-methyl-3-phenyl-isoxazol-4-yl)-[1,3,4]oxadiazole (200 mg, 0.62 mmol) in DMSO (2 mL) was added piperidine (307 µL, 3.11 mmol) and the resulting mixture stirred for 5 h at 170° C. After cooling to ambient temperature the reaction mixture was extracted with aqueous hydrochloric acid (1 N, 20 mL) and ethyl acetate (20 mL). The aqueous layer was extracted with ethyl acetate (20 mL) and the combined organic layers were washed with brine (half-saturated, 20 mL) and aqueous sodium carbonate (saturated, 20 mL). Drying over sodium sulfate and purification by chromatography (SiO$_2$, heptane:ethyl acetate:dichloromethane=80:0:20 to 50:30:20) afforded the title compound (192 mg, 80%) as a white solid. MS: m/e=387.1 [M+H]⁺.

EXAMPLE 48

5-[5-(5-Methyl-3-phenyl-isoxazol-4-yl)-[1,3,4]oxadiazol-2-yl]-pyridin-2-ylamine

To a suspension of 6-aminonicotinic acid (191 mg, 1.38 mmol) in chlorobenzene (2 mL) was added 1,1'-carbonyldiimidazole (224 mg, 1.38 mmol) and the resulting mixture stirred for 2 h at 90° C. After the suspension was cooled to ambient temperature 5-methyl-3-phenyl-isoxazole-4-carboxylic acid hydrazide (200 mg, 0.92 mmol) was added and stirred for 1 h at 90° C. After the reaction mixture was cooled to ambient temperature phosphorous oxychloride (0.84 mL, 9.20 mmol) was added and stirring was continued for 4 h at 90° C. The cooled reaction mixture was poured carefully onto a mixture of ethyl acetate (20 mL) and aqueous sodium carbonate (saturated, 20 mL) and was stirred for 1 h at ambient temperature. The aqueous layer was separated and extracted with ethyl acetate (20 mL) and the combined organic layers were washed with aqueous sodium carbonate (saturated). Drying over sodium sulfate and purification by chromatography (SiO$_2$, heptane:ethyl acetate:dichloromethane:methanol=40:40:20:0 to 0:75:20:5) afforded the title compound (27 mg, 9%) as a white solid. MS: m/e=320.0 [M+H]⁺.

EXAMPLE 49

2-(2-Methoxy-4-trifluoromethyl-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 2-methoxy-4-trifluoromethyl-benzoic acid instead of o-toluic acid to the title compound (SiO$_2$, heptane:ethyl acetate:dichloromethane=70:10:20 to 40:40:20, 185 mg, 50%) which was obtained as a white solid. MS: m/e=402.1 [M+H]⁺.

EXAMPLE 50

2-(5-Methyl-3-phenyl-isoxazol-4-yl)-5-(4-trifluoromethyl-phenyl)-[1,3,4]oxadiazole As described for example 2, 5-methyl-3-phenyl-isoxazole-4-carboxylic acid hydrazide (200 mg, 0.92 mmol) was converted using 4-trifluoromethyl-benzoic acid instead of o-toluic acid to the title compound (SiO$_2$, heptane:ethyl acetate:dichloromethane=70:10:20 to 40:40:20, 114 mg, 33%) which was obtained as a white solid. MS: m/e=372.0 [M+H]$^+$.

EXAMPLE 51

1,3-Dimethyl-5-[5-(5-methyl-3-phenyl-isoxazol-4-yl)-[1,3,4]oxadiazol-2-yl]-1,3-dihydro-benzoimidazol-2-one 5-[5-(5-Methyl-3-phenyl-isoxazol-4-yl)-[1,3,4]oxadiazol-2-yl]-1,3-dihydro-benzoimidazol-2-one (200 mg, 0.56 mmol) was heated in DMF (2 mL) until the suspension turned into solution. After the solution was cooled to ambient temperature iodomethane (38 µL, 0.61 mmol) was added and stirred for 18 h at this temperature. The resulting suspension was diluted with DMF (2 mL) and warmed until the reaction mixture became homogeneous. A solution of potassium bis (trimethylsilyl)amide (0.91 M in THF, 673 µL, 0.61 mmol) was added and stirred for 1 h at ambient temperature. Additional iodomethane (38 µL, 0.61 mmol) was added and stirring was continued for another 18 h. Additional potassium bis(trimethylsilyl)amide (0.91 M in THF, 673 µL, 0.61 mmol) was added, stirred for 15 min at ambient temperature, treated with iodomethane (0.38 µL, 0.61 mmol) and stirred for 5 h at this temperature. The reaction mixture was diluted with ethyl acetate (20 mL) and washed with aqueous sodium carbonate (saturated, 20 mL), water (20 mL) and brine (20 mL). The combined aqueous layers were extracted with ethyl acetate (20 mL) and the combined organic layers were dried over sodium sulfate. Purification by chromatography (SiO$_2$, heptane:ethyl acetate:dichloromethane=40:40:20 to 10:70:20) afforded the title compound (29 mg, 13%) as a white solid. MS: m/e=388.1 [M+H]$^+$.

EXAMPLE 52

2-(4-Difluoromethoxy-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 4-difluoromethoxy-benzoic acid instead of o-toluic acid to the title compound (SiO$_2$, heptane:ethyl acetate:dichloromethane=70:10:20 to 40:40:20, 85 mg, 25%) which was obtained as a white solid. MS: m/e=369.9 [M+H]$^+$.

EXAMPLE 53

5-[5-(5-Isopropyl-3-phenyl-isoxazol-4-yl)-[1,3,4] oxadiazol-2-yl]-1,3-dimethyl-1,3-dihydro-benzoimidazol-2-one 5-[5-(5-Methyl-3-phenyl-isoxazol-4-yl)-[1,3,4]oxadiazol-2-yl]-1,3-dihydro-benzoimidazol-2-one (200 mg, 0.56 mmol) was heated in DMF (2 mL) until the suspension turned into solution. After the solution was cooled to ambient temperature iodomethane (38 µL, 0.61 mmol) was added and stirred for 18 h at this temperature. The resulting suspension was diluted with DMF (2 mL) and warmed until the reaction mixture became homogeneous. A solution of potassium bis (trimethylsilyl)amide (0.91 M in THF, 673 µL, 0.61 mmol) was added and stirred for 1 h at ambient temperature. Additional iodomethane (38 µL, 0.61 mmol) was added and stirring was continued for another 18 h. Additional potassium bis(trimethylsilyl)amide (0.91 M in THF, 673 µL, 0.61 mmol) was added, stirred for 15 min at ambient temperature, treated with iodomethane (0.38 µL, 0.61 mmol) and stirred for 5 h at this temperature. The reaction mixture was diluted with ethyl acetate (20 mL) and washed with aqueous sodium carbonate (saturated, 20 mL), water (20 mL) and brine (20 mL). The combined aqueous layers were extracted with ethyl acetate (20 mL) and the combined organic layers were dried over sodium sulfate. Purification by chromatography (SiO$_2$, heptane:ethyl acetate:dichloromethane=40:40:20 to 10:70:20) afforded the title compound (38 mg, 16%) as a white solid. MS: m/e=416.1 [M+H]$^+$.

EXAMPLE 54

2-Chloro-4-[5-(5-methyl-3-phenyl-isoxazol-4-yl)-[1,3,4]oxadiazol-2-yl]-pyridine

As described for example 2, 5-methyl-3-phenyl-isoxazole-4-carboxylic acid hydrazide (1.92 mg, 8.83 mmol) was converted using 2-chloroisonicotinic acid instead of o-toluic acid to the title compound (SiO$_2$, heptane:ethyl acetate:dichloromethane=70:10:20 to 40:40:20, 1.41 mg, 47%) which was obtained as a white solid. MS: m/e=339.1 [M+H]$^+$.

EXAMPLE 55

4-{4-[5-(5-Methyl-3-phenyl-isoxazol-4-yl)-[1,3,4] oxadiazol-2-yl]-pyridin-2-yl}-morpholine To a solution of 2-chloro-4-[5-(5-methyl-3-phenyl-isoxazol-4-yl)-[1,3,4]oxadiazol-2-yl]-pyridine (200 mg, 0.59 mmol) in DMSO (2 mL) was added morpholine (257 µL, 2.95 mmol) and stirred for 18 h under an argon atmosphere at 170° C. After cooling to ambient temperature the resulting dark brown solution was extracted with ethyl acetate (20 mL) and aqueous sodium carbonate (saturated, 20 mL). The aqueous layer was extracted with ethyl acetate (20 mL) and the combined organic layers were washed with water (20 mL) and brine (20 mL). Drying over sodium sulfate and purification by chromatography (SiO$_2$, heptane:ethyl acetate:dichloromethane=70:10:20 to 40:40:20) afforded the title compound (166 mg, 72%) as a white solid. MS: m/e=390.1 [M+H]$^+$.

EXAMPLE 56

4-{3-Methoxy-4-[5-(5-methyl-3-phenyl-isoxazol-4-yl)-[1,3,4]oxadiazol-2-yl]-phenyl}-thiomorpholine 1-oxide To a solution of 4-{3-methoxy-4-[5-(5-methyl-3-phenyl-isoxazol-4-yl)-[1,3,4]oxadiazol-2-yl]-phenyl}-thiomorpholine (660 mg, 1.52 mmol) in dichloromethane (7 mL), methanol (7 mL) and water (0.1 mL) was added oxone (1.87 g, 3.04 mmol) and stirred for 8 h at 60° C. The reaction mixture was cooled to ambient temperature and aqueous sodium bisulfite (38%, 5 mL) was added and stirred for 1 h. After the addition of aqueous sodium carbonate (saturated, 30 mL) the mixture was extracted with dichloromethane (30 mL) and washed with aqueous sodium carbonate (half-saturated, 30 mL). Drying over sodium sulfate and purification by chromatography (SiO$_2$, heptane:ethyl acetate:dichloromethane:methanol=40:40:20:0 to 0:75:20:5) afforded the title compound (102 mg, 15%) as an off-white solid. MS: m/e=451.1 [M+H]$^+$.

EXAMPLE 57

4-[5-(5-Methyl-3-phenyl-isoxazol-4-yl)-[1,3,4]oxa-diazol-2-yl]-benzonitrile

As described for example 2, 5-methyl-3-phenyl-isoxazole-4-carboxylic acid hydrazide (1.09 mg, 5.00 mmol) was converted using 4-cyanobenzoic acid instead of o-toluic acid to the title compound (SiO$_2$, heptane:ethyl acetate=100:0 to 50:50, 490 mg, 30%) which was obtained as a white solid. MS: m/e=329.1 [M+H]$^+$.

EXAMPLE 58

2-[2-Methoxy-4-(2-methyl-imidazol-1-yl)-phenyl]-5-(5-methyl-3-phenyl-isoxazol-4-yl)-[1,3,4]oxadiaz-ole As described for example 26, 2-(4-fluoro-2-methoxy-phenyl)-5-(5-methyl-3-phenyl-isoxazol-4-yl)-[1,3,4]oxadiazole (190 mg, 0.54 mmol) was converted using 2-methyl-imidazole instead of thiomorpholine to the title compound (SiO$_2$, heptane:ethyl acetate:dichloromethane:methanol=20:70:10:0 to 0:90:0:10, 27 mg, 12%) which was obtained a light-brown solid. MS: m/e=414.1 [M+H]$^+$.

EXAMPLE 59

2-[4-(2-Methyl-imidazol-1-yl)-phenyl]-5-(5-methyl-3-phenyl-isoxazol-4-yl)-[1,3,4]oxadiazole As described for example 47, 2-(4-fluoro-phenyl)-5-(5-methyl-3-phenyl-isoxazol-4-yl)-[1,3,4]oxadiazole (200 mg, 0.62 mmol) was converted using 2-methyl-imidazole instead of piperidine to the title compound (110 mg, 46%) which was obtained a light-brown waxy solid. MS: m/e=384.0 [M+H]$^+$.

EXAMPLE 60

2-(5-Ethyl-3-phenyl-isoxazol-4-yl)-5-(4-fluoro-2-methoxy-phenyl)-[1,3,4]oxadiazole To a solution of 2-(4-fluoro-2-methoxy-phenyl)-5-(5-methyl-3-phenyl-isoxazol-4-yl)-[1,3,4]oxadiazole (1.00 g, 2.85 mmol) in DMF (10 mL) was added potassium hexamethyldisilazane (0.91 M in tetrahydrofuran, 3.44 mL, 3.13 mmol) at ambient temperature and the resulting mixture was stirred for 1 h. After addition of iodomethane (0.20 mL, 3.13 mmol) the reaction mixture was stirred for 20 h at this temperature. Further potassium hexamethyldisilazane (0.91 M in tetrahydrofuran, 3.44 mL, 3.13 mmol) and iodomethane (0.20 mL, 3.13 mmol) were added and stirring was continued for another 1.5 h. The reaction mixture was poured onto aqueous ammonium chloride (saturated, 50 mL) and was extracted with ethyl acetate. Drying over sodium sulfate and purification by chromatography (SiO$_2$, heptane:ethyl acetate:dichloromethane=70:10:20 to 0:80:20) afforded the title compound (14 mg, 1%) as a white solid. MS: m/e=366.1 [M+H]$^+$.

EXAMPLE 61

2-(4-Fluoro-2-methoxy-phenyl)-5-(5-isopropyl-3-phenyl-isoxazol-4-yl)-[1,3,4]oxadiazole To a solution of 2-(4-fluoro-2-methoxy-phenyl)-5-(5-methyl-3-phenyl-isoxazol-4-yl)-[1,3,4]oxadiazole (1.00 g, 2.85 mmol) in DMF (10 mL) was added potassium hexamethyldisilazane (0.91 M in tetrahydrofuran, 3.44 mL, 3.13 mmol) at ambient temperature and the resulting mixture was stirred for 1 h. After addition of iodomethane (0.20 mL, 3.13 mmol) the reaction mixture was stirred for 20 h at this temperature. Further potassium hexamethyldisilazane (0.91 M in tetrahydrofuran, 3.44 mL, 3.13 mmol) and iodomethane (0.20 mL, 3.13 mmol) were added and stirring was continued for another 1.5 h. The reaction mixture was poured onto aqueous ammonium chloride (saturated, 50 mL) and was extracted with ethyl acetate. Drying over sodium sulfate and purification by chromatography (SiO$_2$, heptane:ethyl acetate:dichloromethane=70:10:20 to 0:80:20) afforded the title compound (146 mg, 14%) as a white solid. MS: m/e=380.1 [M+H]$^+$.

EXAMPLE 62

Thiophene-2-sulfonic acid {3-methoxy-4-[5-(5-methyl-3-phenyl-isoxazol-4-yl)-[1,3,4]oxadiazol-2-yl]-phenyl}-amide To a solution of 3-methoxy-4-[5-(5-methyl-3-phenyl-isoxazol-4-yl)-[1,3,4]oxadiazol-2-yl]-phenylamine (200 mg, 0.57 mmol) in tetrahydrofuran (5 mL) were added N,N-diisopropylamine (111 mg, 0.86 mmol), 4-dimethylaminopyridine (7.0 mg, 0.06 mmol) and thiophenesulfonyl chloride (126 mg, 0.69 mmol) and the reaction mixture was stirred at ambient temperature for 4 d. The resulting suspension was extracted with ethyl acetate (20 mL) and the combined organic layers were washed with aqueous sodium carbonate (saturated). Drying over sodium sulfate and purification by chromatography (SiO$_2$, heptane:ethyl acetate:dichloromethane=50:30:20 to 20:60:20) afforded the title compound (95 mg, 33%) as an orange solid. MS: m/e=495.1 [M+H]$^+$.

EXAMPLE 63

Propane-2-sulfonic acid {3-methoxy-4-[5-(5-methyl-3-phenyl-isoxazol-4-yl)-[1,3,4]oxadiazol-2-yl]-phenyl}-amide To a solution of 3-methoxy-4-[5-(5-methyl-3-phenyl-isoxazol-4-yl)-[1,3,4]oxadiazol-2-yl]-phenylamine (200 mg, 0.57 mmol) in tetrahydrofuran (5 mL) was added at 0° C. potassium bis(trimethylsilyl)amide (0.91 M in tetrahydrofuran, 1.51 mL, 1.38 mmol). After stirring for 15 min at this temperature isopropylsulfonyl chloride (319 mg, 2.24 mmol) was added and stirring was continued at ambient temperature for 76 h. Further isopropylsulfonyl chloride (107 mg, 0.75 mmol) and pyridine (454 mg, 5.74) were added and stirring was continued for 24 h. The resulting suspension was extracted with ethyl acetate (20 mL) and the combined organic layers were washed with aqueous sodium carbonate (saturated). Drying over sodium sulfate and purification by chromatography (SiO$_2$, heptane:ethyl acetate:dichloromethane 50:30:20 to 20:60:20) afforded the title compound (29 mg, 11%) as a yellow solid. MS: m/e 455.2 [M+H]$^+$.

EXAMPLE 64

{3-Methoxy-4-[5-(5-methyl-3-phenyl-isoxazol-4-yl)-[1,3,4]oxadiazol-2-yl]-phenyl}-(tetrahydro-pyran-4-yl)-amine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 4-aminotetrahydropyran (173 mg, 1.71 mmol) and N,N-diisopropylethylamine (147 mg, 1.14 mmol) instead of thiomorpholine to the title compound (SiO$_2$, heptane:ethyl acetate:dichloromethane:methanol=40:40:20:0 to 0:75:20:5, 73 mg, 30%) which was obtained as a white solid. MS: m/e=433.3 [M+H]$^+$.

EXAMPLE 65

{3-Methoxy-4-[5-(5-methyl-3-phenyl-isoxazol-4-yl)-[1,3,4]oxadiazol-2-yl]-phenyl}-(1-methyl-piperidin-4-yl)-amine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 1-methylpiperidin-4-amine (195 mg, 1.71 mmol) and N,N-diisopropylethylamine (147 mg, 1.14 mmol) instead of thiomorpholine to the title compound (SiO$_2$, heptane:ethyl acetate:dichloromethane:methanol 40:40:20:0 to 0:75:20:5, 56 mg, 22%) which was obtained as an off-white solid. MS: m/e=446.2 [M+H]$^+$.

EXAMPLE 66

1-{3-Methoxy-4-[5-(5-methyl-3-phenyl-isoxazol-4-yl)-[1,3,4]oxadiazol-2-yl]-phenyl}-piperazine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using piperazine instead of thiomorpholine to the title compound (SiO$_2$, dichloromethane:(dichloromethane:methanol:ammonia=70:27:3)= 92:2 to 50:50, 40 mg, 17%) which was obtained as an off-white solid. MS: m/e=418.3 [M+H]$^+$.

EXAMPLE 67

1-{3-Methoxy-4-[5-(5-methyl-3-phenyl-isoxazol-4-yl)-[1,3,4]oxadiazol-2-yl]-phenyl}-4-methyl-piperazine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 1-methylpiperazine instead of thiomorpholine to the title compound (SiO$_2$, dichloromethane:(dichloromethane:methanol:ammonia=70:27:3)=92:2 to 80:20, 117 mg, 48%) which was obtained as an off-white solid. MS: m/e=432.4 [M+H]$^+$.

EXAMPLE 68

4-{3-Methoxy-4-[5-(5-methyl-3-phenyl-isoxazol-4-yl)-[1,3,4]oxadiazol-2-yl]-phenyl}-morpholine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using morpholine instead of thiomorpholine to the title compound (SiO$_2$, heptane:ethyl acetate:dichloromethane=60:20:20 to 0:80:20, 132 mg, 55%) which was obtained as an off-white solid. MS: m/e=419.2 [M+H]$^+$.

EXAMPLE 69

2-(5-Cyclopropyl-3-phenyl-isoxazol-4-yl)-5-(2-methoxy-phenyl)-[1,3,4]oxadiazole a) 5-Cyclopropyl-3-phenyl-isoxazole-4-carboxylic acid ethyl ester To a solution of N-hydroxybenzenecarboximidoyl chloride (*Tetrahedron Letters*, 47(9), 1457-1460, 2006, 500 mg, 3.21 mmol) and cyclopropyl-propynoic acid ethyl ester (*Organic Syntheses*, 66, 173-179, 1988, 515 mg, 3.21 mmol) in diethyl ether (5 mL) was added dropwise over a period of 2 min at ambient temperature triethylamine (0.54 ml, 3.86 mmol) and the reaction mixture was stirred for 3 d at this temperature. The resulting suspension was diluted with tert-butylmethylether (5 mL) and water (10 mL). The aqueous layer was extracted with tert-butylmethylether (10 ml) and the organic layers were washed with water (10 mL) and brine (10 mL). Drying over sodium sulfate and purification by chromatography (SiO$_2$, heptane:ethyl acetate=98:2 to 80:20) afforded the title compound (414 mg, 50%) as a colorless liquid. MS: m/e=258.1 [M+H]$^+$.

b) 5-Cyclopropyl-3-phenyl-isoxazole-4-carboxylic acid

To a solution of 5-cyclopropyl-3-phenyl-isoxazole-4-carboxylic acid ethyl ester (408 mg, 1.58 mmol) in ethanol (4 mL) was added aqueous sodium hydroxide (1 N, 3.17 mL, 3.17 mmol) and the mixture was stirred for 3 h at 80° C. The ethanol was distilled off and the residue diluted with water (5 mL) and acified with aqueous HCl (IN) to pH=1. The resulting suspension was filtered off and washed with water affording the title compound (314 mg, 86%) as a white solid. MS: m/e=230.3[M+H]$^+$.

c) 2-(5-Cyclopropyl-3-phenyl-isoxazol-4-yl)-5-(2-methoxy-phenyl)-[1,3,4]oxadiazole To a suspension of 5-cyclopropyl-3-phenyl-isoxazole-4-carboxylic acid (236 mg, 1.03 mmol) in dichloromethane (2 mL) were added 2-methoxybenzhydrazide (205 mg, 1.24 mmol), 2-chloro-1,3-dimethylimidazolium chloride (383 mg, 2.26 mmol) and triethylamine (0.52 ml, 5.15 mmol) at ambient temperature. The resulting suspension was stirred for 18 h at this temperature before diluting with dichloromethane (20 ml) and washing with water (20 mL) and brine (20 mL). The aqueous layers were extracted with dichlormethane and the combined organic layers dried over sodium sulfate. Purification by chromatography (SiO$_2$, heptane:ethyl acetate:dichloromethane=70:10:20 to 40:40:20) afforded the title compound (121 mg, 33%) as a white solid. MS: m/e=360.2 [M+H]$^+$.

EXAMPLE 70

2-Cyclohexyl-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using cyclohexanecarboxylic acid instead of o-toluic acid to the title compound (SiO$_2$, heptane:ethyl acetate:dichloromethane=70:10:20 to 40:40:20, 233 mg, 82%) which was obtained as a white solid. MS: m/e 362.3 [M+H]$^+$.

EXAMPLE 71

4-[5-(5-Methyl-3-phenyl-isoxazol-4-yl)-[1,3,4]oxadiazol-2-yl]-benzoic acid methyl ester As described for example 2, 5-methyl-3-phenyl-isoxazole-4-carboxylic acid hydrazide (2.00 g, 9.21 mmol) was converted using mono-methyl terephthalate instead of o-toluic acid to the title compound (1.98 mg, 60%) which was obtained as a colorless liquid. MS: m/e=310.3 [M+H]$^+$.

EXAMPLE 72

{3-Methoxy-4-[5-(5-methyl-3-phenyl-isoxazol-4-yl)-[1,3,4]oxadiazol-2-yl]-phenyl}-dimethyl-amine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using dimethylamine hydrochloride (232 mg, 2.85 mmol) and N,N-diisopropyl-ethylamine (294 mg, 2.28 mmol) instead of thiomorpholine to the title compound ($SiO_2$, heptane:ethyl acetate:dichloromethane 70:10:20 to 40:40:20, 8 mg, 4%) which was obtained as a light brown solid. MS: m/e=377.3 $[M+H]^+$.

EXAMPLE 73

2-(5-Cyclopropyl-3-phenyl-isoxazol-4-yl)-5-(4-fluoro-2-methoxy-phenyl)-[1,3,4]oxadiazole a) 5-Cyclopropyl-3-phenyl-isoxazole-4-carboxylic acid hydrazide As described for example 1a, 5-cyclopropyl-3-phenyl-isoxazole-4-carboxylic acid (5.69 g, 24.8 mmol) instead of 5-methyl-3-phenyl-isoxazole-4-carboxylic acid was converted to the title compound (6.13 mg, 99%) which was obtained as a white solid. MS: m/e=244.3 $[M+H]^+$.

b) 2-(5-Cyclopropyl-3-phenyl-isoxazol-4-yl)-5-(4-fluoro-2-methoxy-phenyl)-[1,3,4]oxadiazole As described for example 2, 5-cyclopropyl-3-phenyl-isoxazole-4-carboxylic acid hydrazide (1.32 g, 5.43 mmol) was converted using 4-fluoro-2-methoxy-benzoic acid instead of o-toluic acid to the title compound ($SiO_2$, heptane:ethyl acetate:dichloromethane=70:10:20 to 40:40:20, 631 mg, 31%) which was obtained as a white solid. MS: m/e=319.0 $[M+H]^+$.

EXAMPLE 74

5-[5-(5-Methyl-3-phenyl-isoxazol-4-yl)-[1,3,4]oxadiazol-2-yl]-1H-indole

As described for example 2, 5-methyl-3-phenyl-isoxazole-4-carboxylic acid hydrazide (500 mg, 2.30 mmol) was converted using indole-5-carboxylic acid instead of o-toluic acid to the title compound ($SiO_2$, heptane:ethyl acetate:dichloromethane=70:10:20 to 40:40:20, 430 mg, 55%) which was obtained as a colorless liquid. MS: m/e=343.1 $[M+H]^+$.

EXAMPLE 75

1-Methyl-5-[5-(5-methyl-3-phenyl-isoxazol-4-yl)-[1,3,4]oxadiazol-2-yl]-1H-indole To a solution of 5-[5-(5-methyl-3-phenyl-isoxazol-4-yl)-[1,3,4]oxadiazol-2-yl]-1H-indole (150 mg, 0.44 mmol) in DMF (2 mL) was added potassium carbonate (121 mg, 0.88 mmol) and iodomethane (0.04 ml, 0.66 mmol) and the reaction mixture was stirred for 3 d in a closed round bottomed flask at ambient temperature. The mixture was extracted with water (20 ml) and ethyl acetate (20 mL). The aqueous layer was extracted with ethyl acetate and the combined organic layers were washed with aqueous sodium carbonate (half saturated, 20 mL) and brine (20 mL). Drying over sodium sulfate and purification by chromatography ($SiO_2$, heptane:ethyl acetate:dichloromethane=70:10:20 to 40:40:20) afforded the title compound (136 mg, 87%) as a white solid. MS: m/e=357.2 $[M+H]^+$.

EXAMPLE 76

2-(2,4-Difluoro-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2,4-difluorobenzoic acid instead of o-toluic acid to the title compound ($SiO_2$, heptane:ethyl acetate:dichloromethane=70:10:20 to 40:40:20, 199 mg, 64%) which was obtained as a white solid. MS: m/e=340.2 $[M+H]^+$.

EXAMPLE 77

4-{4-[5-(5-Cyclopropyl-3-phenyl-isoxazol-4-yl)-[1,3,4]oxadiazol-2-yl]-3-methoxy-phenyl}-morpholine As described for example 26, 2-(4-fluoro-2-methoxy-phenyl)-5-(5-cyclopropyl-3-phenyl-isoxazol-4-yl)-[1,3,4]oxadiazole (200 mg, 0.53 mmol) instead of 2-(4-fluoro-2-methoxy-phenyl)-5-(5-methyl-3-phenyl-isoxazol-4-yl)-[1,3,4]oxadiazole was converted using morpholine instead of thiomorpholine to the title compound ($SiO_2$, heptane:ethyl acetate:dichloromethane=60:20:20 to 0:80:20, 138 mg, 59%) which was obtained as a white solid. MS: m/e=445.3 $[M+H]^+$.

EXAMPLE 78

N-Cyclopropyl-4-[5-(5-methyl-3-phenyl-isoxazol-4-yl)-[1,3,4]oxadiazol-2-yl]-benzamide a) 4-[5-(5-Methyl-3-phenyl-isoxazol-4-yl)-[1,3,4]oxadiazol-2-yl]-benzoic acid To a solution of 4-[5-(5-Methyl-3-phenyl-isoxazol-4-yl)-[1,3,4]oxadiazol-2-yl]-benzoic acid methyl ester (1.95 g, 5.47 mmol) in methanol (10 mL) was added aqueous sodium hydroxide (1 M, 11 mL, 11 mmol) and the mixture was stirred for 3 h at 70° C. After concentration the residue was diluted with water (20 mL) and the resulting suspension was acidified with aqueous HCl (1 N) to pH=1. filtration and washing with water afforded the title compound (1.90 g, 99%) which was obtained as a white solid. MS: m/e=348.1 $[M+H]^+$.

b) Imidazol-1-yl-{4-[5-(5-methyl-3-phenyl-isoxazol-4-yl)-[1,3,4]oxadiazol-2-yl]-phenyl}-methanone To a suspension of 4-[5-(5-methyl-3-phenyl-isoxazol-4-yl)-[1,3,4]oxadiazol-2-yl]-benzoic acid (1.90 g, 5.48 mmol) in tetrahydrofuran (20 mL) was added 1,1'-carbonyl-diimidazole (978 mg, 6.03 mmol) and the mixture was stirred for 0.5 h at 80° C. After cooling to ambient temperature the resulting suspension was poured onto water (100 mL), stirred for 15 min at ambient temperature and was filtered. Washing with water and drying afforded the title compound (1.51 g, 69%) which was obtained as a yellow solid. MS: m/e=398.2 $[M+H]^+$.

c) N-Cyclopropyl-4-[5-(5-methyl-3-phenyl-isoxazol-4-yl)-[1,3,4]oxadiazol-2-yl]-benzamide To a suspension of imidazol-1-yl-{4-[5-(5-methyl-3-phenyl-isoxazol-4-yl)-[1,3,4]oxadiazol-2-yl]-phenyl}-methanone (200 mg, 0.50 mmol) in tetrahydrofuran (2 mL) was added cyclopropylamine (37 mg, 0.65 mmol) and the mixture was stirred for 3 h at 80° C. After cooling to ambient temperature the resulting suspension was concentrated. Purification by chromatography ($SiO_2$, heptane:ethyl acetate:dichloromethane=60:20:20 to 0:80:20) afforded the title compound (149 mg, 77%) as a white solid. MS: m/e=387.2 $[M+H]^+$.

EXAMPLE 79

N-Cyclopropylmethyl-4-[5-(5-methyl-3-phenyl-isoxazol-4-yl)-[1,3,4]oxadiazol-2-yl]-benzamide As described for example 78c, imidazol-1-yl-{4-[5-(5-methyl-3-phenyl-isoxazol-4-yl)-[1,3,4]oxadiazol-2-yl]-phenyl}-methanone (200 mg, 0.50 mmol) was converted using aminomethylcyclopropane instead of cyclopropylamine to the title compound (SiO$_2$, heptane:ethyl acetate:dichloromethane=60:20:20 to 0:80:20, 88 mg, 44%) which was obtained as a white solid. MS: m/e=433.3 [M+H]$^+$.

EXAMPLE 80

{4-[5-(5-Methyl-3-phenyl-isoxazol-4-yl)-[1,3,4]oxadiazol-2-yl]-phenyl}-morpholin-4-yl-methanone As described for example 78c, imidazol-1-yl-{4-[5-(5-methyl-3-phenyl-isoxazol-4-yl)-[1,3,4]oxadiazol-2-yl]-phenyl}-methanone (200 mg, 0.50 mmol) was converted using morpholine instead of cyclopropylamine to the title compound (SiO$_2$, heptane:ethyl acetate:dichloromethane:methanol=40:40:20:0 to 0:75:20:5, 196 mg, 94%) which was obtained as a colorless foam. MS: m/e=417.3 [M+H]$^+$.

EXAMPLE 81

4-[5-(5-Methyl-3-phenyl-isoxazol-4-yl)-[1,3,4]oxadiazol-2-yl]-N-(tetrahydro-pyran-4-yl)-benzamide As described for example 78c, imidazol-1-yl-{4-[5-(5-methyl-3-phenyl-isoxazol-4-yl)-[1,3,4]oxadiazol-2-yl]-phenyl}-methanone (200 mg, 0.50 mmol) was converted using 4-aminotetrahydropyran instead of cyclopropylamine to the title compound (SiO$_2$, heptane:ethyl acetate:dichloromethane:methanol=40:40:20:0 to 0:75:20:5, 100 mg, 46%) which was obtained a white solid. MS: m/e=431.3 [M+H]$^+$.

EXAMPLE 82

{4-[5-(5-Cyclopropyl-3-phenyl-isoxazol-4-yl)-[1,3,4]oxadiazol-2-yl]-3-methoxy-phenyl}-(tetrahydro-pyran-4-yl)-amine As described for example 26, 2-(4-fluoro-2-methoxy-phenyl)-5-(5-cyclopropyl-3-phenyl-isoxazol-4-yl)-[1,3,4]oxadiazole (200 mg, 0.53 mmol) instead of 2-(4-fluoro-2-methoxy-phenyl)-5-(5-methyl-3-phenyl-isoxazol-4-yl)-[1,3,4]oxadiazole was converted using 4-aminotetrahydropyran (161 mg, 1.59 mmol) and N,N-diisopropylethylamine (137 mg, 1.06 mmol) instead of thiomorpholine to the title compound (SiO$_2$, heptane:ethyl acetate:dichloromethane:methanol=40:40:20:0 to 0:75:20:5, 84 mg, 35%) which was obtained as a white solid. MS: m/e=459.4 [M+H]$^+$.

EXAMPLE 83

2-(2,5-Difluoro-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2,5-difluorobenzoic acid instead of o-toluic acid to the title compound (SiO$_2$, heptane:ethyl acetate:dichloromethane=70:10:20 to 40:40:20, 211 mg, 68%) which was obtained as a white solid. MS: m/e=340.2 [M+H]$^+$.

EXAMPLE 84

2-(2,3-Difluoro-phenyl)-5-(5-methyl-3-phenyl-isoxazol-4-yl)-[1,3,4]oxadiazole

As described for example 2, 5-methyl-3-phenyl-isoxazole-4-carboxylic acid hydrazide (200 mg, 0.92 mmol) was converted using 2,3-difluorobenzoic acid instead of o-toluic acid to the title compound (SiO$_2$, heptane:ethyl acetate:dichloromethane=70:10:20 to 40:40:20, 108 mg, 35%) which was obtained as a white solid. MS: m/e=340.2 [M+H]$^+$.

EXAMPLE 85

2-(2-Methoxy-4-[1,2,3]triazol-2-yl-phenyl)-5-(5-methyl-3-phenyl-isoxazol-4-yl)-[1,3,4]oxadiazole As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 1H-1,2,3-triazole (197 mg, 2.84 mmol) and potassium carbonate (47 mg, 0.34 mmol) instead of thiomorpholine to the title compound (SiO$_2$, heptane:ethyl acetate:dichloromethane=70:10:20 to 20:60:20, 34 mg, 15%) which was obtained as a white solid. MS: m/e=401.2 [M+H]$^+$.

EXAMPLE 86

2-(2-Methoxy-4-[1,2,3]triazol-1-yl-phenyl)-5-(5-methyl-3-phenyl-isoxazol-4-yl)-[1,3,4]oxadiazole As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 1H-1,2,3-triazole (197 mg, 2.84 mmol) and potassium carbonate (47 mg, 0.34 mmol) instead of thiomorpholine to the title compound (SiO$_2$, heptane:ethyl acetate:dichloromethane=70:10:20 to 20:60:20, 56 mg, 25%) which was obtained as a white solid. MS: m/e 401.2 [M+H]$^+$.

EXAMPLE 87

2-(4,5-Difluoro-2-methoxy-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (200 mg, 0.92 mmol) was converted using 4,5-difluoro-2-methoxybenzoic acid instead of o-toluic acid to the title compound (SiO$_2$, heptane:ethyl acetate:dichloromethane=70:10:20 to 0:80:20, 168 mg, 49%) which was obtained as a white solid. MS: m/e=340.2 [M+H]$^+$.

EXAMPLE 88

{4-[5-(4-Fluoro-2-methoxy-phenyl)-[1,3,4]oxadiazol-2-yl]-3-phenyl-isoxazol-5-ylmethyl}-methyl-amine To a solution of 2-(4-fluoro-2-methoxy-phenyl)-5-(5-methyl-3-phenyl-isoxazol-4-yl)-[1,3,4]oxadiazole (241 mg, 0.69 mmol) in carbon tetrachloride (2 mL) was added N-bromosuccinimide (122 mg, 0.69 mmol) and 2,2'-azobis(2-methylpropionitrile) (11 mg, 0.07 mmol) and the reaction mixture was stirred for 18 h at 70° C. It was diluted with dichloromethane (10 mL) and washed with aqueous sodium hydrogencarbonate (1 N, 10 mL). The aqueous phase was extracted with dichloromethane and dried over sodium sulfate. The resulting crude material was suspended in methylamine solution (2 M in THF, 2.0 mL, 4.0 mmol) and potassium carbonate (110 mg, 0.80 mmol) was added. The reaction mixture was stirred for 2 h at 50° C. The mixture was diluted with ethyl acetate (20 ml), washed twice aqueous sodium carbonate (half saturated) and was extracted with ethyl acetate. Drying over sodium sulfate and purification by chromatography (SiO$_2$, heptane:ethyl acetate:dichloromethane:methanol=40:40:20:0 to 0:75:20:5) afforded the title compound (119 mg, 46%) as a white solid. MS: m/e=381.2 [M+H]$^+$.

EXAMPLE 89

N-{3-Methoxy-4-[5-(5-methyl-3-phenyl-isoxazol-4-yl)-[1,3,4]oxadiazol-2-yl]-phenyl}-acetamide To a solution of 3-methoxy-4-[5-(5-methyl-3-phenyl-isoxazol-4-yl)-[1,3,4]oxadiazol-2-yl]-phenylamine (200 mg, 0.57 mmol) in tetrahydrofuran (4 mL) were added N,N-diisopropylamine (111 mg, 0.86 mmol), 4-dimethylaminopyridine (7.0 mg, 0.06 mmol) and acetyl chloride (59 mg, 0.75 mmol) and the reaction mixture was stirred at ambient temperature for 6 h. The resulting suspension was extracted with ethyl acetate (20 mL) and the combined organic layers were washed with aqueous sodium carbonate (saturated). Drying over sodium sulfate and concentration afforded the title compound (162 mg, 72%) as a yellow solid. MS: m/e=391.2 [M+H]$^+$.

EXAMPLE 90

N-{3-Methoxy-4-[5-(5-methyl-3-phenyl-isoxazol-4-yl)-[1,3,4]oxadiazol-2-yl]-phenyl}-propionamide To a solution of 3-methoxy-4-[5-(5-methyl-3-phenyl-isoxazol-4-yl)-[1,3,4]oxadiazol-2-yl]-phenylamine (200 mg, 0.57 mmol) in tetrahydrofuran (4 mL) were added N,N-diisopropylamine (111 mg, 0.86 mmol), 4-dimethylaminopyridine (7.0 mg, 0.06 mmol) and propionyl chloride (69 mg, 0.75 mmol) and the reaction mixture was stirred at ambient temperature for 22 h. After heating at 50° C. for another 26 h the resulting suspension was extracted with ethyl acetate (20 mL) and the combined organic layers were washed with aqueous sodium carbonate (saturated). Drying over sodium sulfate and concentration afforded the title compound (206 mg, 89%) as a yellow solid. MS: m/e=405.3 [M+H]$^+$.

EXAMPLE 91

2-(4-Fluoro-2-methoxy-phenyl)-5-(5-methoxymethyl-3-phenyl-isoxazol-4-yl)-[1,3,4]oxadiazole To a solution of 2-(4-fluoro-2-methoxy-phenyl)-5-(5-methyl-3-phenyl-isoxazol-4-yl)-[1,3,4]oxadiazole (1.95 g, 5.56 mmol) in carbon tetrachloride (20 ml) was added N-bromo succinimide (990 mg, 5.56 mmol) and 2,2'-azobis(2-methylpropionitrile) (46 mg, 0.28 mmol) and the reaction mixture was stirred for 4 h at 70° C. Further 2,2'-azobis(2-methylpropionitrile) (46 mg, 0.28 mmol) was added and stirring was continued for another 14 h at 70° C. N-Bromo succinimide (378 mg, 2.12 mmol) was added and the mixture stirred for another 4 h at 90° C. After the reaction mixture was cooled to 0° C. the suspension was filtered off and was washed with dichloromethane (30 mL) and aqueous sodium hydrogencarbonate (1 N). It was extracted with dichloroemthane and dried over sodium sulfate resulting in crude material (1.66 g). A part of this light brown solid (200 mg) was dissolved in tetrahydropyran (2 mL), sodium methoxide (30% in methanol, 0.43 ml, 2.32 mmol) was added and the resulting mixture was stirred for 1 h at ambient temperature. It was diluted with ethyl acetate (20 mL) and washed aqueous ammonium chloride (saturated). The aqueous layers were extracted with ethyl acetate and the combined organic layers were dried over sodium sulfate. Purification by chromatography (SiO$_2$, heptane:ethyl acetate:dichloromethane=70:10:20 to 40:40:20) afforded the title compound (25 mg, 14%) as a white solid. MS: m/e=382.3 [M+H]$^+$.

EXAMPLE 92

{4-[5-(4-Fluoro-2-methoxy-phenyl)-[1,3,4]oxadiazol-2-yl]-3-phenyl-isoxazol-5-yl}-methanol To a solution of 2-(4-fluoro-2-methoxy-phenyl)-5-(5-methyl-3-phenyl-isoxazol-4-yl)-[1,3,4]oxadiazole (1.95 g, 5.56 mmol) in carbon tetrachloride (20 mL) was added N-bromo succinimide (990 mg, 5.56 mmol) and 2,2'-azobis(2-methylpropionitrile) (46 mg, 0.28 mmol) and the reaction mixture was stirred for 4 h at 70° C. Further 2,2'-azobis(2-methylpropionitrile) (46 mg, 0.28 mmol) was added and stirring was continued for another 14 h at 70° C. N-Bromo succinimide (378 mg, 2.12 mmol) was added and the mixture stirred for another 4 h at 90° C. After the reaction mixture was cooled to 0° C. the suspension was filtered off and was washed with dichloromethane (30 mL 1) and aqueous sodium hydrogencarbonate (1 N). It was extracted with dichloroemthane and dried over sodium sulfate resulting in crude material (1.66 g). A part of this light brown solid (200 mg) was suspended in water (0.5 mL) and DMSO (2.0 mL) and the reaction mixture was stirred for 18 h at 60° C. the resulting solution was diluted with ethyl acetate (10 mL) and washed with water (10 mL) and brine (10 mL). The aqueous layers were extracted with ethyl acetate. Drying over sodium sulfate and urification by chromatography (SiO$_2$, heptane:ethyl acetate:dichloromethane=70:10:20 to 20:60:20) afforded the title compound (57 mg, 33%) as a white solid. MS: m/e=368.1 [M+H]$^+$.

EXAMPLE 93

2-Methoxy-3-[5-(5-methyl-3-phenyl-isoxazol-4-yl)-[1,3,4]oxadiazol-2-yl]-pyridine As described for example 2, 5-methyl-3-phenyl-isoxazole-4-carboxylic acid hydrazide (200 mg, 0.92 mmol) was converted using 2-methoxynicotinic acid instead of o-toluic acid to the title compound (SiO$_2$, heptane:ethyl acetate:dichloromethane=60:20:20 to 0:80:20, 163 mg, 53%) which was obtained as a white solid. MS: m/e=335.3 [M+H]$^+$.

EXAMPLE 94

4-(4-{5-[3-(3-Chloro-phenyl)-5-methyl-isoxazol-4-yl]-[1,3,4]oxadiazol-2-yl}-3-methoxy-phenyl)-morpholine To a solution of 3-(3-chloro-phenyl)-5-methyl-isoxazole-4-carboxylic acid (200 mg, 0.85 mmol) in dichloromethane (4 mL) was added 2-methoxy-4-morpholin-4-yl-benzoic acid hydrazide (266 mg, 0.85 mmol) and 2-chloro-1,3-dimethylimidazolium chloride (313 mg, 1.85 mmol). After the solution was stirred for 15 min at ambient temperature triethylamine (0.59 ml, 4.21 mmol) was added over a period of 2 min and the reaction mixture was stirred for 18 h at this temperature. It was diluted with ethyl acetate (20 mL 1) and washed with aqueous sodium carbonate (half saturated). The aqueous layers were extracted with ethyl acetate. Drying over sodium sulfate and purification by chromatography (SiO$_2$, heptane:ethyl acetate:dichloromethane=60:20:20 to 0:80:20) afforded the title compound (235 mg, 62%) as a white solid. MS: m/e=453.1 [M+H]$^+$.

EXAMPLE 95

4-{3-Methoxy-4-[5-(3-phenyl-isoxazol-4-yl)-[1,3,4]oxadiazol-2-yl]-phenyl}-morpholine As described for example 94, 3-phenyl-isoxazole-4-carboxylic acid (*Polish Journal of Chemistry*, 56(2), 257-266, 1982, 200 mg, 1.06 mmol) instead of 3-(3-chloro-phenyl)-5-methyl-isoxazole-4-carboxylic acid was converted to the title compound (SiO$_2$, heptane:ethyl acetate:dichloromethane 60:20:20 to 0:80:20, 29 mg, 8%) which was obtained as a white solid. MS: m/e=405.3 [M+H]$^+$.

EXAMPLE 96

4-{4-[5-(3,5-Diphenyl-isoxazol-4-yl)-[1,3,4]oxadiazol-2-yl]-3-methoxy-phenyl}-morpholine As described for example 94, 3,5-diphenyl-isoxazole-4-carboxylic acid (Heterocycles, 29(4), 667-677, 1989, 200 mg, 0.75 mmol) instead of 3-(3-chloro-phenyl)-5-methyl-isoxazole-4-carboxylic acid was converted to the title compound (SiO$_2$, heptane:ethyl acetate:dichloromethane=60:20:20 to 0:80:20, 168 mg, 46%) which was obtained as a white solid. MS: m/e=481.2 [M+H]$^+$.

EXAMPLE 97

4-(4-{5-[3-(2-Chloro-phenyl)-5-methyl-isoxazol-4-yl]-[1,3,4]oxadiazol-2-yl}-3-methoxy-phenyl)-morpholine As described for example 94, 3-(2-chloro-phenyl)-5-methyl-isoxazole-4-carboxylic acid (200 mg, 0.84 mmol) instead of 3-(3-chloro-phenyl)-5-methyl-isoxazole-4-carboxylic acid was converted to the title compound (SiO$_2$, heptane:ethyl acetate:dichloromethane=60:20:20 to 0:80:20, 227 mg, 60%) which was obtained as an off-white solid. MS: m/e=453.1 [M+H]$^+$.

EXAMPLE 98

4-(4-{5-[3-(4-Fluoro-phenyl)-isoxazol-4-yl]-[1,3,4]oxadiazol-2-yl}-3-methoxy-phenyl)-morpholine As described for example 94, 3-(4-fluoro-phenyl)-isoxazole-4-carboxylic acid (WO2001029015, 200 mg, 0.90 mmol) instead of 3-(3-chloro-phenyl)-5-methyl-isoxazole-4-carboxylic acid was converted to the title compound (SiO$_2$, heptane:ethyl acetate:dichloromethane=60:20:20 to 0:80:20, 33 mg, 9%) which was obtained as an off-white solid. MS: m/e=423.1 [M+H]$^+$.

EXAMPLE 99

2-Chloro-6-methoxy-3-[5-(5-methyl-3-phenyl-isoxazol-4-yl)-[1,3,4]oxadiazol-2-yl]-pyridine a) 2,6-Dichloro-3-[5-(5-methyl-3-phenyl-isoxazol-4-yl)-[1,3,4]oxadiazol-2-yl]-pyridine As described for example 2, 5-methyl-3-phenyl-isoxazole-4-carboxylic acid hydrazide (400 mg, 1.84 mmol) was converted using 2,6-dichloronicotinic acid instead of o-toluic acid to the title compound (SiO$_2$, heptane:ethyl acetate=80:20 to 40:60, 240 mg, 35%) which was obtained as a white solid. MS: m/e=373.0/375.0 [M+H]$^+$.

a) 2-Chloro-6-methoxy-3-[5-(5-methyl-3-phenyl-isoxazol-4-yl)-[1,3,4]oxadiazol-2-yl]-pyridine To a solution of 2,6-dichloro-3-[5-(5-methyl-3-phenyl-isoxazol-4-yl)-[1,3,4]oxadiazol-2-yl]-pyridine (316 mg, 0.85 mmol) in tetrahydrofuran (3 mL) and methanol (3 mL) was added sodium hydride (55% dispersion in mineral oil, 41 mg, 0.93 mmol) and the reaction mixture was stirred for 4 h at ambient temperature. The resulting suspension was diluted with dichloromethane (10 mL) and was washed brine (half saturated, 10 mL). The aqueous layers were extracted with dichloromethane (10 mL) and dried over sodium sulfate. The filtrate was treated with tert-butylmethylether (20 mL) and the dichloromethane was distilled off. The resulting suspension was stirred for 5 min, filtered off and washed with tert-butylmethylether affording the title compound (51 mg, 16%) which was obtained as a white solid. MS: m/e=369.0 [M+H]$^+$.

EXAMPLE 100

2,6-Dimethoxy-3-[5-(5-methyl-3-phenyl-isoxazol-4-yl)-[1,3,4]oxadiazol-2-yl]-pyridine As described for example 2, 5-methyl-3-phenyl-isoxazole-4-carboxylic acid hydrazide (500 mg, 2.30 mmol) was converted using 2,6-dimethoxynicotinic acid instead of o-toluic acid to the title compound (SiO$_2$, heptane:ethyl acetate=80:20 to 40:60, 204 mg, 24%) which was obtained as a white solid. MS: m/e=365.2 [M+H]$^+$.

EXAMPLE 101

4-(4-{5-[3-(4-Fluoro-phenyl)-5-methyl-isoxazol-4-yl]-[1,3,4]oxadiazol-2-yl}-3-methoxy-phenyl)-morpholine As described for example 94, 3-(4-fluoro-phenyl)-5-methyl-isoxazole-4-carboxylic acid (132 mg, 0.60 mmol) instead of 3-(3-chloro-phenyl)-5-methyl-isoxazole-4-carboxylic acid was converted to the title compound (SiO$_2$, heptane:ethyl acetate:dichloromethane=60:20:20 to 0:80:20, 120 mg, 46%) which was obtained as a white solid. MS: m/e=437.2 [M+H]$^+$.

EXAMPLE 102

4-{3-Methoxy-4-[5-(5-methyl-3-pyridin-3-yl-isoxazol-4-yl)-[1,3,4]oxadiazol-2-yl]-phenyl}-morpholine As described for example 94, 3-pyridin-3-yl-5-methyl-isoxazole-4-carboxylic acid (122 mg, 0.60 mmol) instead of 3-(3-chloro-phenyl)-5-methyl-isoxazole-4-carboxylic acid was converted to the title compound (SiO$_2$, heptane:ethyl

EXAMPLE 103

4-(3-Methoxy-4-{5-[5-methyl-3-(4-trifluoromethyl-phenyl)-isoxazol-4-yl]-[1,3,4]oxadiazol-2-yl}-phenyl)-morpholine a) 3-(4-Trifluoro-phenyl)-5-methyl-isoxazole-4-carboxylic acid As described for example 69b, 3-(4-trifluoro-phenyl)-5-methyl-isoxazole-4-carboxylic acid ethyl ester (*Journal of Agricultural and Food Chemistry*, 43(1), 219-228, 1995, 329 mg, 1.10 mmol) instead of 5-cyclopropyl-3-phenyl-isoxazole-4-carboxylic acid ethyl ester was converted to the title compound (239 mg, 80%) which was obtained as a white solid. MS: m/e=270.4 [M−H]⁻.

b) 4-(3-Methoxy-4-{5-[5-methyl-3-(4-trifluoromethyl-phenyl)-isoxazol-4-yl]-[1,3,4]oxadiazol-2-yl}-phenyl)-morpholine As described for example 94, 3-(4-trifluoro-phenyl)-5-methyl-isoxazole-4-carboxylic acid (162 mg, 0.60 mmol) instead of 3-(3-chloro-phenyl)-5-methyl-isoxazole-4-carboxylic acid was converted to the title compound (SiO₂, heptane:ethyl acetate:dichloromethane=60:20:20 to 0:80:20, 202 mg, 70%) which was obtained as a white solid. MS: m/e=487.3 [M+H]⁺.

EXAMPLE 104

4-(3-Methoxy-4-{5-[5-methyl-3-(4-methyl-phenyl)-isoxazol-4-yl]-[1,3,4]oxadiazol-2-yl}-phenyl)-morpholine As described for example 94, 3-(4-methyl-phenyl)-5-methyl-isoxazole-4-carboxylic acid (*Journal of the Chemical Society*, 5838-5845, 1963, 130 mg, 0.60 mmol) instead of 3-(3-chloro-phenyl)-5-methyl-isoxazole-4-carboxylic acid was converted to the title compound (SiO₂, heptane:ethyl acetate:dichloromethane:methanol=40:50:10:0 to 0:90:0:10, 67 mg, 26%) which was obtained as a white solid. MS: m/e=433.3 [M+H]⁺.

EXAMPLE 105

4-{4-[5-(5-Chloro-3-phenyl-isoxazol-4-yl)-[1,3,4]oxadiazol-2-yl]-3-methoxy-phenyl}-morpholine As described for example 94, 5-chloro-3-phenyl-isoxazole-4-carboxylic acid (*Journal of Organic Chemistry*, 51(6), 945-947, 1986, 610 mg, 2.73 mmol) instead of 3-(3-chloro-phenyl)-5-methyl-isoxazole-4-carboxylic acid was converted to the title compound (SiO₂, heptane:ethyl acetate=60:40 to 0:100, 582 mg, 49%) which was obtained as a light brown solid. MS: m/e=439.1 [M+H]⁺.

EXAMPLE 106

{4-[5-(2-Methoxy-4-morpholin-4-yl-phenyl)-[1,3,4]oxadiazol-2-yl]-3-phenyl-isoxazol-5-yl}-dimethyl-amine To a suspension of 4-{4-[5-(5-chloro-3-phenyl-isoxazol-4-yl)-[1,3,4]oxadiazol-2-yl]-3-methoxy-phenyl}-morpholine (100 mg, 0.23 mmol) in DMSO (1 mL) was added dimethylamine hydrochloride (93 mg, 1.14 mmol) and potassium carbonate (158 mg, 1.14 mmol). The reaction mixture was stirred for 2 h at ambient temperature. It was diluted with water (5 mL) and the resulting suspension was stirred for 15 min at this temperature. Filtration and washing with water (5 mL) and tert-buitylmethylether (5 mL) afforded the title compound (80 mg, 78%) which was obtained as an off-white solid. MS: m/e=448.2 [M+H]⁺.

EXAMPLE 107

4-{4-[5-(2-Methoxy-4-morpholin-4-yl-phenyl)-[1,3,4]oxadiazol-2-yl]-3-phenyl-isoxazol-5-yl}-morpholine As described for example 106, 4-{4-[5-(5-chloro-3-phenyl-isoxazol-4-yl)-[1,3,4]oxadiazol-2-yl]-3-methoxy-phenyl}-morpholine (100 mg, 0.23 mmol) using morpholine instead of dimethylamine hydrochloride and potassium carbonate was converted to the title compound (100 mg, 90%) which was obtained as an off-white solid. MS: m/e=490.3 [M+H]⁺.

EXAMPLE 108

4-(4-{5-[3-(3-Fluoro-phenyl)-5-methyl-isoxazol-4-yl]-[1,3,4]oxadiazol-2-yl}-3-methoxy-phenyl)-morpholine As described for example 94, 3-(3-fluoro-phenyl)-5-methyl-isoxazole-4-carboxylic acid (*Journal of the Chemical Society*, 5838-5845, 1963, 94 mg, 0.43 mmol) instead of 3-(3-chloro-phenyl)-5-methyl-isoxazole-4-carboxylic acid was converted to the title compound (92 mg, 50%) which was obtained as a white solid. MS: m/e=437.2 [M+H]⁺.

EXAMPLE 109

4-(4-{5-[3-(4-Chloro-phenyl)-5-methyl-isoxazol-4-yl]-[1,3,4]oxadiazol-2-yl}-3-methoxy-phenyl)-morpholine As described for example 94, 3-(4-chloro-phenyl)-5-methyl-isoxazole-4-carboxylic acid (23 mg, 0.10 mmol) instead of 3-(3-chloro-phenyl)-5-methyl-isoxazole-4-carboxylic acid was converted to the title compound (SiO₂, heptane:ethyl acetate 80:20 to 20:80, 24 mg, 55%) which was obtained as a white solid. MS: m/e=453.1 [M+H]⁺.

EXAMPLE 110

4-{3-Methoxy-4-[5-(5-methyl-3-thiophen-2-yl-isoxazol-4-yl)-[1,3,4]oxadiazol-2-yl]-phenyl}-morpholine As described for example 94, 5-methyl-3-thiophen-2-yl-isoxazole-4-carboxylic acid (*Journal of the Chemical Society*, 5838-5845, 1963, 200 mg, 0.96 mmol) instead of 3-(3-chloro-phenyl)-5-methyl-isoxazole-4-carboxylic acid was converted to the title compound (SiO₂, heptane:ethyl acetate=80:20 to 20:80, 157 mg, 39%) which was obtained as an off-white solid. MS: m/e=425.2 [M+H]⁺.

EXAMPLE 111

Ethyl-{4-[5-(2-methoxy-4-morpholin-4-yl-phenyl)-[1,3,4]oxadiazol-2-yl]-3-phenyl-isoxazol-5-yl}-amine As described for example 106, 4-{4-[5-(5-chloro-3-phenyl-isoxazol-4-yl)-[1,3,4]oxadiazol-2-yl]-3-methoxy-phenyl}-morpholine (100 mg, 0.23 mmol) using ethylamine instead of dimethylamine hydrochloride and potassium carbonate was converted to the title compound (88 mg, 86%) which was obtained as a white solid. MS: m/e=448.3 [M+H]$^+$.

EXAMPLE 112

4,4-Difluoro-1-{4-[5-(5-methyl-3-phenyl-isoxazol-4-yl)-[1,3,4]oxadiazol-2-yl]-phenyl}-piperidine a) 2-(4-Iodo-phenyl)-5-(5-methyl-3-phenyl-isoxazol-4-yl)-[1,3,4]oxadiazole As described for example 2, 5-methyl-3-phenyl-isoxazole-4-carboxylic acid hydrazide (1.00 g, 4.60 mmol) was converted using 4-iodobenzoic acid instead of o-toluic acid to the title compound (SiO$_2$, heptane:ethyl acetate:dichloromethane=70:10:20 to 40:40:20, 1.21 g, 62%) which was obtained as a white solid. MS: m/e=430.2 [M+H]$^+$.

b) 4,4-Difluoro-1-{4-[5-(5-methyl-3-phenyl-isoxazol-4-yl)-[1,3,4]oxadiazol-2-yl]-phenyl}-piperidine To a solution of 2-(4-iodo-phenyl)-5-(5-methyl-3-phenyl-isoxazol-4-yl)-[1,3,4]oxadiazole (200 mg, 0.47 mmol) in toluene (2 mL) were added under an atmosphere of nitrogen 2-(dicyclohexylphosphino)biphenyl (15 mg, 0.04 mmol), tris(dibenzylideneacetone)di-palladium(0) chloroform complex (15 mg, 0.01 mmol), sodium tert-butoxide (107 mg, 1.12 mmol) and 4,4-difluoropiperidine hydrochloride (88 mg, 0.56 mmol). The reaction mixture was stirred for 1 h at 100° C. and was extracted with water (20 mL) and ethyl acetate (20 mL). The aqueous layer was extracted with ethyl acetate and the combined organic layers were washed with brine. Drying over sodium sulfate and purification by chromatography (SiO$_2$, heptane:ethyl acetate=80:20 to 50:50) afforded the title compound (138 mg, 70%) as a light yellow solid. MS: m/e=423.3 [M+H]$^+$.

EXAMPLE 113

4-{3-Methoxy-4-[5-(3-phenyl-5-pyrazol-1-yl-isoxazol-4-yl)-[1,3,4]oxadiazol-2-yl]-phenyl}-morpholine As described for example 106, 4-{4-[5-(5-chloro-3-phenyl-isoxazol-4-yl)-[1,3,4]oxadiazol-2-yl]-3-methoxy-phenyl}-morpholine (100 mg, 0.23 mmol) using pyrazole instead of dimethylamine hydrochloride was converted to the title compound (85 mg, 79%) which was obtained as an off-white solid. MS: m/e 471.3 [M+H]$^+$.

EXAMPLE 114

4-{2-Fluoro-5-methoxy-4-[5-(5-methyl-3-phenyl-isoxazol-4-yl)-[1,3,4]oxadiazol-2-yl]-phenyl}-morpholine As described for example 26, 2-(4,5-difluoro-2-methoxy-phenyl)-5-(5-methyl-3-phenyl-isoxazol-4-yl)-[1,3,4]oxadiazole (153 mg, 0.41 mmol) instead of 2-(4-fluoro-2-methoxy-phenyl)-5-(5-methyl-3-phenyl-isoxazol-4-yl)-[1,3,4]oxadiazole was converted using morpholine instead of thiomorpholine to the title compound (SiO$_2$, heptane:ethyl acetate:methanol=60:40:0 to 0:95:5, 20 mg, 11%) which was obtained as an off-white solid. MS: m/e=437.0 [M+H]$^+$.

EXAMPLE 115

4-[5-(2-Methoxy-4-morpholin-4-yl-phenyl)-[1,3,4]oxadiazol-2-yl]-3-phenyl-isoxazole-5-carbonitrile To a suspension of 4-{4-[5-(5-chloro-3-phenyl-isoxazol-4-yl)-[1,3,4]oxadiazol-2-yl]-3-methoxy-phenyl}-morpholine (145 mg, 0.33 mmol) in DMF (2 mL) was added sodium cyanide (18 mg, 0.36 mmol) and the mixture was stirred for 18 h at ambient temperature. The resulting yellow-green suspension was treated with water (15 ml) and cooled to 0° C. After stirring for 15 min at 0° C. the suspension was filtered off and washed twice with ice cold water (5 ml) affording the title compound (119 mg, 84%) which was obtained as a yellow solid. MS: m/e=430.3 [M+H]$^+$.

EXAMPLE 116

4-{2-Fluoro-5-methoxy-4-[5-(5-methyl-3-phenyl-isoxazol-4-yl)-[1,3,4]oxadiazol-2-yl]-phenyl}-thiomorpholine As described for example 26, 2-(4,5-difluoro-2-methoxy-phenyl)-5-(5-methyl-3-phenyl-isoxazol-4-yl)-[1,3,4]oxadiazole (400 mg, 1.08 mmol) instead of 2-(4-fluoro-2-methoxy-phenyl)-5-(5-methyl-3-phenyl-isoxazol-4-yl)-[1,3,4]oxadiazole was converted to the title compound (460 mg, 94%) which was obtained as an off-white solid. MS: m/e=453.2 [M+H]$^+$.

EXAMPLE 117

4-{2-Fluoro-5-methoxy-4-[5-(5-methyl-3-phenyl-isoxazol-4-yl)-[1,3,4]oxadiazol-2-yl]-phenyl}-thiomorpholine 1,1-dioxide To a suspension of 4-{2-fluoro-5-methoxy-4-[5-(5-methyl-3-phenyl-isoxazol-4-yl)-[1,3,4]oxadiazol-2-yl]-phenyl}-thiomorpholine (400 mg, 0.88 mmol) in methanol (6 mL) and water (0.3 mL) was added potassium monopersulfate triple salt (1.09 g, 1.77 mmol) under an atmosphere of nitrogen and the mixture was heated for 18 h at 80° C. The reaction mixture was cooled to ambient temperature, sodium bisulfite (38% in water, 3 mL) was added and stirred for 0.5 h at ambient temperature. The resulting suspension was extracted with dichloromethane (20 mL) and washed with aqueous sodium carbonate (half saturated). Drying over sodium sulfate and purification by chromatography (SiO$_2$, heptane:ethyl acetate:dichloromethane=40:40:20 to 10:70:20) afforded the title compound (228 mg, 53%) as a white solid. MS: m/e=485.3 [M+H]$^+$.

EXAMPLE 118

2-(5-Methyl-3-phenyl-isoxazol-4-yl)-5-(2,4,5-trifluoro-phenyl)-[1,3,4]oxadiazole As described for example 2, 5-methyl-3-phenyl-isoxazole-4-carboxylic acid hydrazide (4.18 g, 19.2 mmol) was converted using 2,4,5-trifluorobenzoic acid instead of o-toluic acid to the title compound (3.16 g, 46%) which was obtained as a white solid. MS: m/e=358.1 [M+H]$^+$.

EXAMPLE 119

4-{2,5-Difluoro-4-[5-(5-methyl-3-phenyl-isoxazol-4-yl)-[1,3,4]oxadiazol-2-yl]-phenyl}-thiomorpholine As described for example 26, 2-(2,4,5-trifluoro-phenyl)-5-(5-methyl-3-phenyl-isoxazol-4-yl)-[1,3,4]oxadiazole (400 mg, 1.12 mmol) instead of 2-(4-fluoro-2-methoxy-phenyl)-5-(5-methyl-3-phenyl-isoxazol-4-yl)-[1,3,4]oxadiazole was converted to the title compound (348 mg, 71%) which was obtained as an off-white solid. MS: m/e=441.2 [M+H]$^+$.

EXAMPLE 120

4-{2,5-Difluoro-4-[5-(5-methyl-3-phenyl-isoxazol-4-yl)-[1,3,4]oxadiazol-2-yl]-phenyl}-thiomorpholine 1,1-dioxide As described for example 117, 4-{2,5-difluoro-4-[5-(5-methyl-3-phenyl-isoxazol-4-yl)-[1,3,4]oxadiazol-2-yl]-phenyl}-thiomorpholine (208 mg, 0.47 mmol) instead of 4-{2-fluoro-5-methoxy-4-[5-(5-methyl-3-phenyl-isoxazol-4-yl)-[1,3,4]oxadiazol-2-yl]-phenyl}-thiomorpholine was converted to the title compound (SiO$_2$, heptane:ethyl acetate:dichloromethane=40:40:20 to 10:70:20, 129 mg, 58%) which was obtained as an off-white solid. MS: m/e=473.3 [M+H]$^+$.

EXAMPLE 121

2-(5-Methyl-3-phenyl-isoxazol-4-yl)-5-thiophen-2-yl-[1,3,4]oxadiazole

To a suspension of 5-methyl-3-phenylisoxazole-4-carboxylic acid (357 mg, 1.76 mmol) in dichloromethane (7 mL) was added thiophene-2-carboxylic acid hydrazide (250 mg, 1.76 mmol) and 2-chloro-1,3-dimethylimidazolium chloride (654 mg, 3.87 mmol). After the solution was stirred for 15 min at ambient temperature triethylamine (1.2 mL, 8.79 mmol) was added at 0° C. and the light brown suspension was stirred for 18 h while warming to ambient temperature. It was washed with water (25 mL) and aqueous sodium carbonate (half saturated, 25 mL). The aqueous layers were extracted with dichloromethane and the combined organic layers were dried over sodium sulfate. Purification by chromatography (SiO$_2$, heptane:ethyl acetate=100:0 to 70:30) afforded the title compound (233 mg, 43%) as a light yellow semisolid. MS: m/e=310.3 [M+H]$^+$.

EXAMPLE 122

2-(5-Methyl-3-phenyl-isoxazol-4-yl)-5-thiophen-3-yl-[1,3,4]oxadiazole

As described for example 121, 5-methyl-3-phenylisoxazole-4-carboxylic acid (357 mg, 1.76 mmol) using thiophene-3-carboxylic acid hydrazide instead of thiophene-2-carboxylic acid hydrazide was converted to the title compound (SiO$_2$, heptane:ethyl acetate=90:10 to 60:40, 207 mg, 38%) which was obtained as a yellow semisolid. MS: m/e=310.3 [M+H]$^+$.

EXAMPLE 123

4-{3-Methoxy-4-[5-(5-methyl-3-thiophen-3-yl-isoxazol-4-yl)-[1,3,4]oxadiazol-2-yl]-phenyl}-morpholine a) 5-Methyl-3-thiophen-3-yl-isoxazole-4-carboxylic acid ethyl ester As described for example 69a, N-hydroxy-thiophene-3-carboximidoyl chloride (*Organic Letters*, 8(17), 3679-3680, 2006, 11.4 g, 69.6 mmol) instead of N-hydroxybenzenecarboximidoyl chloride using ethyl 2-butynoate instead of cyclopropyl-propynoic acid ethyl ester was converted to the title compound (15.0 g, 91%) which was obtained as a dark brown liquid. MS: m/e=238.0 [M+H]$^+$.

b) 5-Methyl-3-thiophen-3-yl-isoxazole-4-carboxylic acid

As described for example 69b, 5-methyl-3-thiophen-3-yl-isoxazole-4-carboxylic acid ethyl ester (2.73 g, 11.5 mmol) instead of 5-cyclopropyl-3-phenyl-isoxazole-4-carboxylic acid ethyl ester was converted to the title compound (1.60 g, 67%) which was obtained as a brown solid. MS: m/e=210.1 [M+H]$^+$.

c) 4-{3-Methoxy-4-[5-(5-methyl-3-thiophen-3-yl-isoxazol-4-yl)-[1,3,4]oxadiazol-2-yl]-phenyl}-morpholine As described for example 94, 5-methyl-3-thiophen-3-yl-isoxazole-4-carboxylic acid (200 mg, 0.96 mmol) instead of 3-(3-chloro-phenyl)-5-methyl-isoxazole-4-carboxylic acid was converted to the title compound (SiO$_2$, ethyl acetate:dichloromethane=10:90 to 30:70, 35 mg, 10%) which was obtained as an off-white solid. MS: m/e=378.2 [M+H]$^+$.

EXAMPLE 124

(2-Methoxy-ethyl)-{3-methoxy-4-[5-(5-methyl-3-phenyl-isoxazol-4-yl)-[1,3,4]oxadiazol-2-yl]-phenyl}-amine As described for example 26, 2-(4-fluoro-2-methoxy-phenyl)-5-(5-methyl-3-phenyl-isoxazol-4-yl)-[1,3,4]oxadiazole (200 mg, 0.57 mmol) was converted using 2-methoxyethylamine instead of thiomorpholine to the title compound (SiO$_2$, heptane:ethyl acetate=50:50 to 0:100, 78 mg, 34%) which was obtained as an off-white foam. MS: m/e=407.4 [M+H]$^+$.

EXAMPLE 125

4-[5-(5-Methyl-3-phenyl-isoxazol-4-yl)-[1,3,4]oxadiazol-2-yl]-1H-benzoimidazole

As described for example 2, 5-methyl-3-phenyl-isoxazole-4-carboxylic acid hydrazide (200 mg, 0.92 mmol) was converted using 1H-benzoimidazole-4-carboxylic acid instead of o-toluic acid to the title compound (SiO$_2$, dichloromethane:methanol:ammonia=95:5:0)=100:0 to 80:20, 32 mg, 10%) which was obtained as a white solid. MS: m/e=344.2 [M+H]$^+$.

EXAMPLE 126

{2-Fluoro-5-methoxy-4-[5-(5-methyl-3-phenyl-isoxazol-4-yl)-[1,3,4]oxadiazol-2-yl]-phenyl}-(2-methylsulfanyl-ethyl)-amine As described for example 26, 2-(4,5-difluoro-2-methoxy-phenyl)-5-(5-methyl-3-phenyl-isoxazol-4-yl)-[1,3,4]oxadiazole (300 mg, 0.81 mmol) instead of 2-(4-fluoro-2-methoxyphenyl)-5-(5-methyl-3-phenyl-isoxazol-4-yl)-[1,3,4] oxadiazole was converted using 2-(methylthio)ethylamine instead of thiomorpholine to the title compound (273 mg, 76%) which was obtained as an off-white solid. MS: m/e 441.2 [M+H]$^+$.

EXAMPLE 127

{2-Fluoro-5-methoxy-4-[5-(5-methyl-3-phenyl-isoxazol-4-yl)-[1,3,4]oxadiazol-2-yl]-phenyl}-(2-methanesulfonyl-ethyl)-amine As described for example 117, {2-fluoro-5-methoxy-4-[5-(5-methyl-3-phenyl-isoxazol-4-yl)-[1,3,4]oxadiazol-2-yl]-phenyl}-(2-methylsulfanyl-ethyl)-amine (200 mg, 0.45 mmol) instead of 4-{2-fluoro-5-methoxy-4-[5-(5-methyl-3-phenyl-isoxazol-4-yl)-[1,3,4]oxadiazol-2-yl]-phenyl}-thiomorpholine was converted to the title compound (SiO$_2$, heptane:ethyl acetate:methanol=50:50:0 to 0:95:5, 140 mg, 65%) which was obtained as an off-white solid. MS: m/e=473.1 [M+H]$^+$.

EXAMPLE 128

1-(2-{2-Fluoro-5-methoxy-4-[5-(5-methyl-3-phenyl-isoxazol-4-yl)-[1,3,4]oxadiazol-2-yl]-phenylamino}-ethyl)-pyrrolidin-2-one As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using 1-(2-amino-ethyl)-pyrrolidin-2-one instead of thiomorpholine to the title compound (231 mg, 89%) which was obtained as an off-white solid. MS: m/e=478.2 [M+H]$^+$.

EXAMPLE 129

2-{2-Fluoro-5-methoxy-4-[5-(5-methyl-3-phenyl-isoxazol-4-yl)-[1,3,4]oxadiazol-2-yl]-phenylamino}-ethanol As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using ethanolamine instead of thiomorpholine to the title compound (160 mg, 72%) which was obtained as an off-white solid. MS: m/e=411.2 [M+H]$^+$.

EXAMPLE 130 rac-{2-Fluoro-5-methoxy-4-[5-(5-methyl-3-phenyl-isoxazol-4-yl)-[1,3,4]oxadiazol-2-yl]-phenyl}-(tetrahydro-furan-2-ylmethyl)-amine As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using rac-tetrahydrofurfurylamine instead of thiomorpholine to the title compound (129 mg, 53%) which was obtained as an off-white solid. MS: m/e=451.2 [M+H]$^+$.

EXAMPLE 131

{2-Fluoro-5-methoxy-4-[5-(5-methyl-3-phenyl-isoxazol-4-yl)-[1,3,4]oxadiazol-2-yl]-phenyl}-pyridin-2-ylmethyl-amine As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using 2-(aminoethyl)pyridine instead of thiomorpholine to the title compound (188 mg, 76%) which was obtained as an off-white solid. MS: m/e=458.3 [M+H]$^+$.

EXAMPLE 132

{2-Fluoro-5-methoxy-4-[5-(5-methyl-3-phenyl-isoxazol-4-yl)-[1,3,4]oxadiazol-2-yl]-phenyl}-(2-pyrrolidin-1-yl-ethyl)-amine As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using 1-(2-aminoethyl)pyrrolidine instead of thiomorpholine to the title compound (145 mg, 58%) which was obtained as an off-white solid. MS: m/e=464.2 [M+H]$^+$.

EXAMPLE 133

1-(2-{2-Fluoro-5-methoxy-4-[5-(5-methyl-3-phenyl-isoxazol-4-yl)-[1,3,4]oxadiazol-2-yl]-phenylamino}-ethyl)-imidazolidin-2-one As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using 1-(2-aminoethyl)imidazolidin-2-one instead of thiomorpholine to the title compound (203 mg, 78%) which was obtained as an off-white solid. MS: m/e 479.2 [M+H]$^+$.

EXAMPLE 134

N-{3-Methoxy-4-[5-(5-methyl-3-phenyl-isoxazol-4-yl)-[1,3,4]oxadiazol-2-yl]-phenyl}-formamide A mixture of 3-methoxy-4-[5-(5-methyl-3-phenyl-isoxazol-4-yl)-[1,3,4]oxadiazol-2-yl]-phenylamine (200 mg, 0.57 mmol) and formic acid (2.1 mL, 55.6 mmol) was stirred at 90° C. for 2 h. After concentration purification of the residue by chromatography (SiO$_2$, heptane:ethyl acetate: methanol=50:50:0 to 0:95:5) afforded the title compound (21 mg, 10%) as a yellow solid. MS: m/e=377.3 [M+H]$^+$.

EXAMPLE 135

N'-{2-Fluoro-5-methoxy-4-[5-(5-methyl-3-phenyl-isoxazol-4-yl)-[1,3,4]oxadiazol-2-yl]-phenyl}-N,N-dimethyl-ethane-1,2-diamine As described for example 26, 2-(4,5-difluoro-2-methoxyphenyl)-5-(5-methyl-3-phenyl-isoxazol-4-yl)-[1,3,4]oxadiazole (200 mg, 0.54 mmol) instead of 2-(4-fluoro-2-methoxyphenyl)-5-(5-methyl-3-phenyl-isoxazol-4-yl)-[1,3,4] oxadiazole was converted using N,N-dimethylethylenediamine instead of thiomorpholine to the title compound (202 mg, 85%) which was obtained as an off-white solid. MS: m/e=438.4 [M+H]$^+$.

EXAMPLE 136

4-{5-[5-(5-Methyl-3-phenyl-isoxazol-4-yl)-[1,3,4] oxadiazol-2-yl]-pyridin-2-yl}-morpholine a) 2-Chloro-5-[5-(5-methyl-3-phenyl-isoxazol-4-yl)-[1,3,4] oxadiazol-2-yl]-pyridine To a solution of 5-methyl-3-phenyl-isoxazole-4-carboxylic acid hydrazide (5.00 g, 23.0 mmol) in dichloromethane (100 mL) was added 6-chloronicotinic acid (4.71 g, 29.9 mmol) and 2-chloro-1,3-dimethylimidazolium chloride (8.56 g, 50.6 mmol). After the suspension was stirred for 15 min at ambient temperature, it was cooled to 0° C. and N,N-diisopropyl ethyl amine (19.7 mL, 115 mmol) was added slowly. The reaction mixture was stirred for 18 h while warming to ambient temperature. It was washed with aqueous sodium carbonate (saturated) and the aqueous layers were extracted with dichloromethane. Drying over sodium sulfate and purification by chromatography (SiO$_2$, heptane:ethyl acetate=80:20 to 50:50) afforded the title compound (4.78 g, 61%) as a light yellow solid. MS: m/e=339.2 [M+H]$^+$.

b) 4-{5-[5-(5-Methyl-3-phenyl-isoxazol-4-yl)-[1,3,4]oxadiazol-2-yl]-pyridin-2-yl}-morpholine To a solution of 2-chloro-5-[5-(5-methyl-3-phenyl-isoxazol-4-yl)-[1,3,4]oxadiazol-2-yl]-pyridine (200 mg, 0.59 mmol) in DMSO (2 mL) was added morpholine (257 mg, 2.95 mmol) and the reaction mixture was heated for 1 h at 160° C. After cooling to ambient temperature it was diluted with ethyl acetate (20 mL) and washed with aqueous sodium carbonate (saturated) and water. Drying over sodium sulfate and purification by chromatography (SiO$_2$, heptane:ethyl acetate=80:20 to 70:30) afforded the title compound (162 g, 70%) as a white solid. MS: m/e=390.3 [M+H]$^+$.

EXAMPLE 137

2-{5-[5-(5-Methyl-3-phenyl-isoxazol-4-yl)-[1,3,4] oxadiazol-2-yl]-pyridin-2-ylamino}-ethanol As described for example 136b, 2-chloro-5-[5-(5-methyl-3-phenyl-isoxazol-4-yl)-[1,3,4]oxadiazol-2-yl]-pyridine (200 mg, 0.59 mmol) was converted using ethanolamine instead of morpholine to the title compound (126 mg, 59%) which was obtained as an off-white solid. MS: m/e=364.3 [M+H]$^+$.

EXAMPLE 138

4-{5-[5-(5-Methyl-3-phenyl-isoxazol-4-yl)-[1,3,4] oxadiazol-2-yl]-pyridin-2-yl}-thiomorpholine As described for example 136b, 2-chloro-5-[5-(5-methyl-3-phenyl-isoxazol-4-yl)-[1,3,4]oxadiazol-2-yl]-pyridine (400 mg, 1.18 mmol) was converted using thiomorpholine instead of morpholine to the title compound (126 mg, 59%) which was obtained as an off-white solid. MS: m/e=406.3 [M+H]$^+$.

EXAMPLE 139

{5-[5-(5-Methyl-3-phenyl-isoxazol-4-yl)-[1,3,4] oxadiazol-2-yl]-pyridin-2-yl}-(tetrahydro-pyran-4-yl)-amine As described for example 136b, 2-chloro-5-[5-(5-methyl-3-phenyl-isoxazol-4-yl)-[1,3,4]oxadiazol-2-yl]-pyridine (200 mg, 0.59 mmol) was converted using 4-aminotetrahydropyran instead of morpholine to the title compound (117 mg, 49%) which was obtained as a light yellow solid. MS: m/e=404.4 [M+H]$^+$.

EXAMPLE 140

5'-[5-(5-Methyl-3-phenyl-isoxazol-4-yl)-[1,3,4]oxadiazol-2-yl]-3,4,5,6-tetrahydro-2H-[1,2']bipyridinyl-4-ol As described for example 136b, 2-chloro-5-[5-(5-methyl-3-phenyl-isoxazol-4-yl)-[1,3,4]oxadiazol-2-yl]-pyridine (200 mg, 0.59 mmol) was converted using 4-hydroxypiperidine instead of morpholine to the title compound (17 mg, 7%) which was obtained as a light yellow solid. MS: m/e=404.5 [M+H]$^+$.

EXAMPLE 141

4-{5-[5-(5-Methyl-3-phenyl-isoxazol-4-yl)-[1,3,4] oxadiazol-2-yl]-pyridin-2-yl}-thiomorpholine 1,1-dioxide As described for example 117, 4-{5-[5-(5-methyl-3-phenyl-isoxazol-4-yl)-[1,3,4]oxadiazol-2-yl]-pyridin-2-yl}-thiomorpholine (200 mg, 0.49 mmol) instead of 4-{2-fluoro-5-methoxy-4-[5-(5-methyl-3-phenyl-isoxazol-4-yl)-[1,3,4] oxadiazol-2-yl]-phenyl}-thiomorpholine was converted to the title compound (SiO$_2$, heptane:ethyl acetate=50:50 to 0:100, 157 mg, 73%) which was obtained as a white solid. MS: m/e=438.1 [M+H]$^+$.

EXAMPLE 142

4-{6-[5-(5-Methyl-3-phenyl-isoxazol-4-yl)-[1,3,4] oxadiazol-2-yl]-pyridin-3-yl}-morpholine a) 5-Bromo-2-[5-(5-methyl-3-phenyl-isoxazol-4-yl)-[1,3,4] oxadiazol-2-yl]-pyridine As described for example 137a, 5-methyl-3-phenyl-isoxazole-4-carboxylic acid hydrazide (4.14 g, 19.0 mmol) using 5-bromo-2-carboxy pyridine instead of 6-chloronicotinic acid was converted to the title compound (2.83 g, 39%) which was obtained as a brown solid. MS: m/e=385.1 [M+H]$^+$.

b) 4-{6-[5-(5-Methyl-3-phenyl-isoxazol-4-yl)-[1,3,4]oxadiazol-2-yl]-pyridin-3-yl}-morpholine A mixture of 5-bromo-2-[5-(5-methyl-3-phenyl-isoxazol-4-yl)-[1,3,4]oxadiazol-2-yl]-pyridine (200 mg, 0.52 mmol), morpholine (455 µL, 5.22 mmol) and tetrabutylammonium iodide (41 mg, 0.10 mmol) was irradiated in the microwave for 1.5 h at 160° C. After cooling to ambient temperature the resulting suspension was diluted with ethyl acetate (15 mL) and stirred for 15 min at this temperature. Filtering off and washing with water (2 mL) and with ethyl acetate (1 mL) afforded the title compound (95 mg, 47%) which was obtained as a light brown solid. MS: m/e=390.3 [M+H]$^+$.

The invention claimed is:
1. A compound of formula I

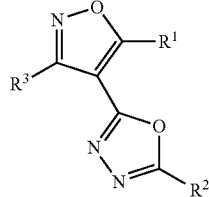

wherein
R¹ is hydrogen, halogen, aryl, heterocyclyl, heteroaryl, cyano, lower alkyl, —(CH₂)ₙ-cycloalkyl, —(CH₂)ₙ—N(R)₂, —(CH₂)ₙ—O-lower alkyl or —(CH₂)ₙ—OH;
n is 0, 1 or 2
R is hydrogen or lower alkyl;
R² is heteroaryl selected from the group consisting of quinolyl, indolyl, pyridinyl, triazolyl, benzotriazolyl, isoxazolyl, thiophenyl, benzoimidazolyl, dihydrobenzimidazolyl-2-one, imidazolyl, oxazolyl, oxadiazolyl and pyrazinyl or is heterocyclyl, each of which is optionally substituted by one or more substituents, selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NRᵃRᵇ, —C(O)—NRᵃRᵇ, —C(O)-heterocyclyl, benzyloxy, heterocyclyl optionally substituted by hydroxy, halogen or lower alkyl, or is heteroaryl optionally substituted by lower alkyl;
Rᵃ and Rᵇ are independently hydrogen, lower alkylsulfonyl, —C(O)H, —(CH₂)ₙ—N(R)₂, —(CH₂)ₙ—O-lower alkyl, —(CH₂)ₙ—S-lower alkyl, —(CH₂)ₙ—S(O)₂-lower alkyl, heteroarylsulfonyl, lower alkyl, —(CH₂)ₙ-heterocyclyl, optionally substituted by lower alkyl, or is —(CH₂)ₙ-cycloalkyl, —(CH₂)ₙ-heteroaryl, —(CH₂)ₙ—OH, —(CO)—R', wherein R' is lower alkyl, cycloalkyl or heteroaryl;
R³ is aryl or heteroaryl, which are optionally substituted by halogen or lower alkyl substituted by halogen;
or a pharmaceutically acceptable acid addition salt thereof.

2. The compound of claim 1, wherein R² is heteroaryl selected from the group consisting of quinolyl, indolyl, pyridinyl, triazolyl, benzotriazolyl, isoxazolyl, thiophenyl, benzoimidazolyl, dihydrobenzimidazolyl-2-one, imidazolyl, oxazolyl, oxadiazolyl and pyrazinyl, which is optionally substituted by one or more substituent, selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NRᵃRᵇ, —C(O)—NRᵃRᵇ, —C(O)-heterocyclyl, benzyloxy, and heterocyclyl optionally substituted by hydroxy, halogen or lower alkyl, or is heteroaryl optionally substituted by lower alkyl.

3. The compound of claim 2, selected from the group consisting of
2-chloro-3-[5-(5-methyl-3-phenyl-isoxazol-4-yl)-[1,3,4]oxadiazol-2-yl]-pyridine,
8-[5-(5-methyl-3-phenyl-isoxazol-4-yl)-[1,3,4]oxadiazol-2-yl]-quinoline,
2-[5-(5-methyl-3-phenyl-isoxazol-4-yl)-[1,3,4]oxadiazol-2-yl]-pyridine,
5-[5-(5-methyl-3-phenyl-isoxazol-4-yl)-[1,3,4]oxadiazol-2-yl]-1H-benzoimidazole,
5-[5-(5-methyl-3-phenyl-isoxazol-4-yl)-[1,3,4]oxadiazol-2-yl]-1,3-dihydro-benzoimidazol-2-one,
4-[5-(5-methyl-3-phenyl-isoxazol-4-yl)-[1,3,4]oxadiazol-2-yl]-pyridine,
4-[5-(5-methyl-3-phenyl-isoxazol-4-yl)-[1,3,4]oxadiazol-2-yl]-quinoline,
5-[5-(5-methyl-3-phenyl-isoxazol-4-yl)-[1,3,4]oxadiazol-2-yl]-pyridin-2-ylamine, and
1,3-dimethyl-5-[5-(5-methyl-3-phenyl-isoxazol-4-yl)-[1,3,4]oxadiazol-2-yl]-1,3-dihydro-benzoimidazol-2-one.

4. The compound of claim 2, selected from the group consisting of
5-[5-(5-isopropyl-3-phenyl-isoxazol-4-yl)-[1,3,4]oxadiazol-2-yl]-1,3-dimethyl-1,3-dihydro-benzoimidazol-2-one,
2-chloro-4-[5-(5-methyl-3-phenyl-isoxazol-4-yl)-[1,3,4]oxadiazol-2-yl]-pyridine,
4-{4-[5-(5-methyl-3-phenyl-isoxazol-4-yl)-[1,3,4]oxadiazol-2-yl]-pyridin-2-yl}-morpholine,
5-[5-(5-methyl-3-phenyl-isoxazol-4-yl)-[1,3,4]oxadiazol-2-yl]-1H-indole,
2-methoxy-3-[5-(5-methyl-3-phenyl-isoxazol-4-yl)-[1,3,4]oxadiazol-2-yl]-pyridine,
2-chloro-6-methoxy-3-[5-(5-methyl-3-phenyl-isoxazol-4-yl)-[1,3,4]oxadiazol-2-yl]-pyridine,
2,6-dimethoxy-3-[5-(5-methyl-3-phenyl-isoxazol-4-yl)-[1,3,4]oxadiazol-2-yl]-pyridine,
2-(5-Methyl-3-phenyl-isoxazol-4-yl)-5-thiophen-2-yl-[1,3,4]oxadiazole, and
2-(5-methyl-3-phenyl-isoxazol-4-yl)-5-thiophen-3-yl-[1,3,4]oxadiazole.

5. The compound of claim 2, selected from the group consisting of
4-[5-(5-methyl-3-phenyl-isoxazol-4-yl)-[1,3,4]oxadiazol-2-yl]-1H-benzoimidazole,
4-{5-[5-(5-methyl-3-phenyl-isoxazol-4-yl)-[1,3,4]oxadiazol-2-yl]-pyridin-2-yl}-morpholine,
2-{5-[5-(5-methyl-3-phenyl-isoxazol-4-yl)-[1,3,4]oxadiazol-2-yl]-pyridin-2-ylamino}ethanol,
4-{5-[5-(5-methyl-3-phenyl-isoxazol-4-yl)-[1,3,4]oxadiazol-2-yl]-pyridin-2-yl}-thiomorpholine,
{5-[5-(5-methyl-3-phenyl-isoxazol-4-yl)-[1,3,4]oxadiazol-2-yl]-pyridin-2-yl}-(tetrahydro-pyran-4-yl)-amine,
5'-[5-(5-methyl-3-phenyl-isoxazol-4-yl)-[1,3,4]oxadiazol-2-yl]-3,4,5,6-tetrahydro-2H-[1,2']bipyridinyl-4-ol,
4-{5-[5-(5-methyl-3-phenyl-isoxazol-4-yl)-[1,3,4]oxadiazol-2-yl]-pyridin-2-yl}thiomorpholine 1,1-dioxide and
4-{6-[5-(5-methyl-3-phenyl-isoxazol-4-yl)-[1,3,4]oxadiazol-2-yl]-pyridin-3-yl}-morpholine.

6. The compound of claim 1, wherein R² is heterocyclyl, which is optionally substituted by one or more substituents, selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NRᵃRᵇ, —C(O)—NRᵃRᵇ, —C(O)-heterocyclyl, benzyloxy, and heterocyclyl optionally substituted by hydroxy, halogen or lower alkyl, or is heteroaryl optionally substituted by lower alkyl.

7. The compound of claim 1, wherein R² is pyridinyl optionally substituted by halogen, lower alkoxy, heterocyclyl or NRᵃRᵇ.

8. The compound of claim 7, selected from the group consisting of
2-chloro-3-[5-(5-methyl-3-phenyl-isoxazol-4-yl)-[1,3,4]oxadiazol-2-yl]-pyridine,
2-[5-(5-methyl-3-phenyl-isoxazol-4-yl)-[1,3,4]oxadiazol-2-yl]-pyridine,
4-[5-(5-methyl-3-phenyl-isoxazol-4-yl)-[1,3,4]oxadiazol-2-yl]-pyridine,
5-[5-(5-methyl-3-phenyl-isoxazol-4-yl)-[1,3,4]oxadiazol-2-yl]-pyridin-2-ylamine,
2-chloro-4-[5-(5-methyl-3-phenyl-isoxazol-4-yl)-[1,3,4]oxadiazol-2-yl]-pyridine,
4-{4-[5-(5-methyl-3-phenyl-isoxazol-4-yl)-[1,3,4]oxadiazol-2-yl]-pyridin-2-yl}-morpholine,
2-methoxy-3-[5-(5-methyl-3-phenyl-isoxazol-4-yl)-[1,3,4]oxadiazol-2-yl]-pyridine, and
2-chloro-6-methoxy-3-[5-(5-methyl-3-phenyl-isoxazol-4-yl)-[1,3,4]oxadiazol-2-yl]-pyridine.

9. The compound of claim 7, selected from the group consisting of
2,6-dimethoxy-3-[5-(5-methyl-3-phenyl-isoxazol-4-yl)-[1,3,4]oxadiazol-2-yl]-pyridine,
4-{5-[5-(5-methyl-3-phenyl-isoxazol-4-yl)-[1,3,4]oxadiazol-2-yl]-pyridin-2-yl}-morpholine,
[5-(5-methyl-3-phenyl-isoxazol-4-yl)-[1,3,4]oxadiazol-2-yl]-pyridin-2-ylamino}-ethanol,
4-{5-[5-(5-methyl-3-phenyl-isoxazol-4-yl)-[1,3,4]oxadiazol-2-yl]-pyridin-2-yl}-thiomorpholine,
{5-[5-(5-methyl-3-phenyl-isoxazol-4-yl)-[1,3,4]oxadiazol-2-yl]-pyridin-2-yl}-(tetrahydro-pyran-4-yl)-amine,
5'-[5-(5-methyl-3-phenyl-isoxazol-4-yl)-[1,3,4]oxadiazol-2-yl]-3,4,5,6-tetrahydro-2H-[1,2']bipyridinyl-4-ol,
4-{5-[5-(5-methyl-3-phenyl-isoxazol-4-yl)-[1,3,4]oxadiazol-2-yl]-pyridin-2-yl}-thiomorpholine 1,1-dioxide and
4-{6-[5-(5-methyl-3-phenyl-isoxazol-4-yl)-[1,3,4]oxadiazol-2-yl]-pyridin-3-yl}-morpholine.

10. The compound of claim 1, wherein $R^2$ is quinolinyl.

11. The compound of claim 10, selected from the group consisting of
8-[5-(5-methyl-3-phenyl-isoxazol-4-yl)-[1,3,4]oxadiazol-2-yl]-quinoline and
4-[5-(5-methyl-3-phenyl-isoxazol-4-yl)-[1,3,4]oxadiazol-2-yl]-quinoline.

12. The compound of claim 1, wherein $R^2$ is 1-H-benzoimidazol-5-yl, 1,3-dihydro-benzolimidazol-2-on-5-yl or 1,3-dimethyl-1,3-dihydro-benzoimidazol-2-on-5-yl.

13. The compound claim 12, selected from the group consisting of
5-[5-(5-methyl-3-phenyl-isoxazol-4-yl)-[1,3,4]oxadiazol-2-yl]-1H-benzoimidazole,
5-[5-(5-methyl-3-phenyl-isoxazol-4-yl)-[1,3,4]oxadiazol-2-yl]-1,3-dihydro-benzoimidazol-2-one,
1,3-dimethyl-5-[5-(5-methyl-3-phenyl-isoxazol-4-yl)-[1,3,4]oxadiazol-2-yl]-1,3-dihydro-benzoimidazol-2-one and
5-[5-(5-isopropyl-3-phenyl-isoxazol-4-yl)-[1,3,4]oxadiazol-2-yl]-1,3-dimethyl-1,3-dihydro-benzoimidazol-2-one.

14. A pharmaceutical composition comprising a compound of formula I

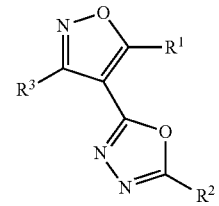

wherein
$R^1$ is hydrogen, halogen, aryl, heterocyclyl, heteroaryl, cyano, lower alkyl, —$(CH_2)_n$-cycloalkyl, —$(CH_2)_n$—N$(R)_2$, —$(CH_2)_n$—O-lower alkyl or —$(CH_2)_n$—OH;
n is 0, 1 or 2
R is hydrogen or lower alkyl;
$R^2$ is heteroaryl selected from the group consisting of quinolyl, indolyl, pyridinyl, triazolyl, benzotriazolyl, isoxazolyl, thiophenyl, benzoimidazolyl, dihydrobenzimidazolyl-2-one, imidazolyl, oxazolyl, oxadiazolyl and pyrazinyl or is heterocyclyl, each of which is optionally substituted by one or more substituents, selected from the group consisting of halogen, cyano, nitro, lower alkyl, lower alkoxy, lower alkoxy substituted by halogen, lower alkyl substituted by halogen, C(O)O-lower alkyl, lower alkylsulfonyl, —NR$^a$R$^b$, —C(O)—NR$^a$R$^b$, —C(O)-heterocyclyl, benzyloxy, heterocyclyl optionally substituted by hydroxy, halogen or lower alkyl, or is heteroaryl optionally substituted by lower alkyl;
R$^a$ and R$^b$ are independently hydrogen, lower alkylsulfonyl, —C(O)H, —$(CH_2)_n$—N$(R)_2$, —$(CH_2)_n$—O-lower alkyl, —$(CH_2)_n$—S-lower alkyl, —$(CH_2)_n$—S(O)$_2$-lower alkyl, heteroarylsulfonyl, lower alkyl, —$(CH_2)_n$-heterocyclyl, optionally substituted by lower alkyl, or is —$(CH_2)_n$-cycloalkyl, —$(CH_2)_n$-heteroaryl, —$(CH_2)_n$—OH, —(CO)—R', wherein R' is lower alkyl, cycloalkyl or heteroaryl;
$R^3$ is aryl or heteroaryl, which are optionally substituted by halogen or lower alkyl substituted by halogen;
or a pharmaceutically acceptable acid addition salt thereof and a pharmaceutically acceptable carrier.

* * * * *